(12) United States Patent
Jiao et al.

(10) Patent No.: US 12,391,992 B2
(45) Date of Patent: Aug. 19, 2025

(54) KIT FOR EARLY SCREENING OF LIVER CELL CANCER AND PREPARATION METHOD AND USE THEREOF

(71) Applicants: GENETRON HEALTH (BEIJING) CO, LTD., Beijing (CN); CANCER HOSPITAL, CHINESE ACADEMY OF MEDICAL SCIENCES, Beijing (CN)

(72) Inventors: Yuchen Jiao, Beijing (CN); Chunfeng Qu, Beijing (CN); Yuting Wang, Beijing (CN); Pei Wang, Beijing (CN); Kun Chen, Beijing (CN); Qianqian Song, Beijing (CN); Hui Liu, Beijing (CN); Sizhen Wang, Beijing (CN); Hai Yan, Beijing (CN)

(73) Assignees: GENETRON HEALTH (BEIJING) CO, LTD., Beijing (CN); CANCER HOSPITAL, CHINESE ACADEMY OF MEDICAL SCIENCES, Beijing (CN)

(*) Notice: Subject to any disclaimer, the term of this patent is extended or adjusted under 35 U.S.C. 154(b) by 846 days.

(21) Appl. No.: 17/438,050

(22) PCT Filed: Sep. 17, 2019

(86) PCT No.: PCT/CN2019/106064
§ 371 (c)(1),
(2) Date: Sep. 10, 2021

(87) PCT Pub. No.: WO2020/181752
PCT Pub. Date: Sep. 17, 2020

(65) Prior Publication Data
US 2022/0145399 A1  May 12, 2022

(30) Foreign Application Priority Data
Mar. 11, 2019 (CN) .................. 201910179499.X

(51) Int. Cl.
| | | |
|---|---|---|
| *C12Q 1/68* | (2018.01) | |
| *C12Q 1/6883* | (2018.01) | |
| *C12Q 1/6886* | (2018.01) | |
| *G01N 33/574* | (2006.01) | |
| *G16B 5/20* | (2019.01) | |
| *G16B 40/00* | (2019.01) | |
| *G16H 50/30* | (2018.01) | |
| *G16H 50/50* | (2018.01) | |

(52) U.S. Cl.
CPC ..... *C12Q 1/6886* (2013.01); *G01N 33/57438* (2013.01); *G16B 5/20* (2019.02); *G16B 40/00* (2019.02); *G16H 50/30* (2018.01); *C12Q 2600/156* (2013.01)

(58) Field of Classification Search
None
See application file for complete search history.

(56) References Cited

U.S. PATENT DOCUMENTS

2011/0033873 A1* 2/2011 Park .................. C12Q 1/6886
435/189

FOREIGN PATENT DOCUMENTS

WO  2017184883 A1  10/2017

OTHER PUBLICATIONS

Cook N.R. Statistical Evaluation of Prognostic versus Diagnostic Models: Beyond the ROC Curve. Clinical Chemistry 54(1):17-23 (2008).*
Kawai-Kitahata et al. Comprehensive analyses of mutations and hepatitis B virus integration in hepatocellular carcinoma with clinicopathological features. J Gastroenterol (2016) 51:473-486.*
Inagaki et al. Clinical and molecular insights into the hepatocellular carcinoma tumour marker des-γ-carboxyprothrombin. Liver Int. Jan. 2011;31(1):22-35.*
Ng et al. Circulating Cell-Free DNA in Hepatocellular Carcinoma: Current Insights and Outlook. Front Med (Lausanne). Mar. 26, 2018 :5:78.*
Chen, H. , et al. "Direct comparison of five serum biomarkers in early diagnosis of hepatocellular carcinoma." Cancer Management & Research 10(2018):1947-1958.
Kawai-Kitahata, F. , et al. "Comprehensive analyses of mutations and hepatitis B virus integration in hepatocellular carcinoma with clinicopathological features." Journal of Gastroenterology 51.5(2016):473-486.
International Search Report issued in corresponding International Application No. PCT/CN2019/106064; mailed Dec. 12, 2019; China National Intellectual Administration, Beijing, China, 8 pgs.
Written Opinion issued in corresponding International Application; PCT/CN2019/106064; mailed Dec. 12, 2019; China National Intellectual Administration, Beijing, China, 9 pgs.

* cited by examiner

*Primary Examiner* — Nianxiang Zou
(74) *Attorney, Agent, or Firm* — HAUPTMAN HAM, LLP

(57) ABSTRACT

The present invention provides a kit for early screening of hepatocellular carcinoma, comprising a gene marker detection reagent and a protein marker detection reagent. The invention also provides a preparation method and application of the kit. The kit comprising specific gene markers and protein markers of the present invention has been demonstrated to be effective in achieving early screening of HCC in community populations, particularly in prospective studies.

7 Claims, 7 Drawing Sheets

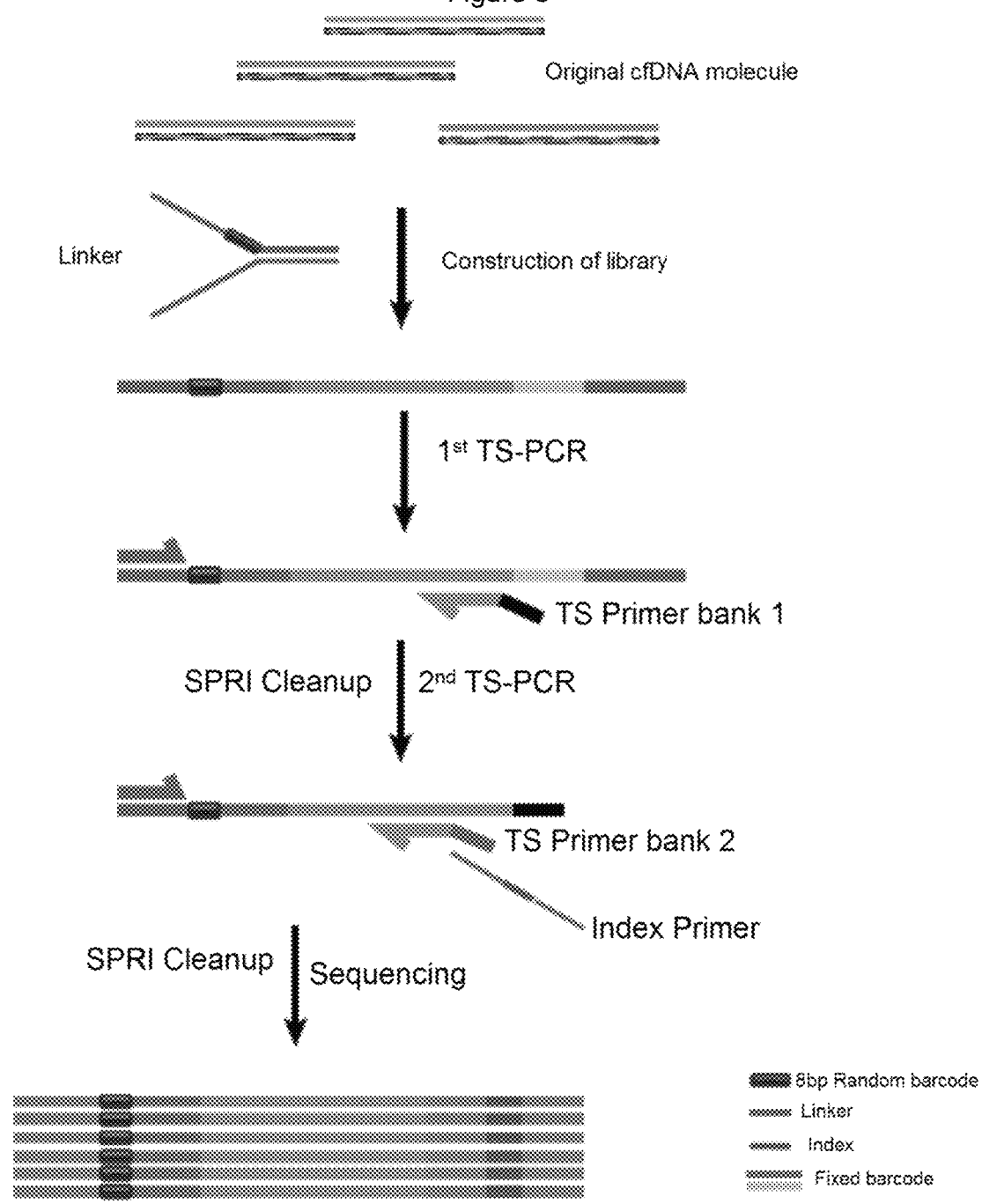

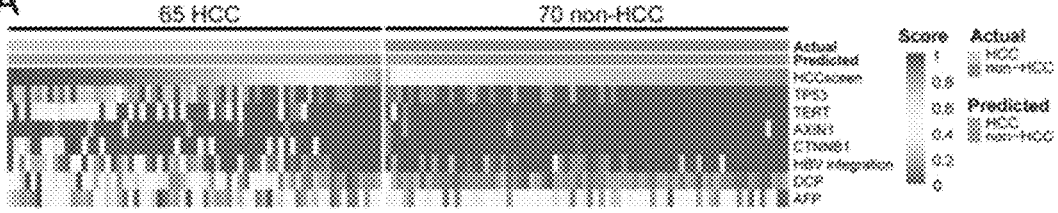
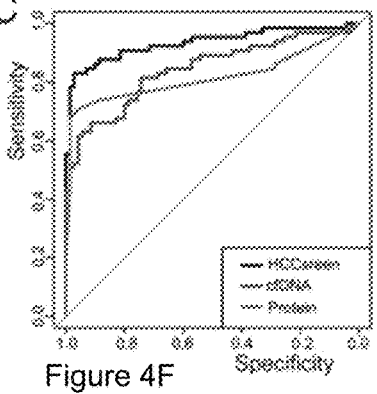
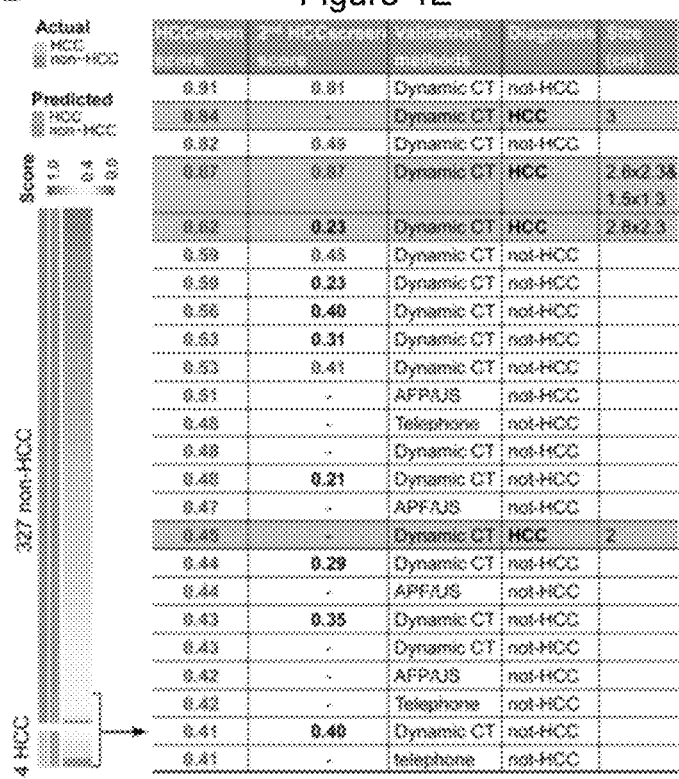
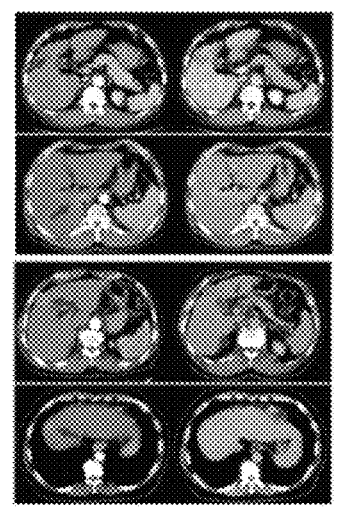
Figure 4A
Figure 4B
Figure 4C
Figure 4D
Figure 4E
Figure 4F
Figure 4G

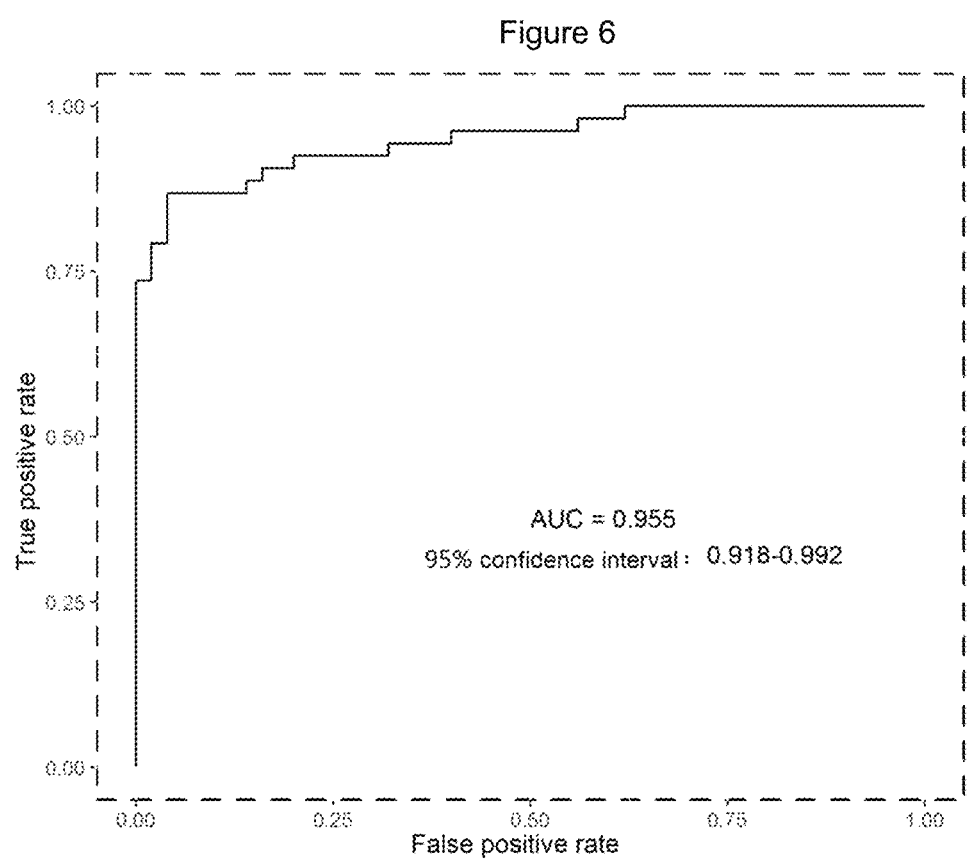

KIT FOR EARLY SCREENING OF LIVER CELL CANCER AND PREPARATION METHOD AND USE THEREOF

RELATED APPLICATIONS

The present application is a U.S. National Phase of International Application Number PCT/CN2019/106064 filed Sep. 17, 2019 and claims priority to Chinese Application Number 201910179499.X filed Mar. 11, 2019.

TECHNICAL FIELD

The invention belongs to the medical field, and relates to a kit for early screening of hepatocellular carcinoma, and more specifically to a kit for early screening of hepatocellular carcinoma of AFP-negative subjects, and a preparation method and application.

BACKGROUND ART

Liver cancer includes two major histopathological types, hepatocellular carcinoma (HCC) and intrahepatic cholangiocarcinoma (iCCA), of which HCC accounts for about 85-90%. Currently, there is no effective treatment for advanced HCC. Therefore, it is recommended that cirrhosis patients at high risk of HCC be screened. (Omata M, et al. (2017) Asia-Pacific clinical practice guidelines on the management of hepatocellular carcinoma: a 2017 update. *Hepatol Int* 11(4):317-370; Marrero J A, et al. (2018) Diagnosis, Staging and Management of Hepatocellular Carcinoma: 2018 Practice Guidance by the American Association for the Study of Liver Diseases. *Hepatology*.). In China, according to the guidelines of the Asian Pacific Association for the Study of the Liver (APASL), early screening for HCC has been conducted in a number of cohorts, recommending that individuals with liver cirrhosis and hepatitis B surface antigen (HBsAg) positive be monitored for HCC every 6 months, including ultrasound (US) and serum alpha-fetoprotein (AFP) detecting (Omata M, et al. (2017), ibid.). In previous studies, early detection and early treatment with this model significantly improved the overall survival rate of liver cancer (Singal A G, Pillai A, & Tiro J (2014) Early detection, curative treatment, and survival rates for hepatocellular carcinoma surveillance in patients with cirrhosis: a meta-analysis. *PLoS medicine* 11(4):e1001624.), but the accurate detection of HCC requires experienced experts, which limits its wide application in all HBsAg positive individuals. In addition, the biannual screening was also associated with follow-up appointments and anxiety. At present, most HCC cases in China are diagnosed based on clinical symptoms rather than by HCC screening, and are at an advanced stage at the time of hospital diagnosis.

In recent studies, liquid biopsies based on gene changes in cell free DNA (cfDNA) have shown good results in early detection of cancer (Bettegowda C, et al. (2014) Detection of circulating tumor DNA in early- and late-stage human malignancies. *Science translational medicine* 6(224): 224ra224; Chaudhuri A A, et al. (2017) Early Detection of Molecular Residual Disease in Localized Lung Cancer by Circulating Tumor DNA Profiling. *Cancer discovery* 7(12): 1394-1403.). Combining genes with protein markers may further improve the sensitivity and specificity of detection and may screen multiple tumor types in one assay (Springer S, et al. (2015) A Combination of Molecular Markers and Clinical Features Improve the Classification of Pancreatic Cysts. Gastroenterology; Cohen J D, et al. (2018) Detection and localization of surgically resectable cancers with a multi-analyte blood test. *Science* 359(6378):926-930; Cohen J D, et al. (2017) Combined circulating tumor DNA and protein biomarker-based liquid biopsy for the earlier detection of pancreatic cancers. *Proceedings of the National Academy of Sciences of the United States of America* 114 (38):10202-10207.). However, these studies were primarily directed to HCC inpatients and healthy people without HBV infection (Cohen J D, et al. (2018), ibid). In high risk groups of chronic HBV infection, the performance of liquid biopsy tests may be affected, because some precancerous lesions, such as cirrhosis, may also have driver mutations common in HCC. Analysis of hepatitis, cirrhosis and non-cancerous liver nodules may be necessary to draw a baseline to accurately identify HCC by imaging or histological clinical validation.

The common causes of liver dysfunction are infection (e.g., hepatitis B virus infection), obesity, alcohol abuse, aflatoxin exposure, dyslipidemia, etc., and liver disease patients are at a higher risk for liver cancer. Alpha-fetoprotein (AFP), des-gamma-carboxy prothrombin (DCP) and squamous cell carcinoma antigen (SCCA) are all protein markers of liver cancer. Researches have shown that the combined measurement of AFP and DCP can improve the sensitivity of predicting liver cancer and distinguish early liver cancer from decompensated cirrhosis. However, AFP, DCP and SCCA were negative in many early liver cancers.

Tumors or other cells release DNA molecules into the blood, which form cell free DNA fragments (cfDNA) after degradation. The detection of cfDNA has great potential in guiding tumor targeting drugs, monitoring efficacy and early screening of cancer. About 90% of liver cancer patients in China have hepatitis B virus infection background, and hepatitis B virus-related liver cancer has almost no KRAS, BRAF and other hotspot mutations.

As previously described, a separate protein marker such as AFP has been used in the past as an early screening indicator for HCC. Chun et al., 2015 (Chun S, Rhie S Y, Ki C S, Kim J E, & Park H D (2015) Evaluation of alpha-fetoprotein as a screening marker for hepatocellular carcinoma in hepatitis prevalent areas. *Annals of hepatology* 14(6):882-888.) reported the use of a single alpha-fetoprotein as a screening marker, but the effect was not satisfactory, with a positive predictive value of about 1-2%.

Recently, attempts have been made for HCC early screening by combining gene changes with protein markers. Joshua D. Cohen et al., 2018 (Cohen J D, Li L, Wang Y, et al. Detection and localization of surgically resectable cancers with a multi-analyte blood test[J]. *Science, 2018*, 359 (6378): eaar3247.) reported early screening of pan-cancerous species, including HCC, using gene mutation binding protein markers, but which did not use gene changes such as TERT and various forms thereof and/or HBV fusions in relation to HCC. And this study was only a retrospective study of inpatients and healthy people who had been diagnosed as HCC, but not a prospective study of patients without HCC symptoms, therefore was not able to predict the occurrence of HCC and give a positive predictive value.

SUMMARY OF THE INVENTION

Traditionally, gene changes or protein markers have each been used alone in cancer early screening. Early screening for cancer by using a combination of gene changes and protein markers has also been attempted. Liquid biopsies that bind cell free DNA (cfDNA) and proteins have shown potential in early cancer detection in a variety of tissue types. However, most of these studies are retrospective, with individuals previously diagnosed with cancer as cases and healthy individuals as controls. Even for a few prospective studies, the markers used in the prior art are poorly predictive of hepatocellular carcinoma. Here, the present invention develops a liquid biopsy assay called hepatocellular carcinoma screening (HCC screening), combines specific gene markers with protein markers, and demonstrates its application value in early HCC detection of chronic HBV infection in a multicenter community population. Verification results show that the method robustly distinguishes HCC individuals from non-HCC individuals, with 85% sensitivity and 93% specificity. The inventors further conducted a prospective study to apply this assay to 331 individuals with normal liver ultrasonography and serum AFP levels. 24 positive cases were identified and 4 cases were confirmed to develop HCC after 6-8 months of clinical follow-up. During the same time range of follow-up, 307 test-negative individuals were not diagnosed with HCC. The assay showed 100% sensitivity, 94% specificity and 17% positive predictive value in the validation set. The positive predictive value (PPV) of 17% was significantly higher than that previously obtained by AFP horizontal screening alone, (Chun S, Rhie S Y, Ki C S, Kim J E, & Park H D (2015) Evaluation of alpha-fetoprotein as a screening marker for hepatocellular carcinoma in hepatitis prevalent areas. *Annals of hepatology* 14(6):882-888.) and higher than that obtained by using specific gene markers and specific protein markers in the invention, respectively.

The kit comprising a specific gene marker and a protein marker of the present invention has been shown to be effective in achieving early screening of HCC in a non-specific population, and thus can be used for early screening of HCC in a non-specific population, and more preferably for early screening of HCC in AFP negative subjects.

It is noteworthy that the kit of the present invention is used for prospective early HCC prediction, and each of the 4 cases of HCC is diagnosed in the early stage (<3 cm), which provides a good basis for follow-up treatment. The inventors' research evidence suggests that the joint detection of cfDNA changes and protein markers is a feasible method to identify early HCC from asymptomatic community groups with unknown HCC status.

Accordingly, in one aspect, the present invention provides a kit for early screening for hepatocellular carcinoma, comprising a gene marker detection reagent and a protein marker detection reagent.

The kit may further comprise a data processing system for converting the information of the gene marker and/or the protein marker into a hepatocellular carcinoma screening score of the person to be detected, and for predicting whether the person to be detected is a liver cancer patient or not according to the hepatocellular carcinoma screening score of the person to be detected.

In another aspect, the present invention provides a method for early screening for hepatocellular carcinoma, comprising:

(1) detecting gene markers and protein markers of a subject by using gene marker detection reagents and protein marker detection reagents; and (2) calculating the hepatocellular carcinoma screening score by using the detection results of the gene markers and the protein markers and comparing with a threshold value.

According to the method, the hepatocellular carcinoma screening score and the threshold value are obtained through a liver cancer prediction model; the method for constructing the prediction model of liver cancer comprises the following steps:

constructing a training set, wherein the training set consists of a plurality of liver cancer patients and a plurality of patients at high risk of liver cancer;

taking gene markers and protein markers of a training set as characteristics, converting detection results into characteristic scores, constructing a liver cancer prediction model by using a penalty logistic regression algorithm, and calculating a hepatocellular carcinoma screening score;

and obtaining a ROC curve of sensitivity and specificity of the penalty logistic regression model according to the hepatocellular carcinoma screening score and the sample grouping information, and determining a cut-off value according to the ROC curve, wherein the cut-off value serves as a threshold value for distinguishing liver cancer patients from patients at high risk of liver cancer.

In yet another aspect, the invention provides the use of gene marker detection reagents and protein marker detection reagents for early screening of hepatocellular carcinoma.

In yet another aspect, the invention provides the use of gene marker detection reagents and protein marker detection reagents in the preparation of a kit for early screening of hepatocellular carcinoma.

The invention aims to perform early liver cancer screening.

The invention firstly protects a liver cancer early screening kit, which can include detection reagents of liver cancer mutant gene, a DCP detection reagent and an AFP detection reagent.

The "detection reagents for the liver cancer mutant gene" can be used for detecting the mutation type and/or the mutation reads and/or the gene copy number variation of the liver cancer mutant gene in the cfDNA.

The "liver cancer mutant gene" may be a TP53 gene and/or a TERT gene and/or an AXIN1 gene and/or a CTNNB1 gene.

The DCP detection reagent can be used for detecting the DCP content in plasma.

The AFP detection reagent can be used for detecting AFP content in plasma.

The kit may also include a detection reagent for whether HBV is integrated with the gene and/or a cfDNA detection reagent.

The "detection reagent for whether the HBV is integrated with the gene" can be used for detecting whether an integration sites of HBV sequence and human genome exits in cfDNA.

The "cfDNA detection reagent" can be used to detect the concentration of cfDNA and/or the percentage of different insert fragment lengths of cfDNA to the cfDNA content.

The kit of any of the above may further comprise a data processing system; the data processing system is used for converting liver cancer gene variation information (i.e. information about 11 gene mutation characteristics), DCP content (DCP content in plasma), AFP content (AFP content in plasma), whether HBV is integrated with genes, cfDNA information and clinical information of a subject into a hepatocellular carcinoma screening score (i.e. an HCCscreen score value) of the subject; and for predicting whether the person to be detected is a liver cancer patient or not according to the hepatocellular carcinoma screening score of the person to be detected.

The invention also protects the application of the detection reagents of the liver cancer mutant gene, the DCP detection reagent, the AFP detection reagent, the detection reagent of whether the HBV is integrated with the gene or not and the cfDNA detection reagent, which can be at least one of A1)-A4):

A1) predicting whether a person to be detected is a liver cancer patient;
A2) preparing a kit for predicting whether a person to be detected is a liver cancer patient;
A3) predicting liver cancer;
A4) preparing a kit for predicting liver cancer.

The invention also protects the application of the detection reagents of the liver cancer mutant gene, the DCP detection reagent, the AFP detection reagent, the detection reagent of whether the HBV is integrated with the gene or not, the cfDNA detection reagent and the data processing system, which can be at least one of A1)-A4):

A1) predicting whether a person to be detected is a liver cancer patient;
A2) preparing a kit for predicting whether a person to be detected is a liver cancer patient;
A3) predicting liver cancer;
A4) preparing a kit for predicting liver cancer.

The invention also protects the age, sex, the content of DCP in the blood plasma, the content of AFP in the blood plasma of the person to be detected and "the mutation type, mutation reads, gene copy number variation of a liver cancer mutant gene, whether HBV is integrated with the gene, the concentration of the cfDNA and the percentage of different insert fragment lengths of cfDNA to the cfDNA content of the person to be detected" as a marker application, which can be at least one of A1)-A4):

A1) predicting whether a person to be detected is a liver cancer patient;
A2) preparing a kit for predicting whether a person to be detected is a liver cancer patient;
A3) predicting liver cancer;
A4) preparing a kit for predicting liver cancer.

The invention also provides a method for predicting liver cancer, which can comprise the following steps of: detecting the content of DCP and AFP in the blood plasma of a person to be detected; detecting the mutation type, mutation reads, gene copy number variation of liver cancer mutant genes, whether HBV is integrated with the gene, the concentration of the cfDNA and the percentage of different insert fragment lengths of cfDNA to the cfDNA content of the person to be detected; recording the age and sex of a person to be detected; converting the information of the person to be detected into a hepatocellular carcinoma screening score (i.e. an HCCscreen score value), and predicting whether the person to be detected is a liver cancer patient or not according to the hepatocellular carcinoma screening score.

"Predicting whether the person to be detected is a liver cancer patient or not according to the hepatocellular carcinoma screening score" comprises determining a diagnosis threshold value through a working characteristic curve (ROC curve), comparing the hepatocellular carcinoma screening score of the person to be detected with the size of the diagnosis threshold value, and finishing the liver cancer prediction of the person to be detected.

The HCCscreen score of the person to be detected can be calculated by a liver cancer prediction model. The liver cancer prediction model is a penalty logistic regression model developed according to the characteristic scores and grouping information of each patient in the training set. The training set consists of a plurality of liver cancer patients (constituting a liver cancer group) and a plurality of liver cancer high-risk patients (constituting a liver cancer high-risk group). In one embodiment of the present invention, the training set consists of 65 liver cancer patients and 70 high-risk liver cancer patients.

Whether the HBV is integrated with the gene or not can be as follows: the extent to which HBV is integrated with a gene, whether HBV is integrated with a TERT gene and/or whether HBV is integrated with a non-TERT gene (e.g., APOBEC4, FBX010, FUT8, WDR7, SLC7A10, GUSBP4).

Information of the liver cancer mutant gene of any one of the above includes information of the mutation type and/or mutation reads and/or gene copy number variation of the liver cancer mutant gene.

The cfDNA information described above may include cfDNA concentration and/or the percentage of different insert fragment lengths of cfDNA to the cfDNA content. The percentage of cfDNA content of different insertion fragment length of the cfDNA can be specifically as follows: interval percentage of cell free DNA fragment length less than 90 bp, interval percentage of cell free DNA fragment 90-140 bp, interval percentage of cell free DNA fragment 141-200 bp and interval percentage of cell free DNA fragment greater than 200 bp. Interval percentage refers to the percentage of all cfDNA content.

The clinical information of any of the above may include age and/or sex.

The detection reagents of the liver cancer mutant gene comprise a reagent for extracting cfDNA (such as a MagMAX™ Cell-Free DNA Isolation Kit), a reagent for constructing a cfDNA library (such as a KAPA Hyper Prep kit), and a reagent for performing hybridization capture of a target region (such as a sureselect XT target capture kit).

The DCP detection reagent can be a reagent for detecting the content of DCP in plasma. Specifically: separating plasma and detecting DCP by American Abbott ARCHITECT i2000SR chemiluminescence immuno-analyzer.

The AFP detection reagent may be a reagent for detecting AFP content in plasma. Specifically: separating plasma and detecting AFP by American Abbott IMx analyzer.

The detection reagent for whether or not the HBV is integrated with the gene may include a reagent for extracting cfDNA (e.g., MagMAX™ Cell-Free DNA Isolation Kit).

The cfDNA detection reagent includes a reagent for extracting cfDNA (e.g., MagMAX™ Cell-Free DNA Isolation Kit).

In the above, the characteristics of the detection (kit detection) can be specifically 20 characteristics in the embodiment as follows:

I. The characteristics used by the "detection reagents for the liver cancer mutant gene" can specifically be 11 characteristics in the embodiment, which are a TP53 gene non-R249S mutation, a TERT gene mutation, an AXIN1 gene mutation, a CTNNB1 gene mutation, a TP53 R249S hot spot mutation, a CNV dimensionality reduction characteristic 1, a CNV dimensionality reduction characteristic 2, a CNV dimensionality reduction characteristic 3, a CNV dimensionality reduction characteristic 4, a CNV dimensionality reduction characteristic 5 and a CNV dimensionality reduction characteristics 6 (i.e. 11 gene mutation characteristics), respectively. The specific steps are as follows:

1. Extracting cfDNA of blood sample to be detected.
2. Taking the cfDNA of the blood sample to be detected, and constructing a library by using a KAPA Hyper Prep kit to obtain the cfDNA library of the blood sample to be detected.

3. Taking a cfDNA library of the blood sample to be detected, performing hybridization capture of target region by using a sureselect XT target capture kit, and sequencing on an Illumina platform. Obtaining a detection result (including mutant gene and mutation frequency) of the liver cancer mutant gene in the cfDNA of the blood sample to be detected.

4. Annotating and scoring of gene mutation results

Annotating the detection result of the liver cancer mutant gene in the cfDNA: annotation score for mutation reads support frequency.

5 Taking a cfDNA library of a blood sample to be detected, performing low-depth whole genome sequencing, and then performing CNV detection and cfDNA fragment length detection on sequencing data.

6. Feature extraction of gene copy number variation detection results

The CNV detection results are processed as follows: principal component analysis (PCA) dimensionality reduction is performed on the CNV signals (the sex chromosomes were deleted to rule out the effect of gender on CNV signal) at each chromosome arm level, with the cumulative ratio (cumulative proportion) ≥95% as the threshold, the first six principal components (CNV dimensionality reduction characteristic 1, CNV dimensionality reduction characteristic 2, CNV dimensionality reduction characteristic 3, CNV dimensionality reduction characteristic 4, CNV dimensionality reduction characteristic 5, CNV dimensionality reduction characteristic 6) are selected as CNV related characteristics, the CNV dimensionality reduction characteristic 1, CNV dimensionality reduction characteristic 2, CNV dimensionality reduction characteristic 3, CNV dimensionality reduction characteristic 4, CNV dimensionality reduction characteristic 5, CNV dimensionality reduction characteristic 6) are as CNV characteristics for subsequent calculation, and the corresponding principal component score of each CNV characteristic is the characteristic score of the characteristic.

7. Detecting cfDNA fragment length

The low-depth whole genome sequencing data can be used to analyze the four characteristics in the examples, which can be interval percentage of cell free DNA fragment length less than 90 bp, interval percentage of cell free DNA fragment 90-140 bp, interval percentage of cell free DNA fragment 141-200 bp and interval percentage of cell free DNA fragment greater than 200 bp, respectively.

II. The characteristics used by the "cfDNA detection reagent" for detection specifically be the concentration of cfDNA. The cfDNA concentration values were taken as characteristic scores after log 2 transformation.

III. The characteristics used by the "DCP detection reagent" may be specifically one characteristics in the examples, that is, the DCP content in plasma.

IV. The characteristics used by the "AFP detection reagent" can be specifically one characteristics in the examples, that is, the AFP content in plasma.

V. The characteristics used by the "whether the HBV is integrated with the gene or not" can be specifically two characteristics in the example, namely the situation of integration variation of the HBV and whether the HBV is integrated with the TERT or not (i.e. two gene mutation characteristics).

In the above, mutation site integration and scoring: for each gene mutation, giving an annotation score according to the mutation reads support frequency; the mutation site scores are then accumulated into different ROI (Region Of Interest) intervals (i.e., obtaining characteristic scores). The interval includes four genes (TP53, CTNNB1, TERT and AXIN1) and a TP53 R249S hotspot mutation site region. The calculation formula is as follows:

$$ROI = \log2 \sum_{i=1}^{n} \text{adj\_score}_i$$

Where n is the number of mutations overlapping the ROI and adj_score is the reads support frequency of the mutation.

In the above, the structural variation result characteristic extraction steps are as follows:

(1) Detecting the characteristic score of HBV integration variation in each sample: for each integration mutation detected, it was divided into three grades A, B and C according to the reads support credibility (the number of integrated reads ≥10, grade A; 10>the number of integrated reads >6, grade B; the rest was grade C, as shown in column 3 of Table 7), and the corresponding scores were 1, 0.8 and 0.3 respectively, and then summed up to obtain the characteristic score of HBV integration variation.

(2) Detecting the score of the HBV and TERT integration variation characteristic of each sample: TERT integration occurs, and the characteristic score of TERT integration variation is 1 (without considering reads support credibility rating); TERT integration did not occur, and the characteristic score of TERT integration variation was 0.

In the above, the related characteristic extraction steps of the cell free DNA length are as follows: calculating the percentage of the length of the cfDNA fragment in four intervals (<90 bp, 90-140 bp, 141-200 bp and >200 bp), taking the characteristics as prediction variables, the percentage of the length of the cfDNA fragment in the four intervals is a characteristic score.

In the above, the related characteristic extraction of the protein marker comprises the following steps of:

Dividing actual measured values of AFP into five numerical levels from low to high according to threshold values (13, 20, 200, 400): 0, 5, 8, 20 and 30, dividing actual measured values of the DCP into three numerical levels from low to high according to threshold values (40 and 60): 0, 2, 5 as characteristic scores of two protein markers.

In addition, two characteristics can be extracted according to clinical and experimental correlation characteristics, and the clinical characteristics include age and gender of patients, and also have a certain correlation with case phenotype. Wherein, the characteristic value of the age is the actual age value of the sample; The characteristic score of male is 1, and that of female is 0.

The characteristics may include the following 22 characteristics: 13 gene mutation characteristics, 2 protein markers, 5 cfDNA physical characteristics and the basic information composition of 2 blood sample. The 13 gene mutations characteristics are a TP53 gene non-R249S mutation, a TERT gene mutation, an AXIN1 gene mutation, a CTNNB1 gene mutation, a TP53 R249S hot spot mutation, a CNV dimensionality reduction characteristic 1, a CNV dimensionality reduction characteristic 2, a CNV dimensionality reduction characteristic 3, a CNV dimensionality reduction characteristic 4, a CNV dimensionality reduction characteristic 5 and a CNV dimensionality reduction characteristics 6, HBV integrated variation, whether HBV and TERT integrated variation, respectively. The two protein markers were AFP and DCP, respectively. The five physical characteristics of cfDNA were as follows interval percentage of cell free DNA fragment length less than 90 bp, interval percentage of cell free DNA fragment 90-140 bp, interval percentage of cell free DNA fragment 141-200 bp, interval percentage of cell free DNA fragment greater than 200 bp and the concentration of cfDNA respectively concentration. The basic information of 2 blood sample is sex and age, respectively.

Early detection of cancer is the most effective way to reduce cancer-induced death. In recent studies, cfDNA and/or protein-based liquid biopsies have shown promise in early detection of cancer in a variety of tissue types (Cohen J D, et al. (2018), ibid), but have not demonstrated good predictive results for HCC, nor have they demonstrated efficacy in identifying early liver cancer and high-risk populations. In this study, the inventors developed and tested a liquid biopsy assay. In the selection of biomarkers, we focus on frequently changing genetic biomarkers with clear carcinogenic mechanisms, such as TERT promoter mutations, and protein markers with definite diagnostic value, such as DCP (Lok A S, et al. (2010) Des-gamma-carboxy prothrombin and alpha-fetoprotein as biomarkers for the early detection of hepatocellular carcinoma. *Gastroenterology* 138(2): 493-502.). The present invention comprises a limited number of candidate biomarkers specifically associated with HCC, and to avoid over-fitting effects when studying a large number of candidate biomarkers in a limited number of tumor/normal cases, we incorporate a small number of candidate biomarkers specifically associated with HCC. By using research tools for retrospective and/or prospective studies to verify a particular combination of gene markers and protein markers selected according to the present invention, it has been found that this particular combination achieves superior results in both retrospective and prospective verification.

Accordingly, in one aspect, the present invention provides a kit for the early screening of hepatocellular carcinoma in AFP negative subjects, comprising gene marker detection reagents and a DCP detection reagent.

The kit may further comprise a data processing system for converting the information of the gene markers and/or the protein markers into a hepatocellular carcinoma screening score of the person to be detected, and for predicting whether the person to be detected is a liver cancer patient or not according to the hepatocellular carcinoma screening score of the person to be detected.

The gene marker detection reagents of any one of the above may comprise one or more, preferably three or four, selected from: TP53 detection reagent, CTNNB1 detection reagent, AXIN1 detection reagent, TERT detection reagent.

The gene marker detection reagents of any one of the above may further comprise a detection reagent for whether HBV is integrated with a gene.

The protein marker detection reagents of any one of the above may comprise one or more selected from: AFP detection reagent and DCP detection reagent.

The kit of the present invention can be used for early screening of HCC in non-specific populations, as well as for early screening of HCC in specific populations such as AFP negative subjects. Since AFP is a common test indicator in routine physical examinations such as blood tests, it is likely that the subject's AFP status (negative or positive) is known. Thus, in some embodiments, the kit of the present invention is an HCC early screen for a particular population, such as AFP negative subjects, wherein the kit does not include an AFP detection reagent. Similarly, in some embodiments, the kit of the present invention is an HCC early screen for a particular population, such as DCP negative subjects, wherein the kit does not include an DCP detection reagent. Similarly, in some embodiments, the kit of the present invention is an HCC early screen for a particular population such as AFP and DCP negative subjects, wherein the kit does not include an AFP detection reagent and a DCP detection reagent. Thus in some embodiments, the present invention provides a kit for the early screening of hepatocellular carcinoma in AFP negative subjects comprising a gene marker detection reagent and a protein marker detection reagent, preferably wherein the protein marker detection reagent comprises a DCP detection reagent. In some embodiments, the present invention provides a kit for screening hepatocellular carcinoma in a DCP negative subject comprising a gene marker detection reagent and a protein marker detection reagent, preferably wherein the protein marker detection reagent comprises an AFP detection reagent. In some embodiments, the present invention provides a kit for the early screening of hepatocellular carcinoma in AFP and DCP negative subjects comprising a gene marker detection reagent. The gene marker detection reagents according to the present invention can detect the presence and/or type of gene markers, including mutant types and mutant reads.

Gene marker detection reagents according to the present invention also include CNV detection reagents in some embodiments. The CNV detection reagent is typically used to detect CNV at the whole genome level, but in some embodiments may also be used to detect at local levels, such as CNV of genes. In some embodiments, a kit of the invention comprises a CNV detection reagent for detecting global CNV levels. In some embodiments, a kit of the invention comprises a CNV detection reagent for detecting local CNV levels. In some embodiments, a kit of the invention comprises a CNV detection reagent for detecting CNV level of a TERT gene. The use of CNV detection reagents may further improve the sensitivity and specificity of HCC screening. In some embodiments, the CNV detection result may be converted to CNV dimensionality reduction characteristic 1, CNV dimensionality reduction characteristic 2, CNV dimensionality reduction characteristic 3, CNV dimensionality reduction characteristic 4, CNV dimensionality reduction characteristic 5, and/or CNV dimensionality reduction characteristic 6.

As used herein, the term "gene marker detection reagents" are detection reagents for detecting gene markers, including those well known to those skilled in the art and described herein. Accordingly, the terms "TP53 detection reagent", "CTNNB1 detection reagent", "AXIN1 detection reagent" and "TERT detection reagent" are detection reagents for detecting the respective specified gene markers, including those well known to those skilled in the art and described herein. TP53, CTNNB1, AXIN1 and TERT are well known to those skilled in the art as common gene markers in the art, such as TERT promoter mutations. In some embodiments, the full length of TP53 is detected. In some embodiments, one or more exons of TP53 are detected. The invention is characterized in some aspects by detecting the full length of TP53, rather than detecting only one or more exons of TP53.

Those skilled in the art will readily recognize that a gene of the present invention, when used as a gene marker, utilizes at least one or more nucleotide differences between all or a portion of the sequence obtained by sequencing and its corresponding wild-type sequence, and is not necessarily limited to a particular site. The TP53, CTNNB1, AXIN1 and TERT genes, when used as gene markers, may differ in length from their corresponding wild-type sequences by at least one or more nucleotides. The TP53 gene, when used as a gene marker, may also differ in its particular hotspot (e.g., R249S) from its corresponding wild-type sequence by at least one or more nucleotides. The TERT gene, when used as a gene marker, may also differ in its particular hotspot (e.g., chr5:1295228C>T or chr5:1295250C>T) from its corresponding wild-type sequence by at least one or more nucleotides.

Gene marker detection reagents according to the present invention also include HBV integration detection reagents in some embodiments. As used herein, the term "HBV integration detection reagent" is an agent used to detect whether HBV is integrated into the genome. In some embodiments, HBV integration in the genome may include HBV integration near TERT in the genome, e.g., within 1.5 kb upstream of TERT, and HBV integration elsewhere in the genome.

In some embodiments, the subject's gene marker is detected from the subject's cfDNA. In general, when gene markers are detected by using the gene marker detection reagents described herein, the use process or detection process includes cfDNA extraction and detection, from which information related to the cfDNA is known, including, for example, cfDNA concentration and/or the percentage of different insert fragment lengths of cfDNA to the cfDNA content and/or cfDNA length detection reagents. Thus, in some embodiments, the "gene marker detection reagent" and its hyponyms described herein may also function as a cfDNA detection reagent and thus be used interchangeably with the "cfDNA detection reagent". In other embodiments, the kit of the invention further comprises a cfDNA detection reagent.

As used herein, the term "protein marker detection reagent" is a detection reagent for detecting protein markers, including those well known to those skilled in the art and described herein. Accordingly, the terms "AFP detection reagent" and "DCP detection reagent" are detection reagents for detecting the respective specified protein markers, including those well known to those skilled in the art and described herein. AFP and DCP are well known to those skilled in the art as common protein markers in the art.

In some embodiments, the subject's protein marker is detected from the subject's blood or a component thereof, such as serum or plasma. In some embodiments, the kit further comprises a blood collection set.

The kit of the present invention may also include or be used in conjunction with a data processing system, which may be included in a computer, for example. The data processing system is used for processing detection results of the gene marker detection reagent and/or the protein marker detection reagent according to the present invention. In some embodiments, the data processing system uses the detection results of the gene markers and protein markers to calculate a hepatocellular carcinoma screening score. In some embodiments, the data processing system compares the hepatocellular carcinoma screening score to a threshold. In some embodiments, the data processing system is used to estimate and/or verify and/or predict HCC, preferably by comparing the hepatocellular carcinoma screening score to a threshold.

Using this HCC screening, the present invention finds it possible to identify early HCC individuals and distinguish them from non-HCC individuals with chronic liver disease, including cirrhosis. The assay showed 85% sensitivity and 93% specificity in the diagnosis of HCC in individuals with elevated liver nodules and/or serum AFP detected by ultrasound. More importantly, performance was also maintained in the AFP/US negative validation set with sensitivity and specificity of 100% and 94%, respectively. Current sensitivity is based on a limited number of HCC cases. If additional HCC cases are identified, this may vary with long term follow-up or dynamic CT/MRI examination of all individuals. In this case, determination of sensitivity and specificity based on follow-up time requires prospective and large-scale clinical trials. However, 17% of the current positive predictive value (PPV) in the validation set was significantly higher than previously obtained with AFP level screening alone (Chun S, Rhie S Y, Ki C S, Kim J E, & Park H D (2015) Evaluation of alpha-fetoprotein as a screening marker for hepatocellular carcinoma in hepatitis prevalent areas. *Annals of hepatology* 14(6):882-888.).

Accordingly, in another aspect, the present invention provides a method for early screening for hepatocellular carcinoma, comprising:

(1) detecting gene markers and protein markers of a subject; and (2) calculating the hepatocellular carcinoma screening score by using the detection results of the gene markers and the protein markers and comparing with a threshold value.

PPV can be further improved if a second HCC screening is provided for cases that are positive in the first test. High PPV is very helpful for clinical routine use because it reduces unnecessary anxiety and follow-up in non-HCC individuals.

Accordingly, in another aspect, the present invention provides a method for early screening for hepatocellular carcinoma, comprising:

(1) detecting gene markers and protein markers of a subject;

(2) calculating the hepatocellular carcinoma screening score by using the detection results of the gene markers and the protein markers and comparing with a threshold value; and (3) if the hepatocellular carcinoma screening score is above the threshold, steps (1) and (2) are repeated one or more times for the subject after a period of time.

In one embodiment, the subject's gene marker is detected from the subject's cfDNA. That is, the method includes extracting cfDNA from the subject.

In one embodiment, the subject's protein marker is detected from the subject's blood. That is, the method includes withdrawing blood, preferably serum or plasma, from the subject.

As used herein, the term "a period of time" may be one day, two days, three days, four days, five days, six days, one week, two weeks, three weeks, one month, two months, three months, four months, five months, six months, seven months, eight months, nine months, ten months, eleven months, one year, and is not limited thereto.

In some embodiments, the threshold for comparing with the calculated hepatocellular carcinoma screening score is 0.1, 0.2, 0.3, 0.4, 0.5, 0.6, 0.7, 0.8, 0.9, or 1.0. In a preferred embodiment, the threshold is 0.4. In a preferred embodiment, the threshold is 0.5.

In yet another aspect, the invention provides the use of gene marker detection reagents and protein marker detection reagents for early screening of hepatocellular carcinoma.

In yet another aspect, the invention provides the use of gene marker detection reagents and protein marker detection reagents in the preparation of a kit for early screening of hepatocellular carcinoma.

Those skilled in the art will appreciate that all definitions of the characteristics, parameters, effects, etc. described in the description of the kit herein can be appropriately combined with any other aspects of the method or use of the present invention.

Tumor size is an important clinical parameter in diagnosis, affecting the survival of HCC patients. Unlike protein or RNA-based biomarkers, tumor cells typically contain only one copy of mutant DNA in most cases. One fundamental problem with early detection screening based on cfDNA is whether the early tumor releases enough copies of mutant DNA to be detected in circulation. Of all identified HCC cases screened by HCC in this study, 85% and 68% of cases were <5 cm and <3 cm, respectively. HCC tumors <5 cm are early stage and suitable for curative surgery. Patients with tumors <3 cm may have even better results, emphasizing the value of HCC screening to reduce HCC morbidity and mortality. In the validation set, the present invention identified 4 HCC, 2-3 cm in size, from the AFP/US negative population. These results clearly show that the sensitivity of HCC screening is promising for early HCC detection.

The ideal tumor screening method should have high sensitivity and specificity, and it should also be easy to perform in clinical practice. The present HCC screening assay detects mutations in the coding region and translocation/HBV integration with unknown breakpoints at a cost <150. In addition, the liquid biopsy assay can be centralized and standardized and requires minimal expertise and equipment in local hospitals/clinics. In general, the method is very suitable as a routine test for HCC screening in high-risk populations.

Evidence provided by the present study indicates that cfDNA mutation and protein marker based screening in high-risk populations is effective in identifying HCC patients. It is non-invasive and can detect early and late stage tumors. More importantly, since somatic mutations in driver genes are common in the development of most cancers, this strategy can be modified for early screening of other tumor types or multiple tumor types from single-tube blood.

The kit of the invention may also contain additional therapeutic agents. The method of the invention may further comprise administering an additional therapeutic agent. In one embodiment, the additional therapeutic agent is a cancer (e.g., hepatocellular carcinoma) therapeutic agent known in the art.

Where a series of numerical values is recited herein, it is to be understood that any recited numerical value may be the upper or lower limit of the numerical range. It is also to be understood that the invention encompasses all such numerical ranges, i.e., a range having a combination of an upper numerical limit and a lower numerical limit, wherein each numerical value of the upper and lower numerical limits may be any numerical value recited in the present invention. The scope of the invention provided should be understood to include all values within that range. For example, 1-10 should be understood to include all of the values 1, 2, 3, 4, 5, 6, 7, 8, 9, and 10, and as the case may be, fractional values. Ranges expressed as "up to" a certain value (e.g., up to 5) are to be understood as all values (including the upper limit of the range), e.g., 0, 1, 2, 3, 4, and 5, and as the case may be, fractional values. Up to one week or within one week is understood to include 0.5, 1, 2, 3, 4, 5, 6 or 7 days. Similarly, a range defined by "at least" should be understood to include the lower values provided and all higher values.

Unless otherwise indicated, all percentages are weight/weight.

As used herein, "about" is understood to include within three standard deviations of the mean or within standard tolerances in a particular field. In certain embodiments, about is understood to be a variation of no more than 0.5. "About" modifies all recited values thereafter. For example, "about 1, 2, 3" means "about 1", "about 2", "about 3".

The articles "a" and "an" are used herein to refer to one or more (i.e., at least one) of the grammatical objects of the article. For example, "an element" refers to one element or more than one elements.

The term "comprise" is used herein to refer to the phrase "including, but not limited to", and is used interchangeably therewith.

Unless the context clearly indicates otherwise, the term "or" is used inclusively in the present invention to refer to the term "and/or" and is used interchangeably therewith.

The term "such as" is used herein to refer to the phrase "such as, but not limited to", and is used interchangeably therewith.

It will be appreciated by those skilled in the art that the technical characteristics described above in the various embodiments may be used alone or in combination with the technical solutions of the various aspects of the invention.

Some embodiments of the invention are illustrated by the following non-limiting examples.

The early liver cancer screening markers are mostly protein or gene methylation information. The present invention reports a novel hepatocellular carcinoma screening (HCC screening) method based on the detection of both serum protein markers and changes in cfDNA, and demonstrates its utility in early HCC detection in multicenter community populations with chronic HBV infection. The inventors of the present invention firstly confirmed that gene mutation information of cfDNA in plasma can be used for early HCC prediction through a large number of experiments. According to the invention, a liver cancer prediction model is adopted to score a person to be detected, and whether the person to be detected is a liver cancer patient or not is predicted through a score value, so that the combination of the gene marker and the protein marker disclosed by the invention, which can effectively perform HCC early screening, is verified. Therefore, the detection of cfDNA for early screening, disease tracking, efficacy evaluation, prognosis prediction of liver cancer has important clinical significance.

BRIEF DESCRIPTION OF THE DRAWINGS

FIG. 3 is a design of gene profiling of cfDNA in an HCC screening assay.

FIGS. 4A-4G shows the performance of HCC screening in the training set and validation set. Wherein, FIG. 4A is the contribution of HCC screening scores and cfDNA and protein biomarkers in the training set and in the diagnostic model; FIG. 4B is a binary result of a training centralized diagnosis model; FIG. 4C is an ROC curve of a diagnosis model for HCC screening in a training set; FIG. 4D is HCC screening performance of the diagnosis model in the validation set; FIG. 4E is the follow-up and diagnosis of HCC positive cases in the validation set; FIG. 4F is a binary result of the diagnosis model the validation set; FIG. 4G is dynamic CT imaging of 4 HCC cases detected by HCC screening in AFP/US negative individuals.

FIGS. 5A-5B is a representation of different training sets. Wherein FIG. 5A is a ROC curve of an HCC screening diagnosis model in a training set using a healthy individual without HBV infection as a control; FIG. 5B was trained with HCC and non-HCC individuals (left) and with HCC and healthy individuals (right).

FIG. 6 is a ROC curve of a liver cancer prediction model.

DETAILED DESCRIPTION OF THE INVENTION

Figure 1:
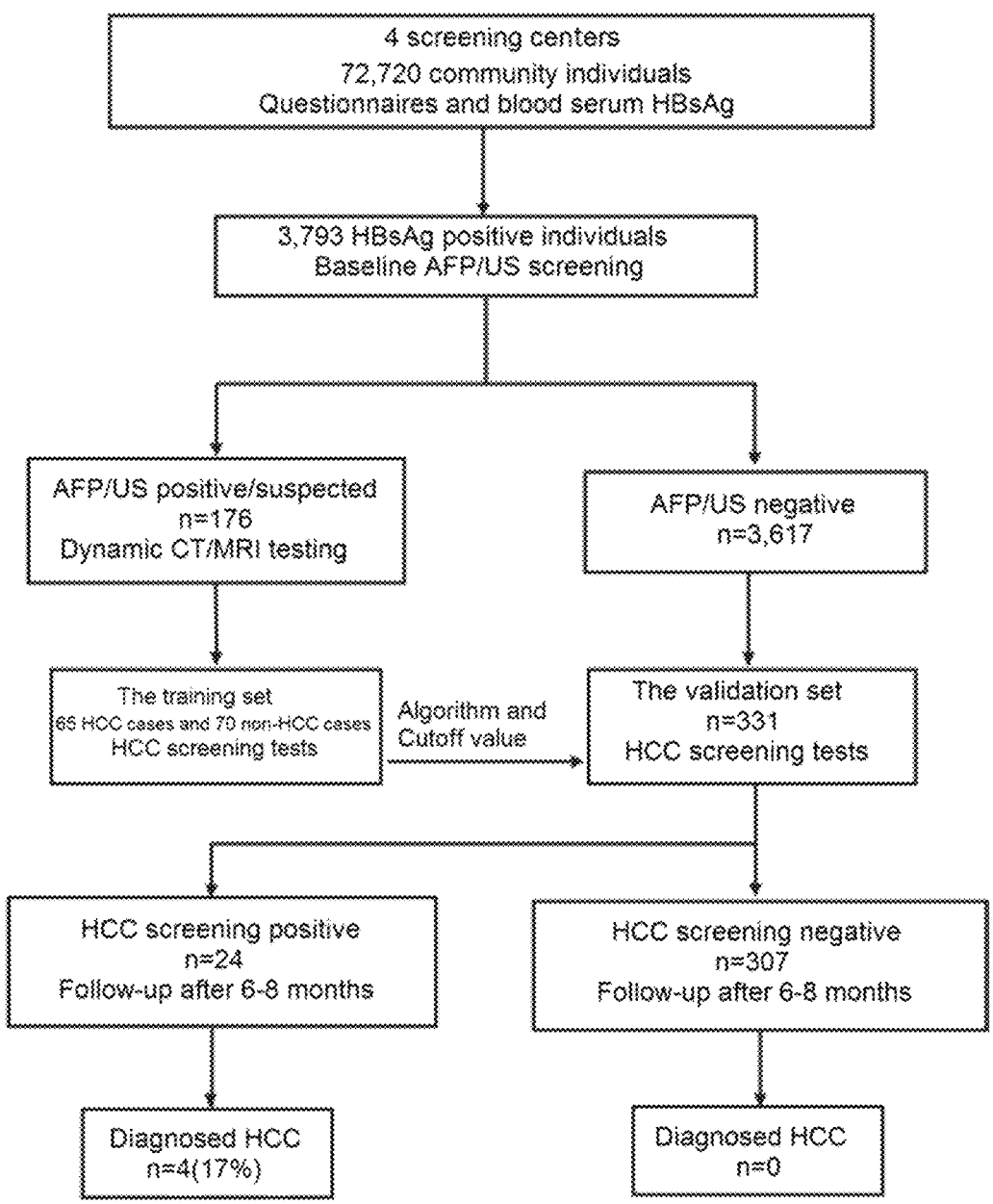
FIG. 1 is a study design protocol. This includes population recruitment, training of HCC screening models, and validation in sampled AFP/US negative individuals.

The following examples facilitate a better understanding of the invention but do not limit it.

The experimental procedures in the following examples, if not specified, are conventional.

The test materials used in the following examples, unless otherwise specified, were purchased from conventional biochemical reagent stores.

The quantitative experiments in the following examples were set up in triplicate and the results averaged.

In the following embodiments, all liver cancer patients, high-risk liver cancer patients and healthy volunteers have informed consent to the content of this study.

MagMAX™ Cell-Free DNA Isolation Kit is a product of Thermo Fisher. The KAPA Hyper Prep kit is a product of KAPA. The sureselect XT target capture kit is a product of Agilent.

In the following examples, the basic information of some liver cancer patients, liver cancer high-risk patients and healthy volunteers is detailed in Table 1.

TABLE 1

| Number | Sex | Age | Diagnosis (CT) | Tumor Size |
|---|---|---|---|---|
| HCCscreen01 | Male | 48 | liver cancer | 1.9 cm × 2.7 cm |
| HCCscreen02 | Male | 56 | liver cancer | 8 cm |
| HCCscreen03 | Male | 75 | liver cancer | 3 cm × 2 cm × 2 cm |
| HCCscreen04 | Male | 58 | liver cancer | 5.0 cm × 3.0 cm |
| HCCscreen05 | Female | 53 | liver cancer | — |
| HCCscreen06 | Male | 63 | liver cancer | 4.1 cm × 3.2 cm |
| HCCscreen07 | Male | 39 | liver cancer | 2.3 cm × 2 cm × 1.8 cm |
| HCCscreen08 | Male | 42 | liver cancer | 3.8 cm × 3.5 cm |
| HCCscreen09 | Male | 56 | liver cancer | 2.3 cm × 2.6 cm |
| HCCscreen10 | Female | 68 | liver cancer | 4.7 cm × 4.2 cm |
| HCCscreen11 | Male | 53 | liver cancer | 2.1 cm × 1.2 cm |
| HCCscreen12 | Male | 69 | liver cancer | 1.2 cm × 1.4 cm |
| HCCscreen13 | Male | 69 | liver cancer | — |
| HCCscreen14 | Male | 60 | liver cancer | 3.2 cm × 2.6 cm |
| HCCscreen15 | Male | 54 | liver cancer | 3.0 cm × 2.5 cm |
| HCCscreen16 | Male | 62 | liver cancer | 3.6 cm × 3.8 cm and 1.4 cm × 1.8 cm |
| HCCscreen17 | Male | 69 | liver cancer | 3.1 cm × 2.2 cm |
| HCCscreen18 | Male | 68 | liver cancer | Multiple, maximum 4.5 cm × 3.0 cm |
| HCCscreen19 | Male | 55 | liver cancer | — |
| HCCscreen20 | Female | 70 | liver cancer | 4.9 cm × 4.4 cm |
| HCCscreen21 | Male | 50 | liver cancer | Multiple, maximum 8.0 cm × 6.5 cm, recurrence after treatment |
| HCCscreen22 | Male | 70 | liver cancer | Multiple, maximum 14.7 cm × 13.0 cm |
| HCCscreen23 | Male | 41 | High risk for liver cancer | — |
| HCCscreen24 | Male | 46 | High risk for liver cancer | — |
| HCCscreen25 | Female | 60 | High risk for liver cancer | — |
| HCCscreen26 | Male | 54 | High risk for liver cancer | — |
| HCCscreen27 | Female | 56 | High risk for liver cancer | — |
| HCCscreen28 | Male | 56 | High risk for liver cancer | — |
| HCCscreen29 | Male | 38 | High risk for liver cancer | — |
| HCCscreen30 | Male | 54 | High risk for liver cancer | — |
| HCCscreen31 | Female | 64 | High risk for liver cancer | — |
| HCCscreen32 | Female | 55 | High risk for liver cancer | — |
| HCCscreen33 | Female | 52 | High risk for liver cancer | — |
| HCCscreen34 | Female | 53 | High risk for liver cancer | — |
| HCCscreen35 | Female | 44 | High risk for liver cancer | — |
| HCCscreen36 | Female | 55 | High risk for liver cancer | — |
| HCCscreen37 | Female | 51 | High risk for liver cancer | — |
| HCCscreen38 | Female | 57 | High risk for liver cancer | — |
| HCCscreen39 | Female | 66 | High risk for liver cancer | — |
| HCCscreen40 | Male | 54 | High risk for liver cancer | — |
| HCCscreen41 | Male | 43 | High risk for liver cancer | — |
| HCCscreen42 | Male | 38 | High risk for liver cancer | — |
| HCCscreen43 | Male | 48 | High risk for liver cancer | — |
| HCCscreen44 | Male | 45 | High risk for liver cancer | — |
| HCCscreen45 | Male | 47 | High risk for liver cancer | — |
| HCCscreen46 | Male | 43 | High risk for liver cancer | — |
| HCCscreen47 | Female | 47 | High risk for liver cancer | — |
| HCCscreen48 | Female | 63 | High risk for liver cancer | — |
| HCCscreen49 | Female | 55 | High risk for liver cancer | — |
| HCCscreen50 | Male | 34 | High risk for liver cancer | — |
| HCCscreen51 | Male | 32 | Healthy volunteer | — |
| HCCscreen52 | Male | 32 | Healthy volunteer | — |
| HCCscreen53 | Male | 34 | Healthy volunteer | — |
| HCCscreen54 | Male | 36 | Healthy volunteer | — |
| HCCscreen55 | Male | 28 | Healthy volunteer | — |
| HCCscreen56 | Female | 24 | Healthy volunteer | — |
| HCCscreen57 | Male | 32 | Healthy volunteer | — |
| HCCscreen58 | Female | 29 | Healthy volunteer | — |
| HCCscreen59 | Female | 32 | Healthy volunteer | — |
| HCCscreen60 | Male | 39 | Healthy volunteer | — |
| HCCscreen61 | Male | 30 | Healthy volunteer | — |
| HCCscreen62 | Female | 22 | Healthy volunteer | — |
| HCCscreen63 | Male | 29 | Healthy volunteer | — |
| HCCscreen64 | Female | 36 | Healthy volunteer | — |
| HCCscreen65 | Female | 33 | Healthy volunteer | — |
| HCCscreen66 | Male | 28 | Healthy volunteer | — |
| HCCscreen67 | Female | 24 | Healthy volunteer | — |
| HCCscreen68 | Male | 35 | Healthy volunteer | — |
| HCCscreen69 | Female | 42 | Healthy volunteer | — |
| HCCscreen70 | Male | 35 | Healthy volunteer | — |
| HCCscreen71 | Female | 20 | Healthy volunteer | — |
| HCCscreen72 | Female | 46 | Healthy volunteer | — |
| HCCscreen73 | Male | 26 | Healthy volunteer | — |
| HCCscreen74 | Male | 37 | Healthy volunteer | — |
| HCCscreen75 | Male | 30 | Healthy volunteer | — |
| HCCscreen76 | Male | 28 | Healthy volunteer | — |
| HCCscreen77 | Female | 33 | Healthy volunteer | — |

TABLE 1-continued

| Number | Sex | Age | Diagnosis (CT) | Tumor Size |
|---|---|---|---|---|
| HCCscreen78 | Female | 23 | Healthy volunteer | — |
| HCCscreen79 | Female | 29 | Healthy volunteer | — |
| HCCscreen80 | Female | 37 | Healthy volunteer | — |
| HCCscreen81 | Female | 31 | Healthy volunteer | — |
| HCCscreen82 | Female | 26 | Healthy volunteer | — |
| HCCscreen83 | Male | 26 | Healthy volunteer | — |
| HCCscreen84 | Male | 26 | Healthy volunteer | — |
| HCCscreen85 | Female | 26 | Healthy volunteer | — |
| HCCscreen86 | Male | 26 | Healthy volunteer | — |
| HCCscreen87 | Female | 27 | Healthy volunteer | — |
| HCCscreen88 | Female | 26 | Healthy volunteer | — |
| HCCscreen89 | Male | 25 | Healthy volunteer | — |
| HCCscreen90 | Female | 24 | Healthy volunteer | — |

Note:
"—"indicates that no tumor was recorded or detected; Tumor size is tumor volume, tumor maximum diameter, or tumor maximum cross-sectional area.

Statement of Ethics

Based on the early HCC screening program for community groups, the inventors established a community-based cohort study (CCOP-LC cohort; China Clinical Registration, ChiCTR-EOC-17012835) on high-risk groups for liver cancer in 2017. The study protocol (NCC201709011) was approved by the Institutional Review Committee of the National Cancer Center/National Clinical Research Center for Cancer/Cancer Hospital Chinese Academy of Medical Sciences.

Overview of Early HCC Screening Programs in Community Populations

Early HCC screening is based on the "Technical Plan for early diagnosis and early treatment of Cancer" issued by the Chinese expert Committee for early Detection and early treatment of Cancer of the Center for Disease Control and Prevention of the Ministry of Health (Shia Y C, Beever J E, Lewin H A, & Schook L B (1991) Restriction fragment length polymorphisms at the porcine t complex polypeptide 1 (TCP1) locus. *Anim Genet* 22(2):194.). A population-based cancer registry and demographic department were established at all screening centres (Chen W, et al. (2018) Cancer incidence and mortality in China, 2014. *Chinese journal of cancer research=Chung-kuo yen cheng yen chiu* 30(1):1-12.). Briefly, HBsAg positive "healthy" individuals between the ages of 35 and 69 were invited to participate in early HCC screening. All participants underwent serum AFP concentration determination and ultrasound examination (US; Aloka ProSound SSD-4000; Shanghai, China), as well as other standard biochemical tests (Table 2). Based on serum AFP levels and liver nodule detection, individuals were designated as AFP/US positive, suspected, or negative. An "AFP/US positive" individual has any of the following: 1) regardless of the nodules detected by ultrasound, the level of serum AFP >400 ng/mL; 2) regardless of the concentration of serum AFP, the nodules detected by ultrasound ≥2 cm; 3) the nodules detected by ultrasound ≥1 cm, and the serum AFP ≥200 ng/ml. An "AFP/US suspected" individual has any of the following: 1) serum AFP level≥20 ng/ml regardless of hepatic nodules detected by ultrasound; 2) nodules detected by ultrasound ≥1 cm. An "AFP/US negative" individual is defined as having serum AFP levels <20 ng/mL and no ultrasound-detected hepatic nodules. AFP/US positive individuals were transferred to a senior hospital (Chinese tertiary hospital) for diagnosis, such as liver cancer patients identified by dynamic CT or dynamic MRI, and receive relevant treatment based on clinical practice guidelines (FIG. 1) (Omata M, et al. (2017) Asia-Pacific clinical practice guidelines on the management of hepatocellular carcinoma: a 2017 update. *Hepatol Int* 11(4):317-370.). Undiagnosed individuals were invited to return within 2 months for dynamic CT/MRI examination. The suspected individuals of AFP/US were recommended to undergo a second round of serum AFP quantitative examination and ultrasound examination within 2-3 months.

TABLE 2

General information for participants of AFP/US screening and liquid biopsy analysis

| | HCC screening participants | Participant in liquid biopsy analysis | | | |
|---|---|---|---|---|---|
| | | AFP/US positive & suspected | | Sampled AFP/US negative | |
| | | % (number) | P-value[†] | % (number) | P-value[†] |
| Total | 3793 | 176 | N/A | 331 | N/A |
| Demographic data | | | | | |
| Age (median, age) | 50 | 54 | N/A | 52 | N/A |
| Sex, Male % | 51.73% (1962) | 68.75% (121) | <0.001 | 53.47% (177) | 0.483 |
| Previous screening, % (number) | | | | | |
| Once in a year | 24.17% (917) | 15.91% (28) | <0.001 | 41.69% (138) | <0.001 |
| Once in the past 2-3 years | 35.36% (1341) | 18.75% (33) | | 53.17% (176) | |
| None in the past 5 years | 40.47% (1535) | 65.34% (115) | | 5.13% (17) | |
| Ultrasound shows hardening | | | | | |
| % (number) | 11.13% (422) | 54.98% (95) | <0.001 | 11.18% (37) | 0.883 |

TABLE 2-continued

General information for participants of AFP/US screening and liquid biopsy analysis

| | HCC screening participants | Participant in liquid biopsy analysis | | | |
|---|---|---|---|---|---|
| | | AFP/US positive & suspected | | Sampled AFP/US negative | |
| | | % (number) | P-value[†] | % (number) | P-value[†] |
| Albumin, g/L | | | | | |
| Mean ± SD | 46.92 ± 4.81 | 43.38 ± 5.05 | | 47.19 ± 3.46 | |
| ≤35, % (number) | 1.00% (38) | 7.39% (13) | <0.001 | 0.60% (2) | 0.768[‡] |
| ALT (IU/mL), % (number) | | | | | |
| Mean ± SD | 33.41 ± 34.75 | 55.47 ± 50.56 | | 36.26 ± 43.45 | |
| <45 | 83.28% (3159) | 57.95% (102) | <0.001 | 78.85% (261) | 0.033 |
| ≥45 | 16.72% (634) | 42.05% (74) | | 21.15% (70) | |
| AFP (ng/mL) | | | | | |
| Mean ± SD | 34.34 ± 666.10 | 676.52 ± 3030.51 | | 4.38 ± 4.23 | |
| <20 | 97.07% (3682) | 36.93% (65) | <0.001 | 100% (331) | <0.001[‡] |
| ≥20 | 2.93% (111) | 63.07% (111) | | 0 | |
| HBV-DNA (IU/mL), % (number)* | | | | | |
| Median with quartile | 2.40E+02 (<30, 2.53E+03) | 3.44E+03 (1.31E+02, 6.20E+05) | | 8.25E+01 (<30, 3.25E+03) | |
| <100 | 39.88% (1298) | 23.12% (40) | <0.001 | 51.66% (171) | <0.001 |
| 100-999 999 | 51.49% (1676) | 54.34% (94) | | 39.58% (131) | |
| ≥1 000 000 | 8.63% (281) | 22.54% (39) | | 8.76% (29) | |

*Total 3255 participants were assessed for HBV-DNA concentration.
[†]For all HCC screening participants, Chi-square tests were used in addition to the P value with[‡] marker.
[‡]Fisher's exact tests were performed and compared to all HCC screening participants.

Participants and Research Design

Participants in the current study were obtained from CCOP-LC cohorts of individuals evaluated by four screening centers in Jiangsu and Anhui, China (FIG. 1). During AFP/US screening (considering baseline, performed between Oct. 7, 2017 and Jan. 31, 2018), the inventors collected peripheral blood (5 mL in EDTA coated tubes) which was centrifuged at 4000 g for 10 min within 2 h after collection to separate plasma and blood cells. All samples were stored at −80° C. In most cases, 0.5 mL of plasma was used to determine protein markers and 2 mL of plasma was used for cfDNA extraction.

Figure 2:
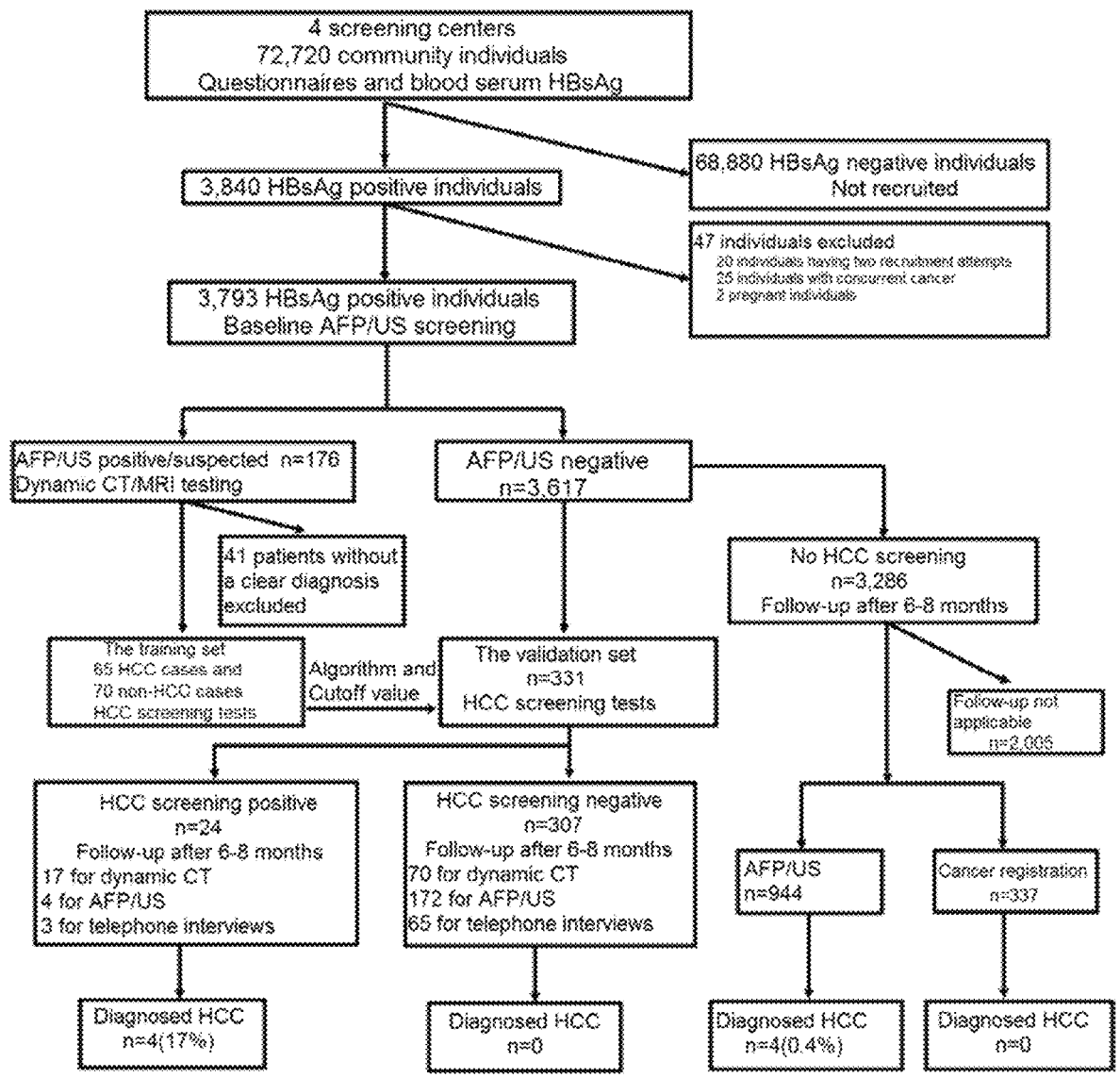
FIG. 2 is a detailed study design protocol.

176 AFP/US positive/suspected cases were further analyzed in the HCC screening assay. Participants with reliable diagnosis were selected as the training set in this study based on the results of diagnosis in follow-up examinations. To verify the inventors' findings, the present invention samples 331 participants from AFP/US negative individuals who are similar in age to AFP/US positive/suspected patients in the HCC screening assay. 331 individuals were followed up from May 20 to Jul. 17, 2018 (6-8 months after baseline blood drawing) by dynamic CT/MRI, AFP/ultrasound or telephone interview. CT/MRI images were independently evaluated by two radiologists from the National Cancer Center, Chinese Academy of Medical Sciences, Beijing. During this period, the present invention provides additional AFP/US testing for individuals who are AFP/US negative at baseline and have not undergone HCC screening testing. Some of them did not select additional AFP/US examinations and their liver cancer results (ICD-10 Code C22) before Jun. 30, 2018 were obtained from a population-based cancer registry at the screening center (FIG. 1). Of the 3617 AFP/US negative individuals, 1612 (44.6%) participants were able to follow-up from May 20 to Jul. 17, 2018, i.e. 6-8 months after baseline screening. Of these, 87 participants received dynamic CT/MRI, 1120 received AFP/US, and 68 were interviewed by telephone. The liver cancer results of 337 participants were obtained from the local population-based cancer registry (FIG. 2). The HCC status of the other 2005 participants was not available until Jun. 30, 2018 (FIG. 2).

70 healthy controls were obtained from a population undergoing an annual physical examination and reporting no HBV infection. When donating blood, all were confirmed to be HBsAg negative.

Determination of Serum DCP Concentration

According to the manufacturer's instructions (Abbott Laboratories; Chicago, Ill., USA), serum DCP levels were determined by using a commercial kit in an Abbott ARCHITECT i2000$_{SR}$ Chemiluminescence Immuno-analyzer (CLIA).

Spectrum Analysis of cfDNA Changes

The inventors designed experiments to sequence cfDNA for spectral analysis: 1) coding regions of TP53, CTNNB1, AXIN1 and a promoter region of TERT (Table 3); 2) integration of HBV. Briefly, cfDNA fragments were first linked to adaptors with random DNA bar code (FIG. 3). The linked constructs were amplified by 10 reaction cycles to produce a whole genome library containing hundreds of redundant constructs with unique DNA bar codes that recognize each original cfDNA fragment. The amplified library was sufficient for 5-10 independent sequencing analyses. The target region was amplified together with the DNA bar code in 9 cycles of PCR using target-specific primers (TS primer 1) and primers matching the ligand sequence (Perera B P & Kim J (2016) Next-generation sequencing-based 5' rapid amplification of cDNA ends for alternative promoters. *Analytical biochemistry* 494:82-84; Zheng Z, et al. (2014) Anchored multiplex PCR for targeted next-generation sequencing. *Nature medicine* 20(12):1479-1484.) (FIG. 3). A second round of 15 cycles of PCR was performed using a pair of nested primers (TS Primer 2) matching the linker and target region to further enrich the target region and add the Illumina sequencing linker (FIG. 3). Effective enrichment was observed in this PCR-based assay, >80% of the reads mapped to a small target region of <10 Kb. Using this assay, the present invention can cover target regions >100,000 times, 3 Gb sequencing data, enabling 20×redundant sequencing of 5,000 copies of the original cfDNA. Where a DNA bar code is linked to the original cfDNA molecule, redundant reads from the original cfDNA molecule can be tracked to minimize calling errors inherent in PCR amplification and parallel mutation sequencing (Kinde I, Wu J, Papadopoulos N, Kinzler K W, & Vogelstein B (2011) Detection and quantification of rare mutations with massively parallel sequencing. *Proceedings of the National Academy of Sciences of the United States of America* 108 (23):9530-9535; Chaudhuri A A, et al. (2017) Early Detection of Molecular Residual Disease in Localized Lung Cancer by Circulating Tumor DNA Profiling. *Cancer discovery* 7(12):1394-1403.). The present invention examined 11 mutations detected in this assay by digital PCR and verified all of these mutations with a mutation score of 0.03-0.16%.

TABLE 3

HCC screening characteristics and coefficient characteristics thereof

| Classification of characteristics | characteristics | Coefficient |
|---|---|---|
| cfDNA | TP53 other than R249S | 2.02 |
| | TP53 R249S | 0.21 |
| | TERT | 1.37 |
| | SV_TERT | 0.70 |
| | CTNNB1 | 1.20 |
| | AXIN1 | 0.01 |
| | Integration of HBV | 0.82 |
| | Concentration of cfDNA | −0.27 |
| Protein | AFP | 0.21 |
| | DCP | 1.59 |
| Clinical information | Sex | 0.66 |
| | Age | 1.69 |
| | (intercept) | −2.68 |

Penalty logistic regression: $\lambda=0.14$; $a=0$.

Data Processing and Mutation Detection

Sequencing reads are processed to extract tags and remove sequence adaptors. Trimmatomatic (v0.36) was then used to remove residual linkers and low quality regions. The 'bwa (v0.7.10) mem' with default parameters (Li H & Durbin R (2010) Fast and accurate long-read alignment with Burrows-Wheeler transform. *Bioinformatics* 26(5):589-595.) was used to map the clean reads to the hg19 and HBV genomes. Samtools mpileup (Li H, et al. (2009) The Sequence Alignment/Map format and SAMtools. *Bioinformatics* 25(16):2078-2079.) was used to identify candidate mutations consisting of SNP and INDEL in the target region of interest. To ensure accuracy, reads with the same tag and start and end coordinates are grouped into a Unique Identifier family (UID family). A UID family containing at least two reads and at least 80% of the reads of the same type is defined as an Effective Unique Identifier family (EUID family) Each mutation frequency is calculated by dividing the number of alternative EUID families by the sum of the alternatives and the references. Mutations were further examined manually in IGV. Candidate variants were annotated with Ensembl Variant Effect Predictor (VEP) (Wang J, et al. (2011) CREST maps somatic structural variation in cancer genomes with base-pair resolution. *Nat Methods* 8(8):652-654). HBV integration was identified by using Crest (McLaren W, et al. (2016) The Ensembl Variant Effect Predictor. *Genome biology* 17(1):122.) and requires at least 4 soft-clip reads supports.

Model Construction

1. Feature Mapping and Data Preprocessing

1) Mutation Notes and Scores:

The mutation frequency (the fraction of reads supporting candidate mutations) is highly proportional to the total amount of circulating tumor DNA in the blood and tumor size. Thus, the present invention annotates all input mutations with their reads supporting frequency.

2) Decomposition of Mutations

Multiple gene characteristics are extracted by decomposing the mutation into gene levels or focal regions. For each region of interest (ROI), the ROI score is obtained by calculation.

$$ROI = \log 2 \sum_{i=1}^{n} \mathrm{adj\_score}_i$$

Where n is the number of mutations overlapping the ROI and adj_score is the reads support frequency of the mutation.

3) Proteins and Experimental Markers

Two protein markers DCP and AFP were used in the model of the present invention because they have been shown in previous studies to be very strong indicators of HCC diagnosis (Chen H, et al. (2018) Direct comparison of five serum biomarkers in early diagnosis of hepatocellular carcinoma. *Cancer management and research* 10:1947-1958.). These values are ranked into a plurality of numerical categories. The cfDNA concentrations are also included in the list of model characteristics of the present invention.

4) Clinical Information as Characteristics

The age and sex of the patient also comprised of part of the predictor of the present invention, as it has been demonstrated that the likelihood of HCC diagnosis is somewhat related to the age and sex of the individual.

2. Characteristics Selection

The RandomForest is used for screening useful variables from candidate characteristics; the inventors applied backward variables subtraction by minimizing unbiased out-of-bag error estimation, eliminating one characteristic per run. The protein, gene markers, and clinical information are then optimized to construct the final characteristics of the binary classifier. In the training of HCC compared to healthy individuals, only ctDNA SNP/indel mutations and protein markers were used. HBV-TERT fusion or other HBV integration is not included because the healthy group has no HBV infection.

3. Model and Parameter Optimization

The penalty logistic regression model was constructed from a training set of 135 samples containing 65 HCC cases and 70 non-HCC cases. Model performance was evaluated on both the training and validation data sets by area under the curve (AUC) statistics. The sensitivity and specificity of the model were also determined by using an optimized cut-off value of 0.4. The Youden index is used for optimization of this cut-off value. In order to perform cluster analysis of gene, protein and CNV levels respectively, the cross-validation coefficient of each characteristic using penalty logic regression is also given. The model is started in the R package 'glmnet' (R version 3.5.1), and the penalty parameter a is optimized in the training data set by 10-fold cross validation, and the optimized value is 0.

Statistical Analysis

The present invention uses a penalty logistic regression model with ctDNA mutations, protein biomarker levels, and clinical characteristics as variables. The inventors defined HCC cases and non-HCC cases with dynamic CT/MRI and/or histology in AFP/US positive and AFP/US suspected individuals (FIG. 1). The sensitivity and specificity of HCC screening assays were calculated by LOOCV (Leave-One-Out Cross Validation) with 100 iterations on training data sets of 65 HCC cases and 70 non-HCC cases.

Example 1. Clinical Parameters of Baseline Participants in Four Screening Centers and Follow-Up of Results of Hepatocellular Carcinoma (HCC)

Community individuals (n=72720) were screened by the blood hepatitis B surface antigen (HBsAg) test in four screening centers and then questionnaires were conducted. HBsAg positive individuals (n=3793) were invited to participate in AFP/US screening. Of these HBsAg positive individuals, 176 had relevant AFP/US results (designated AFP/US positive/suspected group), while the remaining HBsAg positive patients constituted the AFP/US negative group (n=3617) (FIG. 1 and Table 3). To determine their HCC status, it is recommended that all AFP/US positive/suspected individuals undergo dynamic CT/MRI testing within 2 months of the first screening. Patients with reliable diagnosis of HCC status were included in the training set of this study, and baseline AFP/US blood samples obtained from these individuals were subjected to HCC screening tests (FIG. 1).

Of the 3617 AFP/US negative individuals, approximately 60% had been subjected to AFP/US screening prior to baseline screening in this study (FIG. 2 and Table 3). To reduce anxiety and non-compliance during follow-up procedures, the present invention primarily selects individuals who have undergone AFP/US screening in the past 1-3 years as a validation set (n=331). Based on sex, the proportion of cirrhosis detected by US and serum albumin levels, the distribution of sampled AFP/US negative participants was similar to all HBsAg positive participants (FIG. 2 and Table 3). The present invention performs HCC liquid biopsy testing (HCC screening) on blood samples collected from a validation set at baseline AFP/US screening and HCC status was followed up 6-8 months after baseline screening. The present invention also screened 70 healthy individuals without HBV infection for HCC.

Example 2. Selection and Detection of HCC Markers Using HCC Screening

The invention uses two types of biomarkers to develop an HCC screening assay: 1) Gene alterations that are very common in HCC and can be detected in cfDNA; And 2) serum protein markers-alpha-fetoprotein (AFP) and des-γ-carboxyprothrombin (DCP). In previous cancer genome studies, most HBV-related HCC carried at least one mutation in the following gene/position: TP53, CTNNB1, AXIN1 or TERT promoter (Totoki Y, et al. (2014) Trans-ancestry mutational landscape of hepatocellular carcinoma genomes. Nature genetics 46(12):1267-1273; Zhang W, et al. (2017) Genetic Features of Aflatoxin-associated Hepatocellular Carcinomas. Gastroenterology.). The present invention also contemplates HBV integration breakpoints as potential biomarkers for HCC. Since the HBV integration site should be unique in each individual cell, detection of multiple copies (>2) of a particular integration site from plasma (2-3 ml) may indicate clonal expansion of a single cell carrying HBV integration. Only in this case will the resulting tumor release multiple copies of the same genomic DNA into the blood. The present invention contemplates assays that can profile gene changes in parallel. The extracted cfDNA is linked to a custom linker with a DNA bar code and then amplified to generate a whole genome library. Using a method similar to rapid amplification of cDNA ends (RACE), the inventors used multiple primers covering the coding regions of TP53, CTNNB1 and AXIN1, the promoter region of TERT and HBV sequences to enrich targets with point mutations and HBV integration (FIG. 3) (Chaudhuri A A, et al. (2017) Early Detection of Molecular Residual Disease in Localized Lung Cancer by Circulating Tumor DNA Profiling. Cancer discovery 7(12):1394-1403; Waltari E, et al. (2018) 5' Rapid Amplification of cDNA Ends and Illumina MiSeq Reveals B Cell Receptor Features in Healthy Adults, Adults With Chronic HIV-1 Infection, Cord Blood, and Humanized Mice. Frontiers in immunology 9:628.). Secondary sequenced reads can be traced to the original cfDNA molecule by DNA bar codes, thereby filtering false positive single nucleotide variations (SNV) from sequencing/amplification errors (Kinde I, Wu J, Papadopoulos N, Kinzler K W, & Vogelstein B (2011) Detection and quantification of rare mutations with massively parallel sequencing. Proceedings of the National Academy of Sciences of the United States of America 108(23):9530-9535.).

Based on previous findings by the inventors and reports from other hospitalized patients affected by HCC, cirrhosis and chronic hepatitis, the combination of serum protein levels of AFP and DCP showed significant sensitivity and specificity in distinguishing between early HCC and decompensated cirrhosis (Chen H, et al. (2018) Direct comparison of five serum biomarkers in early diagnosis of hepatocellular carcinoma. Cancer management and research 10:1947-1958.). Thus, the present invention combines these two serum protein markers with changes in cfDNA to investigate whether such liquid biopsy-based assays (including AFP, DCP and cfDNA) can effectively screen early HCC.

Example 3. Consistency of Clinical Diagnosis with HCC Screening Assays

Figure 5A:
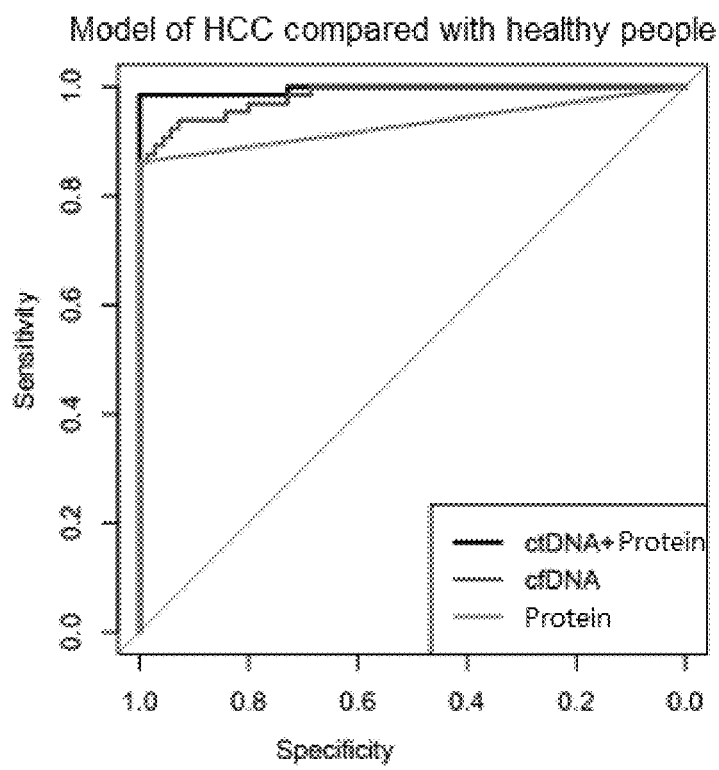
Figure 5B:
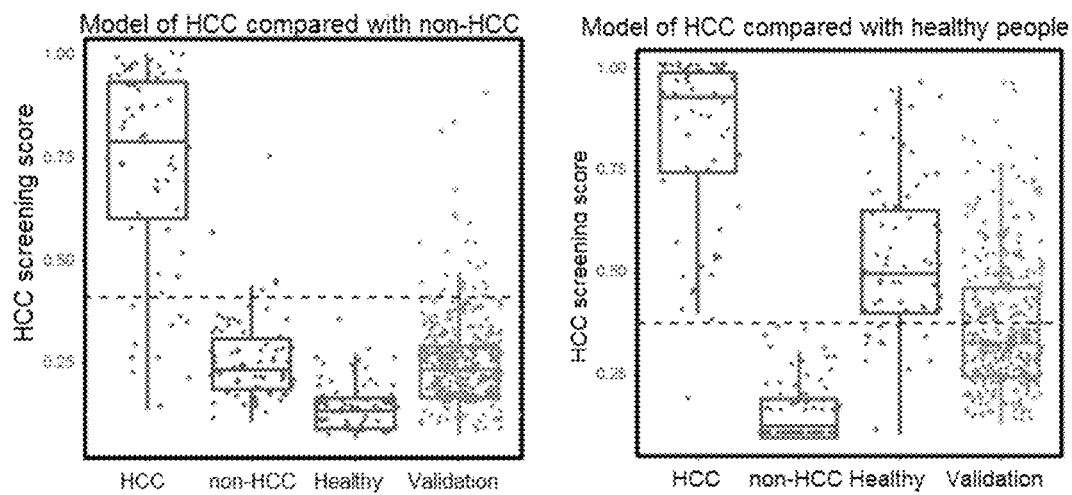

To determine its utility in HCC detection, the present invention performs HCC screening in individuals known to be diagnosed with HCC or who have been excluded (non-HCC). 65 HCC cases and 70 non-HCC cases were obtained from AFP/US positive/suspected individuals. The HCC positive or HCC negative status is based on dynamic CT/MRI imaging and histological confirmation. These 135 cases were used as training sets and HCC screening results were compared with clinical diagnosis. To establish a classifier that integrates different types of biomarkers in an assay, the present invention first collapses different types of cfDNA mutations into regions of interest (ROI) scores for each gene or locus. The ROI score is a weighted sum of the destruction effect and frequency of each point mutation within the ROI. In addition to the ROI score of the SNV/indel mutation in the gene, the present invention adds two structural variant characteristics (HBV integration and other HBV integration in the TERT promoter region), one experimental characteristic (cfDNA concentration), two protein markers (AFP and DCP), and two clinical characteristics (age and sex) as final characteristics for constructing a diagnostic classifier to predict HCC status (Table 2). with these markers, the HCC screening model distinguished HCC cases from non-HCC cases by using a penalty logistic regression algorithm (FIG. 4A). This assay was found to have 85% sensitivity and 93% specificity in HCC diagnosis (area under the curve=0.928) (FIG. 4B and FIG. 4C) by 100 repeated leave-one-out cross validation of training data sets including 65 HCC cases and 70 non-HCC cases. The HCC screening score cut-off value was 0.4 for the highest Youden index score (FIG. 5B and Table 4). Both cfDNA and protein markers contribute significantly to HCC recognition (FIG. 4C and Table 5).

TABLE 4

Features and HCC Screening Scores

| Set | ID | Sex | Age | AFP (ng/ml) | DCP (mAU/ml) | Integration of HBV | HCC screening score |
|---|---|---|---|---|---|---|---|
| Training-HCC | RG871NM1 | Male | 68 | 14.86 | 231.11 | 13 | 1.00 |
| Training-HCC | RG898NM1 | Male | 62 | 1811.25 | 304.45 | 7 | 0.99 |
| Training-HCC | RH443NM1 | Male | 66 | 3442.19 | 2624.6 | 2 | 0.99 |
| Training-HCC | RG872NM1 | Male | 65 | 2.99 | 487.02 | 11 | 0.98 |
| Training-HCC | RG895NM1 | Male | 69 | 3338.52 | >30000 | 5 | 0.98 |
| Training-HCC | RH390NM1 | Male | 52 | 20000 | 27118.7 | 11 | 0.97 |
| Training-HCC | RG876NM1 | Male | 63 | 23.93 | 242.5 | 9 | 0.97 |
| Training-HCC | RG869NM1 | Male | 68 | 26.22 | 188.95 | 9 | 0.97 |
| Training-HCC | RH455NM1 | Female | 70 | 87.07 | 1123.06 | 2 | 0.97 |
| Training-HCC | RH377NM1 | Male | 71 | 88.89 | 198.35 | 1 | 0.96 |
| Training-HCC | RG883NM1 | Male | 65 | 3284.6 | >30000 | 6 | 0.96 |
| Training-HCC | RH421NM1 | Male | 49 | 24.43 | 78.54 | 13 | 0.96 |
| Training-HCC | RH397NM1 | Female | 66 | 4260.1 | 213.25 | 4 | 0.96 |
| Training-HCC | RG878NM1 | Male | 55 | 7.66 | 423.93 | 0 | 0.95 |
| Training-HCC | RH419NM1 | Male | 48 | 96.91 | 4250.46 | 2 | 0.95 |
| Training-HCC | RH897NM1 | Male | 59 | 4.27 | 1871.1 | 6 | 0.95 |
| Training-HCC | RG881NM1 | Male | 50 | 14.48 | 2464.26 | 7 | 0.94 |
| Training-HCC | RH414NM1 | Male | 51 | 23.17 | 470.61 | 0 | 0.93 |
| Training-HCC | RH385NM1 | Male | 66 | 7537.75 | 1606.41 | 3 | 0.93 |
| Training-HCC | RH398NM1 | Male | 68 | 138.38 | 94.12 | 2 | 0.92 |
| Training-HCC | RG873NM1 | Male | 70 | 199.35 | 342.12 | 1 | 0.91 |
| Training-HCC | RH373NM1 | Male | 44 | 20000 | 1175.16 | 6 | 0.89 |
| Training-HCC | RG774NM1 | Male | 56 | 97.09 | 98 | 5 | 0.89 |
| Training-HCC | RG868NM1 | Male | 46 | 1.12 | 65.95 | 5 | 0.89 |
| Training-HCC | RH380NM1 | Male | 67 | 24.59 | 416.13 | 1 | 0.88 |
| Training-HCC | RG776NM1 | Male | 75 | 12 | 265 | 0 | 0.87 |
| Training-HCC | RG888NM1 | Male | 60 | 1.92 | 72.66 | 0 | 0.86 |
| Training-HCC | RG897NM1 | Male | 69 | 6.55 | 20.84 | 9 | 0.85 |
| Training-HCC | RG796NM1 | Male | 58 | 238.7 | 38.59 | 5 | 0.83 |
| Training-HCC | RH394NM1 | Female | 53 | 19031 | 1555.36 | 2 | 0.82 |
| Training-HCC | RH903NM1 | Male | 64 | 4.31 | 7994.33 | 2 | 0.82 |
| Training-HCC | RH440NM1 | Male | 54 | 104.28 | 509.12 | 2 | 0.81 |
| Training-HCC | RG892NM1 | Male | 54 | 1.71 | 81.47 | 1 | 0.78 |
| Training-HCC | RG886NM1 | Female | 70 | 130.95 | 148.62 | 3 | 0.78 |
| Training-HCC | RH369NM1 | Male | 61 | 461.02 | 267.58 | 0 | 0.77 |
| Training-HCC | RG904NM1 | Male | 56 | 1843.39 | 23.06 | 4 | 0.76 |
| Training-HCC | RH900NM1 | Male | 49 | 3.28 | 15.11 | 0 | 0.75 |
| Training-HCC | RH898NM1 | Male | 49 | 4.28 | 422.37 | 3 | 0.75 |
| Training-HCC | RH137NM1 | Male | 53 | 5.83 | 140.5 | 0 | 0.75 |
| Training-HCC | RG785NM1 | Female | 53 | 1210 | 22.71 | 0 | 0.74 |
| Training-HCC | RH462NM1 | Male | 70 | 24.08 | 14.46 | 16 | 0.71 |
| Training-HCC | RG804NM1 | Male | 59 | 132.2 | 205.77 | 0 | 0.71 |
| Training-HCC | RH381NM1 | Male | 55 | 22.28 | 229.71 | 3 | 0.69 |
| Training-HCC | RG905NM1 | Female | 68 | 2.3 | 180.03 | 1 | 0.69 |
| Training-HCC | RG773NM1 | Male | 48 | 6.5 | 178 | 6 | 0.69 |
| Training-HCC | RH441NM1 | Male | 48 | 20000 | 1237.34 | 1 | 0.66 |
| Training-HCC | RH891NM1 | Female | 42 | 11.22 | 17.18 | 7 | 0.62 |
| Training-HCC | RG790NM1 | Male | 49 | 36.48 | 2393.86 | 0 | 0.62 |
| Training-HCC | RH905NM1 | Male | 58 | 2.4 | 55.1 | 1 | 0.56 |
| Training-HCC | RG870NM1 | Female | 68 | 125.99 | 21.59 | 1 | 0.50 |
| Training-HCC | RG901NM1 | Male | 63 | 5.37 | 19.14 | 2 | 0.50 |
| Training-HCC | RH425NM1 | Male | 50 | 18.23 | 16.43 | 1 | 0.47 |
| Training-HCC | RH382NM1 | Male | 55 | 28.76 | 27.55 | 1 | 0.43 |
| Training-HCC | RG903NM1 | Male | 42 | 1380.46 | 50.14 | 1 | 0.43 |
| Training-HCC | RH402NM1 | Male | 64 | 327.55 | 25.13 | 3 | 0.41 |
| Training-HCC | RH906NM1 | Male | 52 | 3.07 | 18.19 | 0 | 0.34 |
| Training-HCC | RH379NM1 | Female | 71 | 115.29 | 21.29 | 0 | 0.34 |
| Training-HCC | RG894NM1 | Male | 69 | 1.79 | 11.39 | 0 | 0.34 |
| Training-HCC | RG879NM1 | Female | 66 | 2.4 | 7.14 | 0 | 0.28 |
| Training-HCC | RG902NM1 | Male | 39 | 2136.1 | 18.58 | 2 | 0.27 |
| Training-HCC | RH422NM1 | Male | 51 | 111.46 | 26.58 | 0 | 0.26 |
| Training-HCC | RG896NM1 | Male | 53 | 2.06 | 12.87 | 1 | 0.25 |
| Training-HCC | RH460NM1 | Male | 42 | 34.58 | 21.39 | 0 | 0.21 |
| Training-HCC | RH889NM1 | Female | 67 | 4.05 | 19.77 | 0 | 0.21 |
| Training-HCC | RG781NM1 | Female | 48 | 177.7 | 30.57 | 0 | 0.14 |
| Training-non-HCC | RH393NM1 | Female | 64 | 24.03 | 167.25 | 0 | 0.70 |
| Training-non-HCC | RH430NM1 | Male | 56 | 27.87 | 36.33 | 3 | 0.58 |
| Training-non-HCC | RG792NM1 | Female | 54 | 76.34 | 17.69 | 22 | 0.44 |
| Training-non-HCC | RH878NM1 | Male | 62 | 8.62 | 25.51 | 0 | 0.42 |
| Training-non-HCC | RH915NM1 | Male | 63 | 2.71 | 18.55 | 0 | 0.41 |
| Training-non-HCC | RH450NM1 | Male | 70 | 106.36 | 32.14 | 0 | 0.38 |
| Training-non-HCC | RH438NM1 | Male | 49 | 31.52 | 12.16 | 5 | 0.37 |
| Training-non-HCC | RH459NM1 | Male | 63 | 209.03 | 16.17 | 0 | 0.37 |
| Training-non-HCC | RH383NM1 | Male | 53 | 21.06 | 27.22 | 0 | 0.37 |
| Training-non-HCC | RH395NM1 | Female | 68 | 321.84 | 16.02 | 4 | 0.37 |

TABLE 4-continued

Features and HCC Screening Scores

| Set | ID | Sex | Age | AFP (ng/ml) | DCP (mAU/ml) | Integration of HBV | HCC screening score |
|---|---|---|---|---|---|---|---|
| Training-non-HCC | RH418NM1 | Male | 46 | 58.25 | 18.99 | 4 | 0.37 |
| Training-non-HCC | RH428NM1 | Male | 58 | 449.17 | 17.67 | 0 | 0.35 |
| Training-non-HCC | RH431NM1 | Male | 63 | 40.04 | 16.79 | 0 | 0.34 |
| Training-non-HCC | RH879NM1 | Male | 67 | 2.32 | 14.99 | 0 | 0.34 |
| Training-non-HCC | RH400NM1 | Male | 44 | 66.32 | 21.11 | 1 | 0.33 |
| Training-non-HCC | RH883NM1 | Male | 66 | 2.74 | 10.49 | 1 | 0.32 |
| Training-non-HCC | RG801NM1 | Male | 56 | 37.33 | 21.09 | 5 | 0.32 |
| Training-non-HCC | RH408NM1 | Female | 61 | 23.47 | 20.16 | 1 | 0.32 |
| Training-non-HCC | RH378NM1 | Female | 66 | 57.89 | 15.14 | 1 | 0.30 |
| Training-non-HCC | RH409NM1 | Male | 38 | 770.97 | 23.32 | 8 | 0.29 |
| Training-non-HCC | RH371NM1 | Male | 54 | 24.7 | 25.07 | 1 | 0.29 |
| Training-non-HCC | RG794NM1 | Male | 54 | 28.34 | 39.51 | 3 | 0.28 |
| Training-non-HCC | RG805NM1 | Female | 55 | 119.9 | 21.06 | 1 | 0.28 |
| Training-non-HCC | RH452NM1 | Male | 38 | 42.01 | 8.26 | 0 | 0.28 |
| Training-non-HCC | RH461NM1 | Male | 53 | 55.83 | 10.49 | 0 | 0.28 |
| Training-non-HCC | RH415NM1 | Male | 54 | 97.82 | 11.48 | 0 | 0.28 |
| Training-non-HCC | RG795NM1 | Male | 54 | 108.3 | 39.45 | 0 | 0.28 |
| Training-non-HCC | RH406NM1 | Male | 53 | 25.16 | 25.04 | 0 | 0.28 |
| Training-non-HCC | RH437NM1 | Female | 57 | 48.16 | 12.82 | 0 | 0.27 |
| Training-non-HCC | RH882NM1 | Male | 56 | 3.61 | 11.99 | 0 | 0.26 |
| Training-non-HCC | RH423NM1 | Male | 47 | 32.66 | 24.85 | 2 | 0.26 |
| Training-non-HCC | RH413NM1 | Male | 48 | 21.85 | 19.83 | 1 | 0.25 |
| Training-non-HCC | RH884NM1 | Female | 45 | 2.45 | 23.35 | 3 | 0.25 |
| Training-non-HCC | RG787NM1 | Male | 46 | 21.27 | 27.75 | 2 | 0.24 |
| Training-non-HCC | RH420NM1 | Male | 45 | 43.84 | 17.12 | 2 | 0.24 |
| Training-non-HCC | RH376NM1 | Male | 39 | 242 | 25.74 | 0 | 0.24 |
| Training-non-HCC | RH445NM1 | Male | 43 | 107.99 | 27.52 | 3 | 0.23 |
| Training-non-HCC | RH881NM1 | Male | 50 | 2.67 | 11.29 | 0 | 0.23 |
| Training-non-HCC | RG780NM1 | Male | 41 | 117.1 | 26.67 | 2 | 0.22 |
| Training-non-HCC | RH910NM1 | Female | 52 | 4.12 | 17.02 | 2 | 0.22 |
| Training-non-HCC | RH372NM1 | Male | 44 | 141.16 | 20.53 | 0 | 0.22 |
| Training-non-HCC | RH399NM1 | Male | 43 | 35.87 | 21.34 | 1 | 0.22 |
| Training-non-HCC | RH151NM1 | Male | 47 | 11.14 | 30.64 | 0 | 0.21 |
| Training-non-HCC | RH885NM1 | Female | 54 | 9.31 | 25.36 | 0 | 0.21 |
| Training-non-HCC | RG803NM1 | Female | 64 | 32.24 | 33.92 | 0 | 0.21 |
| Training-non-HCC | RH411NM1 | Female | 62 | 31.42 | 25.63 | 0 | 0.20 |
| Training-non-HCC | RH367NM1 | Female | 63 | 22.6 | 28.38 | 0 | 0.20 |
| Training-non-HCC | RH433NM1 | Female | 62 | 77.56 | 26.57 | 0 | 0.20 |
| Training-non-HCC | RG778NM1 | Male | 38 | 33.02 | 27.5 | 0 | 0.20 |
| Training-non-HCC | RG877NM1 | Female | 66 | 4.33 | 14.69 | 0 | 0.19 |
| Training-non-HCC | RH449NM1 | Male | 37 | 48.7 | 21.58 | 0 | 0.19 |
| Training-non-HCC | RG788NM1 | Female | 60 | 49.62 | 13.24 | 3 | 0.19 |
| Training-non-HCC | RH902NM1 | Female | 66 | 1.79 | 18.04 | 0 | 0.19 |
| Training-non-HCC | RG797NM1 | Female | 56 | 31.64 | 15.49 | 4 | 0.19 |
| Training-non-HCC | RH370NM1 | Male | 34 | 25.2 | 33.21 | 0 | 0.18 |
| Training-non-HCC | RH429NM1 | Female | 53 | 249.1 | 14.35 | 0 | 0.17 |
| Training-non-HCC | RG900NM1 | Female | 53 | 4.81 | 9.19 | 5 | 0.17 |
| Training-non-HCC | RH446NM1 | Female | 47 | 28.96 | 19.74 | 6 | 0.16 |
| Training-non-HCC | RH368NM1 | Female | 55 | 95.88 | 17.92 | 0 | 0.16 |
| Training-non-HCC | RH908NM1 | Female | 54 | 3.92 | 29.51 | 0 | 0.16 |
| Training-non-HCC | RG891NM1 | Female | 57 | 7.78 | 17.99 | 0 | 0.16 |
| Training-non-HCC | RG890NM1 | Female | 51 | 309.58 | 11.02 | 0 | 0.16 |
| Training-non-HCC | RG889NM1 | Female | 55 | 2.7 | 11.44 | 0 | 0.15 |
| Training-non-HCC | RH465NM1 | Female | 49 | 35.12 | 14.32 | 0 | 0.15 |
| Training-non-HCC | RH914NM1 | Female | 53 | 1.81 | 20.43 | 0 | 0.14 |
| Training-non-HCC | RH451NM1 | Female | 47 | 130.72 | 28.01 | 0 | 0.14 |
| Training-non-HCC | RG893NM1 | Female | 52 | 1.86 | 10.37 | 1 | 0.14 |
| Training-non-HCC | RH464NM1 | Female | 48 | 24.27 | 10.28 | 0 | 0.13 |
| Training-non-HCC | RG887NM1 | Female | 44 | 1 | 18.34 | 0 | 0.12 |
| Training-non-HCC | RH916NM1 | Female | 40 | 1.38 | 33.04 | 0 | 0.11 |
| Training-health | HN45NM1 | Male | 56 | 5.4 | 29.38 | 0 | 0.35 |
| Training-health | HN36NM1 | Male | 56 | 3.16 | 26.88 | 0 | 0.27 |
| Training-health | HN67NM1 | Male | 52 | 1.3 | 14.96 | 0 | 0.25 |
| Training-health | HN60NM1 | Male | 52 | 3.29 | 23.62 | 0 | 0.25 |
| Training-health | HN39NM1 | Male | 41 | 3.38 | 38.05 | 0 | 0.25 |
| Training-health | HN50NM1 | Male | 49 | 3.14 | 24.09 | 0 | 0.24 |
| Training-health | HN56NM1 | Male | 49 | 5.17 | 23.56 | 0 | 0.24 |
| Training-health | HN57NM1 | Male | 48 | 1.85 | 28.18 | 0 | 0.23 |
| Training-health | HN62NM1 | Male | 46 | 2.3 | 30.67 | 0 | 0.22 |
| Training-health | HN53NM1 | Male | 34 | 1.7 | 27.57 | 0 | 0.21 |
| Training-health | HN69NM1 | Male | 42 | 3.86 | 20.15 | 0 | 0.20 |
| Training-health | HN61NM1 | Male | 41 | 4.21 | 18.98 | 0 | 0.19 |
| Training-health | HN06NM1 | Male | 40 | 3.12 | 17.63 | 0 | 0.19 |
| Training-health | HN65NM1 | Female | 48 | 1.77 | 16.01 | 0 | 0.18 |
| Training-health | HN52NM1 | Male | 39 | 1.3 | 20.81 | 0 | 0.18 |

TABLE 4-continued

Features and HCC Screening Scores

| Set | ID | Sex | Age | AFP (ng/ml) | DCP (mAU/ml) | Integration of HBV | HCC screening score |
|---|---|---|---|---|---|---|---|
| Training-health | HN58NM1 | Male | 39 | 1.94 | 28.07 | 0 | 0.18 |
| Training-health | HN10NM1 | Male | 35 | 1.72 | 20.63 | 0 | 0.17 |
| Training-health | HN02NM1 | Male | 34 | 2.7 | 31.31 | 0 | 0.17 |
| Training-health | HN32NM1 | Male | 33 | 4.24 | 25.02 | 0 | 0.16 |
| Training-health | HN01NM1 | Male | 32 | 2.55 | 25.95 | 0 | 0.16 |
| Training-health | HN04NM1 | Male | 32 | 2.42 | 25.03 | 0 | 0.16 |
| Training-health | HN07NM1 | Male | 30 | 1.04 | 25.33 | 0 | 0.15 |
| Training-health | HN35NM1 | Male | 30 | 3.82 | 32.02 | 0 | 0.15 |
| Training-health | HN48NM1 | Male | 30 | 3.21 | 26.9 | 0 | 0.15 |
| Training-health | HN08NM1 | Male | 29 | 1.29 | 22.82 | 0 | 0.15 |
| Training-health | HN33NM1 | Male | 29 | 3.82 | 29.22 | 0 | 0.15 |
| Training-health | HN03NM1 | Male | 28 | 3.27 | 34.29 | 0 | 0.14 |
| Training-health | HN09NM1 | Male | 28 | 2.5 | 22.13 | 0 | 0.14 |
| Training-health | HN11NM1 | Male | 28 | 2.11 | 26.1 | 0 | 0.14 |
| Training-health | HN34NM1 | Male | 27 | 1.97 | 21.85 | 0 | 0.14 |
| Training-health | HN19NM1 | Male | 27 | 3.65 | 31.3 | 0 | 0.14 |
| Training-health | HN43NM1 | Female | 49 | 1.56 | 21.16 | 0 | 0.14 |
| Training-health | HN51NM1 | Male | 27 | 1.89 | 21.67 | 0 | 0.13 |
| Training-health | HN15NM1 | Male | 26 | 2.77 | 23.78 | 0 | 0.13 |
| Training-health | HN16NM1 | Male | 26 | 6.55 | 30.78 | 0 | 0.13 |
| Training-health | HN66NM1 | Female | 48 | 3.83 | 25.49 | 0 | 0.13 |
| Training-health | HN18NM1 | Male | 25 | 2.86 | 38.26 | 0 | 0.13 |
| Training-health | HN49NM1 | Female | 37 | 2.82 | 16.24 | 0 | 0.13 |
| Training-health | HN59NM1 | Female | 47 | 2.43 | 15.18 | 0 | 0.13 |
| Training-health | HN68NM1 | Male | 24 | 1.33 | 18.75 | 0 | 0.13 |
| Training-health | HN54NM1 | Male | 24 | 2.85 | 20.71 | 0 | 0.13 |
| Training-health | HN21NM1 | Male | 23 | 1.01 | 37.04 | 0 | 0.12 |
| Training-health | HN37NM1 | Female | 36 | 2.22 | 31.52 | 0 | 0.12 |
| Training-health | HN40NM1 | Female | 44 | 1.7 | 23.68 | 0 | 0.12 |
| Training-health | HN63NM1 | Female | 44 | 4.41 | 27.13 | 0 | 0.12 |
| Training-health | HN64NM1 | Female | 40 | 1.26 | 28.33 | 0 | 0.11 |
| Training-health | HN46NM1 | Female | 38 | 2.27 | 17.91 | 0 | 0.10 |
| Training-health | HN13NM1 | Female | 37 | 5.47 | 25.68 | 0 | 0.10 |
| Training-health | HN44NM1 | Female | 37 | 5.09 | 25.52 | 0 | 0.10 |
| Training-health | HN23NM1 | Female | 36 | 5.35 | 17.69 | 0 | 0.10 |
| Training-health | HN31NM1 | Female | 36 | 3.02 | 19.51 | 0 | 0.10 |
| Training-health | HN70NM1 | Female | 36 | 1 | 15.49 | 0 | 0.10 |
| Training-health | HN55NM1 | Female | 33 | 2.18 | 25.54 | 0 | 0.09 |
| Training-health | HN20NM1 | Female | 32 | 2.73 | 13.98 | 0 | 0.09 |
| Training-health | HN14NM1 | Female | 31 | 2.21 | 17.95 | 0 | 0.09 |
| Training-health | HN25NM1 | Female | 31 | 1.76 | 18.58 | 0 | 0.09 |
| Training-health | HN41NM1 | Female | 31 | 2.79 | 22.96 | 0 | 0.08 |
| Training-health | HN05NM1 | Female | 29 | 3.09 | 28.6 | 0 | 0.08 |
| Training-health | HN12NM1 | Female | 29 | 2.65 | 32.78 | 0 | 0.08 |
| Training-health | HN47NM1 | Female | 29 | 1.34 | 19.03 | 0 | 0.08 |
| Training-health | HN28NM1 | Female | 28 | 2.06 | 22.86 | 0 | 0.08 |
| Training-health | HN42NM1 | Female | 28 | 2.97 | 20.15 | 0 | 0.08 |
| Training-health | HN38NM1 | Female | 28 | 1.81 | 19.03 | 0 | 0.08 |
| Training-health | HN17NM1 | Female | 27 | 2.76 | 24.36 | 0 | 0.08 |
| Training-health | HN26NM1 | Female | 27 | 1.84 | 19.49 | 0 | 0.08 |
| Training-health | HN27NM1 | Female | 26 | 1.11 | 17.59 | 0 | 0.07 |
| Training-health | HN24NM1 | Female | 25 | 2.18 | 15.06 | 0 | 0.07 |
| Training-health | HN29NM1 | Female | 25 | 1.85 | 14.85 | 0 | 0.07 |
| Training-health | HN30NM1 | Female | 24 | 1.52 | 15.8 | 0 | 0.07 |
| Training-health | HN22NM1 | Female | 22 | 1.6 | 28.4 | 0 | 0.07 |
| Verification | RH585NM1 | Male | 58 | 8.33 | 85.46 | 0 | 0.91 |
| Verification | RH391NM1 | Male | 62 | 14.96 | 87.41 | 0 | 0.84 |
| Verification | RH206NM1 | Male | 58 | 16.47 | 64.76 | 4 | 0.82 |
| Verification | RH134NM1 | Male | 60 | 12.14 | 32.99 | 11 | 0.67 |
| Verification | RH245NM1 | Male | 49 | 2.75 | 1355.1 | 0 | 0.62 |
| Verification | RH165NM1 | Male | 66 | 2.85 | 25.22 | 2 | 0.59 |
| Verification | RH291NM1 | Female | 53 | 1.87 | 18.91 | 0 | 0.59 |
| Verification | RH256NM1 | Male | 50 | 2.13 | 37.02 | 0 | 0.56 |
| Verification | RH283NM1 | Female | 62 | 1.68 | 67.64 | 0 | 0.53 |
| Verification | RH127NM1 | Male | 63 | 3.34 | 19.79 | 8 | 0.53 |
| Verification | RH476NM1 | Male | 59 | 8.5 | 22.8 | 0 | 0.51 |
| Verification | RH567NM1 | Male | 54 | 1.74 | 23.63 | 0 | 0.48 |
| Verification | RG874NM1 | Male | 68 | 3.91 | 11.96 | 0 | 0.48 |
| Verification | RH147NM1 | Male | 43 | 3.27 | 21.22 | 18 | 0.48 |
| Verification | RH547NM1 | Male | 54 | 3.87 | 14.2 | 1 | 0.47 |
| Verification | RH384NM1 | Male | 55 | 19.17 | 55.04 | 2 | 0.45 |
| Verification | RH227NM1 | Male | 59 | 3.94 | 32.95 | 0 | 0.44 |
| Verification | RH520NM1 | Male | 54 | 1.49 | 22.75 | 0 | 0.44 |
| Verification | RH602NM1 | Male | 57 | 4.82 | 23.11 | 0 | 0.43 |
| Verification | RG899NM1 | Male | 61 | 2.75 | 19.39 | 2 | 0.43 |

TABLE 4-continued

Features and HCC Screening Scores

| Set | ID | Sex | Age | AFP (ng/ml) | DCP (mAU/ml) | Integration of HBV | HCC screening score |
|---|---|---|---|---|---|---|---|
| Verification | RH507NM1 | Male | 57 | 4.09 | 46.58 | 0 | 0.42 |
| Verification | RH232NM1 | Male | 59 | 2.1 | 25.92 | 0 | 0.42 |
| Verification | RH524NM1 | Male | 57 | 2.75 | 25.81 | 0 | 0.41 |
| Verification | RH285NM1 | Male | 47 | 3.53 | 26.02 | 2 | 0.41 |
| Verification | RH270NM1 | Male | 61 | 3.41 | 21.81 | 0 | 0.40 |
| Verification | RH132NM1 | Male | 52 | 13.81 | 34.88 | 5 | 0.39 |
| Verification | RH531NM1 | Male | 56 | 3.55 | 26.95 | 0 | 0.39 |
| Verification | RH561NM1 | Male | 59 | 4.05 | 19.86 | 0 | 0.39 |
| Verification | RH538NM1 | Female | 62 | 1.43 | 22.28 | 3 | 0.39 |
| Verification | RH887NM1 | Male | 58 | 2.58 | 22.53 | 2 | 0.39 |
| Verification | RH604NM1 | Male | 54 | 7.63 | 41.19 | 0 | 0.39 |
| Verification | RH513NM1 | Male | 57 | 1.9 | 28.39 | 0 | 0.39 |
| Verification | RH544NM1 | Male | 57 | 3.5 | 14.87 | 0 | 0.39 |
| Verification | RH563NM1 | Male | 56 | 2.78 | 28.56 | 0 | 0.39 |
| Verification | RH504NM1 | Male | 58 | 3.78 | 23.16 | 0 | 0.39 |
| Verification | RH189NM1 | Male | 56 | 2.2 | 32.17 | 0 | 0.38 |
| Verification | RH288NM1 | Male | 53 | 3.81 | 34.37 | 0 | 0.38 |
| Verification | RH601NM1 | Female | 64 | 4.4 | 19.05 | 0 | 0.38 |
| Verification | RH608NM1 | Male | 54 | 1.11 | 12.72 | 0 | 0.37 |
| Verification | RH257NM1 | Female | 63 | 3.2 | 41.77 | 0 | 0.37 |
| Verification | RH244NM1 | Male | 48 | 1.95 | 40.55 | 0 | 0.37 |
| Verification | RH374NM1 | Male | 68 | 15.66 | 20.99 | 0 | 0.37 |
| Verification | RH170NM1 | Male | 53 | 2.1 | 16.61 | 16 | 0.37 |
| Verification | RH584NM1 | Female | 62 | 3.77 | 14.21 | 0 | 0.37 |
| Verification | RH212NM1 | Male | 55 | 3.86 | 18.97 | 0 | 0.37 |
| Verification | RH577NM1 | Male | 56 | 1.54 | 23.59 | 0 | 0.36 |
| Verification | RH609NM1 | Male | 54 | 2.64 | 23.19 | 0 | 0.35 |
| Verification | RH210NM1 | Male | 54 | 15.6 | 25.06 | 0 | 0.35 |
| Verification | RH214NM1 | Male | 55 | 5 | 24.69 | 0 | 0.35 |
| Verification | RH123NM1 | Male | 54 | 1.78 | 17.32 | 0 | 0.35 |
| Verification | RH233NM1 | Male | 48 | 2.67 | 17 | 0 | 0.34 |
| Verification | RH282NM1 | Male | 50 | 3.57 | 31.48 | 0 | 0.34 |
| Verification | RH253NM1 | Male | 48 | 1.79 | 27.35 | 0 | 0.34 |
| Verification | RH403NM1 | Male | 52 | 14.97 | 20.07 | 0 | 0.34 |
| Verification | RH135NM1 | Male | 55 | 9.62 | 25.77 | 0 | 0.34 |
| Verification | RH592NM1 | Female | 56 | 2.29 | 13.82 | 0 | 0.33 |
| Verification | RH261NM1 | Male | 49 | 3.3 | 26.75 | 0 | 0.33 |
| Verification | RH157NM1 | Male | 46 | 3.09 | 35.34 | 0 | 0.33 |
| Verification | RH129NM1 | Male | 66 | 2.96 | 22.73 | 0 | 0.32 |
| Verification | RH306NM1 | Male | 52 | 2.15 | 27.13 | 0 | 0.32 |
| Verification | RH293NM1 | Male | 52 | 2.32 | 21.19 | 0 | 0.32 |
| Verification | RH434NM1 | Male | 53 | 18.44 | 35.66 | 5 | 0.32 |
| Verification | RH236NM1 | Male | 63 | 2.46 | 18.37 | 0 | 0.32 |
| Verification | RH139NM1 | Male | 49 | 8.84 | 23.1 | 0 | 0.32 |
| Verification | RH510NM1 | Male | 41 | 2.37 | 18.66 | 0 | 0.32 |
| Verification | RH466NM1 | Male | 65 | 13.37 | 19.55 | 0 | 0.32 |
| Verification | RH458NM1 | Male | 42 | 15.11 | 23.07 | 0 | 0.31 |
| Verification | RH128NM1 | Male | 57 | 2.28 | 19.71 | 6 | 0.31 |
| Verification | RH228NM1 | Male | 63 | 2.08 | 30.01 | 0 | 0.31 |
| Verification | RH581NM1 | Male | 62 | 1.71 | 16.49 | 1 | 0.31 |
| Verification | RH179NM1 | Male | 49 | 3.27 | 28.17 | 0 | 0.31 |
| Verification | RH225NM1 | Female | 53 | 2.81 | 18.37 | 0 | 0.31 |
| Verification | RH298NM1 | Male | 63 | 1.36 | 22.73 | 0 | 0.31 |
| Verification | RH535NM1 | Female | 64 | 6.3 | 16.74 | 0 | 0.31 |
| Verification | RH478NM1 | Male | 61 | 1.42 | 27.88 | 0 | 0.30 |
| Verification | RH426NM1 | Male | 55 | 13.56 | 20.14 | 2 | 0.30 |
| Verification | RH124NM1 | Male | 62 | 2.32 | 24.98 | 0 | 0.30 |
| Verification | RH187NM1 | Male | 60 | 4.16 | 21.32 | 0 | 0.30 |
| Verification | RH500NM1 | Male | 57 | 1.57 | 12.08 | 3 | 0.30 |
| Verification | RH281NM1 | Male | 62 | 2.56 | 34.31 | 0 | 0.30 |
| Verification | RH292NM1 | Female | 56 | 1.46 | 16.66 | 0 | 0.30 |
| Verification | RH184NM1 | Female | 67 | 2.18 | 16.44 | 0 | 0.29 |
| Verification | RH198NM1 | Male | 36 | 3.6 | 49.08 | 0 | 0.29 |
| Verification | RH260NM1 | Male | 57 | 0.93 | 24.25 | 2 | 0.29 |
| Verification | RH553NM1 | Male | 59 | 2.11 | 29.62 | 0 | 0.29 |
| Verification | RH502NM1 | Male | 58 | 0.86 | 26.96 | 0 | 0.29 |
| Verification | RH487NM1 | Male | 58 | 2.51 | 17.97 | 0 | 0.28 |
| Verification | RH582NM1 | Male | 57 | 1.66 | 17.91 | 0 | 0.28 |
| Verification | RH501NM1 | Male | 41 | 1.99 | 19.34 | 0 | 0.28 |
| Verification | RH595NM1 | Male | 58 | 7.43 | 25.61 | 0 | 0.28 |
| Verification | RH251NM1 | Male | 36 | 2.11 | 36.96 | 0 | 0.28 |
| Verification | RH493NM1 | Male | 56 | 2.68 | 29.62 | 0 | 0.28 |
| Verification | RH541NM1 | Male | 57 | 4.07 | 22.73 | 1 | 0.28 |
| Verification | RH508NM1 | Male | 56 | 2.74 | 30.58 | 0 | 0.28 |
| Verification | RH559NM1 | Male | 56 | 2.07 | 21.98 | 0 | 0.28 |

TABLE 4-continued

Features and HCC Screening Scores

| Set | ID | Sex | Age | AFP (ng/ml) | DCP (mAU/ml) | Integration of HBV | HCC screening score |
|---|---|---|---|---|---|---|---|
| Verification | RH412NM1 | Male | 54 | 14.51 | 24.03 | 0 | 0.28 |
| Verification | RH591NM1 | Female | 64 | 2.22 | 9.31 | 0 | 0.27 |
| Verification | RH560NM1 | Male | 57 | 2.5 | 22.89 | 0 | 0.27 |
| Verification | RH479NM1 | Male | 59 | 3.14 | 22.15 | 1 | 0.27 |
| Verification | RH568NM1 | Male | 54 | 3.5 | 20.76 | 0 | 0.27 |
| Verification | RH183NM1 | Male | 54 | 2.43 | 23.34 | 0 | 0.27 |
| Verification | RH424NM1 | Male | 56 | 14.78 | 27.02 | 0 | 0.27 |
| Verification | RH558NM1 | Female | 60 | 2.79 | 21.8 | 0 | 0.27 |
| Verification | RH477NM1 | Female | 61 | 3.49 | 34.14 | 0 | 0.27 |
| Verification | RH580NM1 | Male | 56 | 1.51 | 21.19 | 0 | 0.27 |
| Verification | RH204NM1 | Male | 56 | 14.65 | 19.02 | 0 | 0.27 |
| Verification | RH295NM1 | Male | 55 | 2.91 | 33.45 | 0 | 0.27 |
| Verification | RH188NM1 | Male | 55 | 2.55 | 28.05 | 0 | 0.27 |
| Verification | RH517NM1 | Female | 64 | 2.4 | 23.99 | 0 | 0.27 |
| Verification | RH498NM1 | Female | 63 | 1.7 | 15.47 | 0 | 0.27 |
| Verification | RH482NM1 | Female | 55 | 4.99 | 16.62 | 0 | 0.27 |
| Verification | RH484NM1 | Female | 64 | 3.91 | 21.48 | 0 | 0.27 |
| Verification | RH209NM1 | Female | 53 | 15.92 | 17.11 | 1 | 0.27 |
| Verification | RH186NM1 | Male | 53 | 3.98 | 35.35 | 1 | 0.26 |
| Verification | RH199NM1 | Male | 50 | 5.9 | 29.01 | 3 | 0.26 |
| Verification | RH396NM1 | Male | 52 | 15.63 | 22.92 | 2 | 0.26 |
| Verification | RH427NM1 | Male | 54 | 16.9 | 17.53 | 0 | 0.26 |
| Verification | RH489NM1 | Female | 61 | 1.41 | 17.89 | 0 | 0.26 |
| Verification | RH201NM1 | Male | 52 | 17.18 | 32.22 | 2 | 0.26 |
| Verification | RH155NM1 | Male | 57 | 3.17 | 31.42 | 0 | 0.26 |
| Verification | RH272NM1 | Male | 54 | 4.52 | 26.86 | 0 | 0.26 |
| Verification | RH410NM1 | Male | 53 | 13.61 | 15.96 | 0 | 0.26 |
| Verification | RH607NM1 | Male | 54 | 0.96 | 13.53 | 0 | 0.26 |
| Verification | RH548NM1 | Male | 54 | 3.54 | 28.14 | 0 | 0.26 |
| Verification | RH554NM1 | Female | 63 | 2.45 | 22.75 | 0 | 0.26 |
| Verification | RH180NM1 | Male | 55 | 2.88 | 28.71 | 0 | 0.26 |
| Verification | RH596NM1 | Male | 54 | 2.06 | 14.69 | 0 | 0.26 |
| Verification | RH161NM1 | Female | 59 | 3.82 | 32.86 | 1 | 0.26 |
| Verification | RH221NM1 | Male | 53 | 1.98 | 23.59 | 0 | 0.26 |
| Verification | RH525NM1 | Male | 36 | 4.23 | 33.85 | 0 | 0.26 |
| Verification | RH238NM1 | Male | 52 | 4.3 | 23.39 | 0 | 0.26 |
| Verification | RH527NM1 | Male | 54 | 2.96 | 24.11 | 0 | 0.26 |
| Verification | RH203NM1 | Female | 54 | 13.44 | 19.52 | 4 | 0.26 |
| Verification | RH193NM1 | Male | 52 | 2.05 | 21.45 | 0 | 0.26 |
| Verification | RH435NM1 | Male | 50 | 17.08 | 26.45 | 0 | 0.25 |
| Verification | RH598NM1 | Male | 54 | 5.77 | 18.02 | 0 | 0.25 |
| Verification | RH250NM1 | Male | 52 | 3.49 | 27.66 | 0 | 0.25 |
| Verification | RH213NM1 | Female | 62 | 5.38 | 23.02 | 0 | 0.25 |
| Verification | RH528NM1 | Female | 62 | 2.95 | 15.87 | 0 | 0.25 |
| Verification | RH138NM1 | Male | 54 | 7.85 | 20.37 | 0 | 0.25 |
| Verification | RH237NM1 | Male | 53 | 3.01 | 39.92 | 0 | 0.25 |
| Verification | RH605NM1 | Male | 54 | 4.44 | 22.49 | 0 | 0.25 |
| Verification | RH141NM1 | Male | 53 | 2.16 | 16.93 | 0 | 0.25 |
| Verification | RH587NM1 | Female | 62 | 4.44 | 17.1 | 0 | 0.25 |
| Verification | RH401NM1 | Male | 50 | 13.26 | 24.1 | 0 | 0.25 |
| Verification | RH488NM1 | Male | 52 | 2.32 | 30.18 | 0 | 0.25 |
| Verification | RH556NM1 | Female | 61 | 3.18 | 22.32 | 0 | 0.25 |
| Verification | RH255NM1 | Male | 51 | 2.75 | 27.84 | 0 | 0.25 |
| Verification | RH223NM1 | Male | 52 | 3.88 | 29.91 | 0 | 0.25 |
| Verification | RH264NM1 | Male | 51 | 6.13 | 21.66 | 0 | 0.25 |
| Verification | RH505NM1 | Female | 60 | 3.6 | 24.54 | 0 | 0.25 |
| Verification | RH509NM1 | Male | 54 | 8.07 | 26.43 | 0 | 0.25 |
| Verification | RH146NM1 | Male | 51 | 3.46 | 20.43 | 0 | 0.25 |
| Verification | RH130NM1 | Male | 52 | 2.65 | 22.66 | 0 | 0.24 |
| Verification | RH144NM1 | Male | 53 | 5.08 | 12.67 | 0 | 0.24 |
| Verification | RH162NM1 | Male | 50 | 3.8 | 24.03 | 1 | 0.24 |
| Verification | RH181NM1 | Male | 50 | 1.87 | 16.01 | 0 | 0.24 |
| Verification | RH594NM1 | Female | 55 | 2.98 | 10.76 | 0 | 0.24 |
| Verification | RH530NM1 | Male | 49 | 1.52 | 30.57 | 0 | 0.24 |
| Verification | RH590NM1 | Female | 55 | 1.5 | 18.13 | 2 | 0.24 |
| Verification | RH432NM1 | Female | 55 | 15.87 | 15.73 | 2 | 0.24 |
| Verification | RH242NM1 | Male | 49 | 3.23 | 29.49 | 0 | 0.24 |
| Verification | RH491NM1 | Male | 49 | 1.96 | 23.8 | 0 | 0.24 |
| Verification | RH533NM1 | Male | 49 | 3.3 | 29.42 | 0 | 0.24 |
| Verification | RH439NM1 | Male | 51 | 19.17 | 18.41 | 0 | 0.24 |
| Verification | RH231NM1 | Male | 48 | 2.1 | 30.67 | 0 | 0.24 |
| Verification | RH499NM1 | Male | 49 | 3.39 | 23.15 | 0 | 0.24 |
| Verification | RH514NM1 | Male | 36 | 2.26 | 28.7 | 14 | 0.24 |
| Verification | RH526NM1 | Male | 49 | 2.08 | 19.73 | 0 | 0.23 |
| Verification | RH555NM1 | Female | 53 | 2.69 | 21.57 | 1 | 0.23 |

TABLE 4-continued

Features and HCC Screening Scores

| Set | ID | Sex | Age | AFP (ng/ml) | DCP (mAU/ml) | Integration of HBV | HCC screening score |
|---|---|---|---|---|---|---|---|
| Verification | RH588NM1 | Female | 55 | 1.61 | 20.94 | 0 | 0.23 |
| Verification | RH131NM1 | Male | 50 | 2.93 | 23.61 | 0 | 0.23 |
| Verification | RH222NM1 | Female | 58 | 2.88 | 26.78 | 0 | 0.23 |
| Verification | RH200NM1 | Male | 46 | 1.81 | 27.14 | 0 | 0.23 |
| Verification | RH254NM1 | Female | 54 | 1.66 | 22.02 | 1 | 0.23 |
| Verification | RH243NM1 | Male | 47 | 4.07 | 26.27 | 1 | 0.23 |
| Verification | RH274NM1 | Male | 47 | 1.52 | 19.41 | 0 | 0.22 |
| Verification | RH536NM1 | Female | 53 | 2.11 | 28.92 | 0 | 0.22 |
| Verification | RH125NM1 | Male | 33 | 3.93 | 17.06 | 1 | 0.22 |
| Verification | RH278NM1 | Male | 48 | 3.1 | 22.88 | 0 | 0.22 |
| Verification | RH166NM1 | Male | 48 | 4.47 | 22.97 | 0 | 0.22 |
| Verification | RH543NM1 | Female | 55 | 2.36 | 15.04 | 1 | 0.22 |
| Verification | RH271NM1 | Male | 47 | 0.98 | 34.09 | 0 | 0.22 |
| Verification | RH185NM1 | Male | 46 | 2.15 | 29.04 | 0 | 0.22 |
| Verification | RH490NM1 | Female | 54 | 1.9 | 19.2 | 2 | 0.22 |
| Verification | RH516NM1 | Female | 55 | 5.17 | 22.27 | 2 | 0.22 |
| Verification | RH405NM1 | Female | 65 | 17.53 | 15.92 | 0 | 0.22 |
| Verification | RH294NM1 | Male | 46 | 3.24 | 32.01 | 0 | 0.22 |
| Verification | RH494NM1 | Female | 54 | 2.37 | 17.81 | 0 | 0.21 |
| Verification | RH136NM1 | Male | 36 | 12.68 | 28.69 | 7 | 0.21 |
| Verification | RH252NM1 | Male | 43 | 3.27 | 25.93 | 0 | 0.21 |
| Verification | RH297NM1 | Female | 54 | 3.62 | 32.87 | 0 | 0.21 |
| Verification | RH407NM1 | Male | 42 | 13.64 | 15.6 | 1 | 0.21 |
| Verification | RH191NM1 | Male | 38 | 4.22 | 24.95 | 6 | 0.21 |
| Verification | RH886NM1 | Male | 44 | 3.45 | 21.43 | 0 | 0.21 |
| Verification | RH284NM1 | Male | 44 | 3.92 | 31.48 | 0 | 0.21 |
| Verification | RH149NM1 | Male | 43 | 8.65 | 31.79 | 1 | 0.21 |
| Verification | RH133NM1 | Male | 44 | 1.61 | 26.58 | 0 | 0.20 |
| Verification | RH557NM1 | Male | 41 | 2.91 | 26.01 | 1 | 0.20 |
| Verification | RH164NM1 | Female | 51 | 2.41 | 28.09 | 0 | 0.20 |
| Verification | RH126NM1 | Female | 53 | 3.09 | 20.78 | 0 | 0.20 |
| Verification | RH515NM1 | Male | 41 | 2.15 | 26.53 | 0 | 0.20 |
| Verification | RH229NM1 | Male | 42 | 4.07 | 32.05 | 0 | 0.20 |
| Verification | RH269NM1 | Female | 65 | 2.22 | 25.13 | 0 | 0.20 |
| Verification | RH266NM1 | Female | 50 | 3.11 | 23.83 | 0 | 0.20 |
| Verification | RH296NM1 | Male | 41 | 1.27 | 32.69 | 0 | 0.20 |
| Verification | RH503NM1 | Female | 61 | 1.41 | 17.82 | 3 | 0.20 |
| Verification | RH569NM1 | Female | 64 | 2.38 | 21.4 | 0 | 0.20 |
| Verification | RH153NM1 | Male | 42 | 3.16 | 32.1 | 0 | 0.19 |
| Verification | RH589NM1 | Male | 38 | 2.92 | 20.92 | 1 | 0.19 |
| Verification | RH258NM1 | Female | 48 | 3.29 | 24.33 | 0 | 0.19 |
| Verification | RH579NM1 | Female | 64 | 4.56 | 16.66 | 0 | 0.19 |
| Verification | RH599NM1 | Female | 64 | 1.26 | 12 | 0 | 0.19 |
| Verification | RH143NM1 | Male | 39 | 3.54 | 22.75 | 2 | 0.19 |
| Verification | RH475NM1 | Male | 38 | 4.4 | 37.77 | 0 | 0.19 |
| Verification | RH522NM1 | Female | 64 | 1.76 | 18.42 | 0 | 0.19 |
| Verification | RH549NM1 | Female | 60 | 1.76 | 18.12 | 1 | 0.19 |
| Verification | RH575NM1 | Female | 63 | 2.42 | 20.98 | 1 | 0.19 |
| Verification | RH305NM1 | Female | 64 | 1.75 | 20.89 | 0 | 0.19 |
| Verification | RH468NM1 | Female | 63 | 2.78 | 20.5 | 0 | 0.19 |
| Verification | RH436NM1 | Male | 38 | 16.36 | 19.13 | 0 | 0.18 |
| Verification | RH194NM1 | Male | 40 | 2.33 | 27.23 | 0 | 0.18 |
| Verification | RH140NM1 | Male | 40 | 5.3 | 19.03 | 0 | 0.18 |
| Verification | RH546NM1 | Male | 38 | 5.64 | 24.16 | 0 | 0.18 |
| Verification | RH154NM1 | Female | 52 | 1.76 | 18.6 | 0 | 0.18 |
| Verification | RH606NM1 | Male | 38 | 2.83 | 22.97 | 0 | 0.18 |
| Verification | RH551NM1 | Male | 36 | 1.78 | 23.58 | 0 | 0.18 |
| Verification | RH570NM1 | Female | 62 | 3.45 | 19.93 | 0 | 0.18 |
| Verification | RH392NM1 | Female | 56 | 19.98 | 18.75 | 0 | 0.18 |
| Verification | RH265NM1 | Male | 38 | 4.26 | 33.54 | 0 | 0.18 |
| Verification | RH597NM1 | Male | 36 | 7.3 | 25.73 | 0 | 0.18 |
| Verification | RH496NM1 | Male | 38 | 1.27 | 22.8 | 0 | 0.18 |
| Verification | RH262NM1 | Female | 62 | 1.37 | 27.32 | 0 | 0.18 |
| Verification | RH603NM1 | Male | 36 | 1.82 | 18.81 | 0 | 0.18 |
| Verification | RH472NM1 | Female | 60 | 1.97 | 17.64 | 0 | 0.17 |
| Verification | RH521NM1 | Male | 36 | 1.6 | 28.7 | 0 | 0.17 |
| Verification | RH246NM1 | Female | 60 | 4.59 | 29.63 | 0 | 0.17 |
| Verification | RH299NM1 | Male | 36 | 2.9 | 31.31 | 1 | 0.17 |
| Verification | RH552NM1 | Female | 60 | 1.42 | 15.27 | 0 | 0.17 |
| Verification | RH148NM1 | Male | 35 | 3.6 | 23.41 | 1 | 0.17 |
| Verification | RH218NM1 | Female | 59 | 2.16 | 16.93 | 0 | 0.17 |
| Verification | RH196NM1 | Female | 59 | 4.78 | 22.83 | 0 | 0.17 |
| Verification | RH216NM1 | Female | 59 | 2.52 | 26.61 | 0 | 0.17 |
| Verification | RH480NM1 | Female | 55 | 1.62 | 23.12 | 1 | 0.17 |
| Verification | RH217NM1 | Female | 58 | 6.52 | 24.03 | 0 | 0.16 |

TABLE 4-continued

Features and HCC Screening Scores

| Set | ID | Sex | Age | AFP (ng/ml) | DCP (mAU/ml) | Integration of HBV | HCC screening score |
|---|---|---|---|---|---|---|---|
| Verification | RH247NM1 | Female | 57 | 3.92 | 23.54 | 0 | 0.16 |
| Verification | RH234NM1 | Female | 54 | 3.12 | 17.35 | 1 | 0.16 |
| Verification | RH366NM1 | Female | 53 | 13.99 | 17.71 | 2 | 0.16 |
| Verification | RH519NM1 | Female | 56 | 1.64 | 17.45 | 0 | 0.16 |
| Verification | RH593NM1 | Female | 56 | 2.86 | 16.52 | 1 | 0.16 |
| Verification | RH289NM1 | Female | 57 | 3.59 | 25.28 | 0 | 0.16 |
| Verification | RH562NM1 | Female | 55 | 2.08 | 15.23 | 0 | 0.16 |
| Verification | RH273NM1 | Female | 56 | 2.4 | 20.84 | 0 | 0.16 |
| Verification | RH182NM1 | Female | 56 | 3.69 | 21.44 | 0 | 0.16 |
| Verification | RH248NM1 | Female | 56 | 2.25 | 19.02 | 0 | 0.16 |
| Verification | RH301NM1 | Female | 57 | 1.75 | 20.74 | 0 | 0.16 |
| Verification | RH518NM1 | Female | 54 | 2.83 | 14.04 | 1 | 0.16 |
| Verification | RH571NM1 | Female | 56 | 1.53 | 16.8 | 0 | 0.16 |
| Verification | RH208NM1 | Female | 56 | 15.29 | 26.95 | 0 | 0.16 |
| Verification | RH572NM1 | Female | 56 | 2.65 | 21.36 | 0 | 0.16 |
| Verification | RH287NM1 | Female | 58 | 1.46 | 25.61 | 0 | 0.16 |
| Verification | RH532NM1 | Female | 56 | 0.81 | 23.2 | 0 | 0.16 |
| Verification | RH539NM1 | Female | 55 | 2.26 | 16.71 | 0 | 0.16 |
| Verification | RH565NM1 | Female | 56 | 1.6 | 19.47 | 0 | 0.16 |
| Verification | RH537NM1 | Female | 55 | 2.13 | 15.97 | 0 | 0.16 |
| Verification | RH417NM1 | Female | 53 | 15.07 | 18.15 | 0 | 0.16 |
| Verification | RH578NM1 | Female | 55 | 1.28 | 13.94 | 0 | 0.16 |
| Verification | RH241NM1 | Female | 54 | 1.88 | 23.32 | 0 | 0.15 |
| Verification | RH249NM1 | Female | 53 | 1.13 | 15.42 | 1 | 0.15 |
| Verification | RH279NM1 | Female | 39 | 5.33 | 21.11 | 0 | 0.15 |
| Verification | RH512NM1 | Female | 54 | 1.06 | 17.58 | 0 | 0.15 |
| Verification | RH240NM1 | Female | 55 | 3 | 18.34 | 0 | 0.15 |
| Verification | RH574NM1 | Female | 55 | 5.21 | 13.02 | 0 | 0.15 |
| Verification | RH576NM1 | Female | 55 | 4.48 | 19.62 | 0 | 0.15 |
| Verification | RH226NM1 | Female | 54 | 3.08 | 20.57 | 0 | 0.15 |
| Verification | RH583NM1 | Female | 55 | 1.69 | 25.96 | 0 | 0.15 |
| Verification | RH276NM1 | Female | 54 | 1.38 | 27.72 | 0 | 0.15 |
| Verification | RH267NM1 | Female | 52 | 1.99 | 26.19 | 1 | 0.15 |
| Verification | RH230NM1 | Female | 52 | 3.21 | 29.43 | 1 | 0.15 |
| Verification | RH545NM1 | Female | 54 | 2.73 | 22.64 | 0 | 0.15 |
| Verification | RH215NM1 | Female | 55 | 3.27 | 17.81 | 0 | 0.15 |
| Verification | RH207NM1 | Female | 53 | 14.22 | 17.78 | 1 | 0.15 |
| Verification | RH275NM1 | Female | 52 | 1.38 | 19.49 | 0 | 0.15 |
| Verification | RH534NM1 | Female | 53 | 2.76 | 14.37 | 0 | 0.15 |
| Verification | RH485NM1 | Female | 53 | 2.2 | 27.14 | 0 | 0.15 |
| Verification | RH483NM1 | Female | 54 | 3.25 | 19.87 | 0 | 0.15 |
| Verification | RH495NM1 | Female | 53 | 2.67 | 15.79 | 0 | 0.15 |
| Verification | RH474NM1 | Female | 53 | 1.75 | 12.4 | 0 | 0.15 |
| Verification | RH529NM1 | Female | 53 | 2.56 | 8.1 | 0 | 0.15 |
| Verification | RH268NM1 | Female | 55 | 2.07 | 25.48 | 0 | 0.15 |
| Verification | RH471NM1 | Female | 54 | 2.16 | 17.71 | 0 | 0.15 |
| Verification | RH550NM1 | Female | 53 | 2.27 | 19.35 | 0 | 0.15 |
| Verification | RH304NM1 | Female | 54 | 1.52 | 25.4 | 0 | 0.14 |
| Verification | RH235NM1 | Female | 53 | 4.36 | 12.99 | 0 | 0.14 |
| Verification | RH190NM1 | Female | 55 | 4.32 | 32.9 | 0 | 0.14 |
| Verification | RH168NM1 | Female | 45 | 6.75 | 15.35 | 4 | 0.14 |
| Verification | RH307NM1 | Female | 52 | 2.63 | 28.23 | 0 | 0.14 |
| Verification | RH470NM1 | Female | 53 | 2.37 | 18.46 | 0 | 0.14 |
| Verification | RH263NM1 | Female | 52 | 1.69 | 21.26 | 0 | 0.14 |
| Verification | RH277NM1 | Female | 51 | 1.6 | 26.39 | 0 | 0.14 |
| Verification | RH302NM1 | Female | 52 | 1.31 | 23.82 | 0 | 0.14 |
| Verification | RH220NM1 | Female | 53 | 1.7 | 30.17 | 0 | 0.14 |
| Verification | RH300NM1 | Female | 52 | 1.68 | 22.56 | 0 | 0.14 |
| Verification | RH160NM1 | Female | 47 | 2.78 | 23.67 | 1 | 0.13 |
| Verification | RH167NM1 | Female | 48 | 3.51 | 12.67 | 0 | 0.12 |
| Verification | RH159NM1 | Female | 46 | 1.66 | 16.96 | 1 | 0.12 |
| Verification | RH303NM1 | Female | 46 | 3.2 | 20.53 | 0 | 0.12 |
| Verification | RH286NM1 | Female | 47 | 4.07 | 25.63 | 0 | 0.12 |
| Verification | RH197NM1 | Female | 41 | 1.47 | 22.41 | 0 | 0.11 |
| Verification | RH205NM1 | Female | 40 | 15.39 | 24.66 | 0 | 0.11 |
| Verification | RH150NM1 | Female | 44 | 3.23 | 26.22 | 0 | 0.11 |
| Verification | RH169NM1 | Female | 42 | 2.28 | 24.44 | 0 | 0.11 |
| Verification | RH202NM1 | Female | 38 | 15.31 | 20.12 | 0 | 0.11 |
| Verification | RH195NM1 | Female | 42 | 2.15 | 25.92 | 0 | 0.11 |
| Verification | RH239NM1 | Female | 40 | 0.79 | 12.75 | 0 | 0.10 |
| Verification | RH573NM1 | Female | 38 | 4.85 | 22.26 | 0 | 0.10 |
| Verification | RH290NM1 | Female | 39 | 3.11 | 23.66 | 0 | 0.10 |
| Verification | RH542NM1 | Female | 38 | 5.96 | 13.98 | 0 | 0.10 |
| Verification | RH492NM1 | Female | 38 | 1.93 | 14.9 | 0 | 0.10 |
| Verification | RH511NM1 | Female | 30 | 1.35 | 16.76 | 4 | 0.10 |

TABLE 4-continued

Features and HCC Screening Scores

| Set | ID | Sex | Age | AFP (ng/ml) | DCP (mAU/ml) | Integration of HBV | HCC screening score |
|---|---|---|---|---|---|---|---|
| Verification | RH219NM1 | Female | 38 | 2.69 | 16.22 | 0 | 0.10 |
| Verification | RH158NM1 | Female | 37 | 2.72 | 20.02 | 1 | 0.10 |
| Verification | RH259NM1 | Female | 36 | 2.71 | 29.6 | 0 | 0.10 |
| Verification | RH224NM1 | Female | 25 | 2.19 | 19.47 | 0 | 0.09 |
| Verification | RH600NM1 | Female | 33 | 17.02 | 11.83 | 0 | 0.09 |
| Verification | RH586NM1 | Female | 32 | 3.5 | 20.84 | 0 | 0.09 |
| Verification | RH473NM1 | Female | 32 | 1.53 | 28.35 | 1 | 0.08 |
| Verification | RH566NM1 | Female | 29 | 2.06 | 23.29 | 0 | 0.08 |
| Verification | RH211NM1 | Female | 29 | 5.32 | 18.37 | 0 | 0.08 |
| Verification | RH497NM1 | Female | 30 | 1.82 | 23.8 | 0 | 0.08 |
| Verification | RH192NM1 | Female | 27 | 3.46 | 18.49 | 0 | 0.08 |

TABLE 5

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RG869NM1 | CTNNB1 | 3 | 41266097 | 41266097 | Missense_mutant | SNPyr | G | T | p.Asp32Tyr | 15482 | 0.14094 | T |
| RG876NM1 | CTNNB1 | 3 | 41266097 | 41266097 | Missense_mutant | SNP | G | A | p.Asp32Asn | 10552 | 0.02104 | T |
| RG895NM1 | CTNNB1 | 3 | 41266098 | 41266098 | Missense_mutant | SNP | A | G | p.Asp32Gly | 16286 | 0.06981 | T |
| RG898NM1 | CTNNB1 | 3 | 41266098 | 41266098 | Missense_mutant | SNP | A | C | p.Asp32Ala | 12768 | 0.00368 | T |
| RH455NM1 | CTNNB1 | 3 | 41266098 | 41266098 | Missense_mutant | SNP | A | C | p.Asp32Ala | 27189 | 0.00614 | T |
| RH903NM1 | CTNNB1 | 3 | 41266098 | 41266098 | Missense_mutant | SNP | A | G | p.Asp32Gly | 18374 | 0.10977 | T |
| RH29INM1 | CTNNB1 | 3 | 41266098 | 41266099 | Frame shift_mutant | INS | — | CTCTGGAATCCATTCTGGTG | p.Thr40LeufsTer14 | 7021 | 0.00057 | S |
| RG878NM1 | CTNNB1 | 3 | 41266101 | 41266101 | Missense_mutant | SNP | C | T | p.Ser33Phe | 14749 | 0.00183 | T |
| RG892NM1 | CTNNB1 | 3 | 41266101 | 41266101 | Missense_mutant | SNP | C | G | p.Ser33Cys | 13683 | 0.00132 | T |
| RH443NM1 | CTNNB1 | 3 | 41266101 | 41266101 | Missense_mutant | SNP | C | G | p.Ser33Cys | 7430 | 0.09273 | T |
| RH897NM1 | CTNNB1 | 3 | 41266101 | 41266101 | Missense_mutant | SNP | C | G | p.Ser33Cys | 12413 | 0.00161 | T |
| RG898NM1 | CTNNB1 | 3 | 41266103 | 41266103 | Missense_mutant | SNP | G | A | p.Gly34Arg | 12790 | 0.00719 | T |
| RH443NM1 | CTNNB1 | 3 | 41266103 | 41266103 | Missense_mutant | SNP | G | A | p.Gly34Arg | 7462 | 0.00161 | T |
| RH897NM1 | CTNNB1 | 3 | 41266104 | 41266104 | Missense_mutant | SNP | T | A | p.Gly34Glu | 12421 | 0.00177 | T |
| RH455NM1 | CTNNB1 | 3 | 41266107 | 41266107 | Missense_mutant | SNP | T | G | p.Ile35Ser | 25818 | 0.0024 | T |
| RG878NM1 | CTNNB1 | 3 | 41266112 | 41266112 | Missense_mutant | SNP | T | G | p.Ser37Ala | 14741 | 0.00224 | T |
| RH891NM1 | CTNNB1 | 3 | 41266112 | 41266112 | Missense_mutant | SNP | T | G | p.Ser37Ala | 9288 | 0.04339 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH385NM1 | CTNNB1 | 3 | 41266118 | 41266118 | Missense_mutant | SNP | G | A | p.Ala39Thr | 23624 | 0.00063 | T |
| RH377NM1 | CTNNB1 | 3 | 41266124 | 41266124 | Missense_mutant | SNP | A | G | p.Thr41Ala | 8948 | 0.00257 | T |
| RH897NM1 | CTNNB1 | 3 | 41266124 | 41266124 | Missense_mutant | SNP | A | G | p.Thr41Ala | 12499 | 0.07609 | T |
| RG886NM1 | CTNNB1 | 3 | 41266137 | 41266137 | Missense_mutant | SNP | C | T | p.Ser45Phe | 15325 | 0.00548 | T |
| RH393NM1 | CTNNB1 | 3 | 41266188 | 41266188 | Missense_mutant | SNP | T | A | p.Val62Asp | 6129 | 0.00196 | T |
| RG774NM1 | TERT | 5 | 1295228 | 1295228 | Upstream_gene_mutatnt | SNP | G | A | • | 5383 | 0.00985 | T |
| RG785NM1 | TERT | 5 | 1295228 | 1295228 | Upstream_gene_mutant | SNP | G | A | • | 3910 | 0.1243 | T |
| RG796NM1 | TERT | 5 | 1295228 | 1295228 | Upstream_gene_mutant | SNP | G | A | • | 4015 | 0.02441 | T |
| RG869NM1 | TERT | 5 | 1295228 | 1295228 | Upstream_gene_mutatnt | SNP | G | A | • | 5323 | 0.19218 | T |
| RG895NM1 | TERT | 5 | 1295228 | 1295228 | Upstream_gene_mutant | SNP | G | A | • | 7720 | 0.00687 | T |
| RG898NM1 | TERT | 5 | 1295228 | 1295228 | Upstream_gene_mutant | SNP | G | A | • | 4848 | 0.03032 | T |
| RH337NM1 | TERT | 5 | 1295228 | 1295228 | Upstream_gene_mutatnt | SNP | G | A | • | 6437 | 0.03387 | T |
| RH414NM1 | TERT | 5 | 1295228 | 1295228 | Upstream_gene_mutant | SNP | G | A | • | 5393 | 0.01558 | T |
| RH419NM1 | TERT | 5 | 1295228 | 1295228 | Upstream_gene_mutant | SNP | G | A | • | 5450 | 0.00991 | T |
| RH443NM1 | TERT | 5 | 1295228 | 1295228 | Upstream_gene_mutatnt | SNP | G | A | • | 2793 | 0.09273 | T |
| RH900NM1 | TERT | 5 | 1295228 | 1295228 | Upstream_gene_mutant | SNP | G | A | • | 3078 | 0.05458 | T |
| RG870NM1 | TERT | 5 | 1295228 | 1295228 | Upstream_gene_mutant | SNP | G | A | • | 9595 | 0.00125 | T |
| RG871NM1 | TERT | 5 | 1295228 | 1295228 | Upstream_gene_mutatnt | SNP | G | A | • | 6380 | 0.00188 | T |
| RG874NM1 | TERT | 5 | 1295228 | 1295228 | Upstream_gene_mutant | SNP | G | A | • | 2935 | 0.00136 | S |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RG878NM1 | TERT | 5 | 1295228 | 1295228 | Upstream_gene_mutant | SNP | G | A | • | 7791 | 0.00539 | T |
| RH314NM1 | TERT | 5 | 1295228 | 1295228 | Upstream_gene_mutatnt | SNP | G | A | • | 2338 | 0.00257 | S |
| RH137NM1 | TERT | 5 | 1295228 | 1295228 | Upstream_gene_mutant | SNP | G | A | • | 5818 | 0.00103 | S |
| RH227NM1 | TERT | 5 | 1295228 | 1295228 | Upstream_gene_mutant | SNP | G | A | • | 1886 | 0.00212 | S |
| RH767NM1 | TERT | 5 | 1295228 | 1295228 | Upstream_gene_mutant | SNP | G | A | • | 3387 | 0.00118 | S |
| RH397NM1 | TERT | 5 | 1295228 | 1295228 | Upstream_gene_mutant | SNP | G | A | • | 2539 | 0.0067 | T |
| RH398NM1 | TERT | 5 | 1295228 | 1295228 | Upstream_gene_mutant | SNP | G | A | • | 1979 | 0.00303 | S |
| RH421NM1 | TERT | 5 | 1295228 | 1295228 | Upstream_gene_mutant | SNP | G | A | • | 4764 | 0.01721 | T |
| RH905NM1 | TERT | 5 | 1295228 | 1295228 | Upstream_gene_mutant | SNP | G | A | • | 5136 | 0.00136 | S |
| RH455NM1 | TERT | 5 | 1295250 | 1295250 | Upstream_gene_mutant | SNP | G | A | • | 2542 | 0.03029 | T |
| RG872NM1 | TERT | 5 | 1295250 | 1295250 | Upstream_gene_mutant | SNP | G | A | • | 5786 | 0.00069 | S |
| RH397NM1 | TERT | 5 | 1295250 | 1295250 | Upstream_gene_mutant | SNP | G | T | • | 2463 | 0.00162 | S |
| RH878NM1 | TERT | 5 | 1295250 | 1295250 | Upstream_gene_mutant | SNP | G | A | • | 9659 | 0.00145 | T |
| RH390NM1 | AXIN1 | 16 | 347141 | 347141 | stop_gained | SNP | C | A | p.Glu624Ter | 25046 | 0.00104 | T |
| RH240NM1 | AXIN1 | 16 | 347213 | 347213 | Missense_mutant | SNP | C | T | p.Val600Met | 1804 | 0.0061 | T |
| RH204NM1 | AXIN1 | 16 | 347883 | 347883 | inframe-deletion | DEL | GTGGTGGACGTGTG | — | p.His538_His541del | 5822 | 0.00052 | S |
| RH436NM1 | AXIN1 | 16 | 347892 | 347892 | inframe-deletion | DEL | GTG | — | p.His538del | 10162 | 0.00059 | S |
| RH471NM1 | AXIN1 | 16 | 347892 | 347894 | inframe-deletion | DEL | GTG | — | p.His538del | 6743 | 0.00104 | S |
| RH526NM1 | AXIN1 | 16 | 347924 | 347924 | Missense_mutant | SNP | C | T | p.Gly528Ser | 8043 | 0.00124 | T |
| RH393NM1 | AXIN1 | 16 | 347992 | 347992 | Missense_mutant | SNP | G | A | p.Ala505Val | 6645 | 0.00181 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH878NM1 | AXIN1 | 16 | 348100 | 348100 | Frame shift_mutant | DEL | CT | — | p.Ser469HisfsTer121 | 8295 | 0.00084 | S |
| RH397NM1 | AXIN1 | 16 | 348113 | 348113 | stop_gained | SNP | C | A | p.Glu465Ter | 10014 | 0.02676 | T |
| RH882NM1 | AXIN1 | 16 | 348131 | 348131 | Missense_mutant | SNP | G | T | p.Leu459Ile | 8915 | 0.00112 | T |
| RH196NM1 | AXIN1 | 16 | 348182 | 348182 | Missense_mutant | SNP | G | T | p.Pro442Thr | 7668 | 0.0013 | T |
| RH147NM1 | AXIN1 | 16 | 348217 | 348231 | inframe-deletion | DEL | CCTGACGATGGATCG | — | p.Asp426_Gly430del | 7573 | 0.00053 | S |
| RG790NM1 | AXIN1 | 16 | 348230 | 348230 | Missense_mutant | SNP | C | T | p.Asp426Asn | 9229 | 0.0013 | T |
| RH289NM1 | AXIN1 | 16 | 348230 | 348320 | Missense_mutant | SNP | C | T | p.Asp426Asn | 5106 | 0.00196 | T |
| RH544NM1 | AXIN1 | 16 | 348241 | 348241 | Missense_mutant | SNP | C | T | p.Gly422Asp | 1995 | 0.5198 | T |
| RH385NM1 | AXIN1 | 16 | 396164 | 396164 | stop_gained | SNP | C | A | p.Glu288Ter | 10142 | 0.00552 | T |
| RH464NM1 | AXIN1 | 16 | 396303 | 396303 | Missense_mutant | SNP | T | A | p.Leu241Phe | 4894 | 0.00204 | T |
| RG904NM1 | AXIN1 | 16 | 396567 | 396579 | Frame shift_mutant | DEL | ATTGTTATCAAGA | — | p.Ile149MetfsTer16 | 2710 | 0.00148 | S |
| RH455NM1 | AXIN1 | 16 | 396589 | 396589 | Missense_mutant | SNP | C | T | p.Arg146Gln | 23251 | 0.00099 | T |
| RH390NM1 | AXIN1 | 16 | 396590 | 396590 | stop_gained | SNP | G | A | p.Arg146Ter | 24009 | 0.16215 | T |
| RH479NM1 | AXIN1 | 16 | 396671 | 396671 | Missense_mutant | SNP | A | C | p.Phe119Val | 4564 | 0.00219 | T |
| RH394NM1 | AXIN1 | 16 | 396740 | 396740 | stop_gained | SNP | G | A | p.Gln96Ter | 6063 | 0.04519 | T |
| RH285NM1 | AXIN1 | 16 | 396799 | 396799 | Missense_mutant | SNP | G | A | p.Ala76Val | 5638 | 0.00177 | T |
| RH490NM1 | TP53 | 17 | 7572941 | 7572948 | Frame shift_mutant | DEL | GCCCTTCT | — | p.Glu388Ter | 15405 | 0.00052 | T |
| RG879NM1 | TP53 | 17 | 7572973 | 7572973 | Missense_mutant | SNP | C | T | p.Arg379His | 7895 | 0.00127 | T |
| RG905NM1 | TP53 | 17 | 7572973 | 7572973 | Missense_mutant | SNP | C | T | p.Arg379His | 9475 | 0.00116 | T |
| RH291NM1 | TP53 | 17 | 7572973 | 7572973 | Missense_mutant | SNP | C | T | p.Arg379His | 4685 | 0.00256 | T |
| RH455NM1 | TP53 | 17 | 7572973 | 7572973 | Missense_mutant | SNP | C | T | p.Arg379His | 4991 | 0.002 | T |
| RH476NM1 | TP53 | 17 | 7572973 | 7572973 | Missense_mutant | SNP | C | T | p.Arg379His | 6230 | 0.00257 | T |
| RH906NM1 | TP53 | 17 | 7572973 | 7572973 | Missense_mutant | SNP | C | T | p.Arg379His | 6614 | 0.00151 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH393NM1 | TP53 | 17 | 7572974 | 7572974 | Missense_mutant | SNP | G | A | p.Arg379Cys | 7234 | 0.00166 | T |
| RH884NM1 | TP53 | 17 | 7573944 | 7573944 | Frame shift_mutant | DEL | C | — | p.Ser362AlafsTer8 | 8458 | 0.0013 | T |
| RH538NM1 | TP53 | 17 | 7573946 | 7573946 | Missense_mutant | SNP | C | G | p.Gly361Arg | 14281 | 0.00329 | T |
| RH224NM1 | TP53 | 17 | 7573975 | 7573975 | Missense_mutant | SNP | T | A | p.Lys351Met | 9886 | 0.00101 | T |
| RH292NM1 | TP53 | 17 | 7573992 | 7573993 | Frame shift_mutant | DEL | AT | — | p.Asn345ArgfsTer36 | 13985 | 0.00057 | T |
| RH528NM1 | TP53 | 17 | 7574012 | 7574012 | Missense_mutant | SNP | C | T | p.Glu339Lys | 10347 | 0.00106 | T |
| RG883NM1 | TP53 | 17 | 7574024 | 7574026 | Splice_receptor_mutant | DEL | GCCCACGGATCTGCAGCAACAGA | — | — | 11423 | 0.03589 | T |
| RG878NM1 | TP53 | 17 | 7574030 | 7574030 | Frame shift_mutant | DEL | G | — | p.Arg333ValfsTer12 | 13047 | 0.00376 | T |
| RH288NM1 | TP53 | 17 | 7574030 | 7574030 | Missense_mutant | SNP | G | A | p.Arg333Cys | 3538 | 0.00283 | T |
| RH225NM1 | TP53 | 17 | 7574032 | 7574032 | Missense_mutant | SNP | A | T | p.Ile332Asn | 12577 | 0.00119 | T |
| RH233NM1 | TP53 | 17 | 7576897 | 7576898 | Frame shift_mutant | DEL | GG | — | p.Gln317AlafsTer19 | 2531 | 0.00237 | T |
| RH425NM1 | TP53 | 17 | 7576909 | 7576909 | Missense_mutant | SNP | T | A | p.Ser313Cys | 10333 | 0.00116 | T |
| RH520NM1 | TP53 | 17 | 7576909 | 7576909 | Missense_mutant | SNP | T | A | p.Ser313Cys | 9468 | 0.00106 | T |
| RH608NM1 | TP53 | 17 | 7577021 | 7577021 | Missense_mutant | SNP | C | T | p.Arg306Gln | 6632 | 0.00181 | T |
| RH440NM1 | TP53 | 17 | 7577046 | 7577046 | stop_gained | SNP | C | A | p.Glu298Ter | 27867 | 0.0084 | T |
| RH391NM1 | TP53 | 17 | 7577046 | 7577046 | Missense_mutant | SNP | C | T | p.Glu298Lys | 9238 | 0.0013 | T |
| RH170NM1 | TP53 | 17 | 7577061 | 7577061 | Missense_mutant | SNP | C | G | p.Gly293Arg | 5419 | 0.59125 | T |
| RH455NM1 | TP53 | 17 | 7577105 | 7577105 | Missense_mutant | SNP | G | T | p.Pro278His | 10238 | 0.00107 | T |
| RH891NM1 | TP53 | 17 | 7577120 | 7577120 | Missense_mutant | SNP | C | A | p.Arg273Leu | 5439 | 0.06803 | T |
| RH602NM1 | TP53 | 17 | 7577124 | 7577124 | Missense_mutant | SNP | C | T | p.Val272Met | 2726 | 0.01101 | T |
| RH567NM1 | TP53 | 17 | 7577127 | 7577127 | stop_gained | SNP | C | A | p.Glu271Ter | 9377 | 0.00149 | T |
| RG805NM1 | TP53 | 17 | 7577130 | 7577130 | Missense_mutant | SNP | A | G | p.Phe270Leu | 2370 | 0.00506 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH256NM1 | TP53 | 17 | 7577138 | 7577138 | Missense_mutant | SNP | C | T | p.Arg267Gln | 6643 | 0.00151 | T |
| RH482NM1 | TP53 | 17 | 7577157 | 7577157 | Splice_receptor_mutant | SNP | T | A | • | 23254 | 0.0258 | T |
| RH390NM1 | TP53 | 17 | 7577498 | 7577498 | Splice_receptor_mutant | SNP | C | A | • | 17162 | 0.123 | T |
| RH419NM1 | TP53 | 17 | 7577498 | 7577498 | Splice_receptor_mutant | SNP | C | A | • | 12474 | 0.0364 | T |
| RH517NM1 | TP53 | 17 | 7577512 | 7577513 | Frame shift_mutant | DEL | GT | — | p.Leu257GlyfsTer6 | 6982 | 0.00086 | S |
| RH543NM1 | TP53 | 17 | 7577512 | 7577513 | Frame shift_mutant | DEL | GT | — | p.Lcu257GlyfsTer6 | 9582 | 0.00063 | S |
| RH592NM1 | TP53 | 17 | 7577512 | 7577513 | Frame shift_mutant | DEL | GT | — | p.Leu257GlyfsTer6 | 9177 | 0.00087 | S |
| RH285NM1 | TP53 | 17 | 7577513 | 7577517 | Frame shift_mutant | DEL | TGTGA | — | p.Ile255TrfsTer7 | 5420 | 0.00129 | S |
| RH554NM1 | TP53 | 17 | 7577521 | 7577521 | Missense_mutant | SNP | T | A | p.Ile254Phe | 15857 | 0.00107 | T |
| RH489NM1 | TP53 | 17 | 7577533 | 7577533 | Missense_mutant | DNP | GC | AA | p.ArgPro249SerSer | — | — | T |
| RG792NM1 | TP53 | 17 | 7577534 | 7577534 | Missense_mutant | SNP | C | A | p.Arg249Ser | 2930 | 0.00239 | S |
| RG796NM1 | TP53 | 17 | 7577534 | 7577534 | Missense_mutant | SNP | C | A | p.Arg249Ser | 3809 | 0.6905 | T |
| RG868NM1 | TP53 | 17 | 7577534 | 7577534 | Missense_mutant | SNP | C | A | p.Arg249Ser | 11902 | 0.00202 | T |
| RG871NM1 | TP53 | 17 | 7577534 | 7577534 | Missense_mutant | SNP | C | A | p.Arg249Ser | 16130 | 0.00087 | S |
| RG872NM1 | TP53 | 17 | 7577534 | 7577534 | Missense_mutant | SNP | C | A | p.Arg249Ser | 13678 | 0.1471 | T |
| RG873NM1 | TP53 | 17 | 7577534 | 7577534 | Missense_mutant | SNP | C | A | p.Arg249Ser | 24 | 0.41667 | T |
| RG881NM1 | TP53 | 17 | 7577534 | 7577534 | Missense_mutant | SNP | C | A | p.Arg249Ser | 12881 | 0.12173 | T |
| RG898NM1 | TP53 | 17 | 7577534 | 7577534 | Missense_mutant | SNP | C | A | p.Arg249Ser | 11673 | 0.11642 | T |
| RG904NM1 | TP53 | 17 | 7577534 | 7577534 | Missense_mutant | SNP | C | A | p.Arg249Ser | 7355 | 0.00761 | T |
| RH127NM1 | TP53 | 17 | 7577534 | 7577534 | Missense_mutant | SNP | C | A | p.Arg249Ser | 13235 | 0.00159 | T |
| RH147NM1 | TP53 | 17 | 7577534 | 7577534 | Missense_mutant | SNP | C | A | p.Arg249Ser | 6822 | 0.00191 | T |
| RH161NM1 | TP53 | 17 | 7577534 | 7577534 | Missense_mutant | SNP | C | A | p.Arg249Ser | 12989 | 0.00269 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH165NM1 | TP53 | 17 | 7577534 | 7577534 | Missense_mutant | SNP | C | A | p.Arg249Ser | 13453 | 0.00164 | T |
| RH184NM1 | TP53 | 17 | 7577534 | 7577534 | Missense_mutant | SNP | C | A | p.Arg249Ser | 12568 | 0.00064 | S |
| RH189NM1 | TP53 | 17 | 7577534 | 7577534 | Missense_mutant | SNP | C | A | p.Arg249Ser | 6244 | 0.00096 | S |
| RH206NM1 | TP53 | 17 | 7577534 | 7577534 | Missense_mutant | SNP | C | A | p.Arg249Ser | 7731 | 0.00414 | T |
| RH209NM1 | TP53 | 17 | 7577534 | 7577534 | Missense_mutant | SNP | C | A | p.Arg249Ser | 13992 | 0.00522 | T |
| RH225NM1 | TP53 | 17 | 7577534 | 7577534 | Missense_mutant | SNP | C | A | p.Arg249Ser | 14626 | 0.00137 | T |
| RH254NM1 | TP53 | 17 | 7577534 | 7577534 | Missense_mutant | SNP | C | A | p.Arg249Ser | 7519 | 0.0008 | S |
| RH297NM1 | TP53 | 17 | 7577534 | 7577534 | Missense_mutant | SNP | C | A | p.Arg249Ser | 8745 | 0.00183 | T |
| RH382NM1 | TP53 | 17 | 7577534 | 7577534 | Missense_mutant | SNP | C | A | p.Arg249Ser | 6799 | 0.00088 | S |
| RH390NM1 | TP53 | 17 | 7577534 | 7577534 | Missense_mutant | SNP | C | A | p.Arg249Ser | 19293 | 0.00218 | T |
| RH394NM1 | TP53 | 17 | 7577534 | 7577534 | Missense_mutant | SNP | C | A | p.Arg249Ser | 20891 | 0.24029 | T |
| RH400NM1 | TP53 | 17 | 7577534 | 7577534 | Missense_mutant | SNP | C | A | p.Arg249Ser | 18462 | 0.00179 | T |
| RH408NM1 | TP53 | 17 | 7577534 | 7577534 | Missense_mutant | SNP | C | A | p.Arg249Ser | 5540 | 0.00487 | T |
| RH414NM1 | TP53 | 17 | 7577534 | 7577534 | Missense_mutant | SNP | C | A | p.Arg249Ser | 11987 | 0.02553 | T |
| RH421NM1 | TP53 | 17 | 7577534 | 7577534 | Missense_mutant | SNP | C | A | p.Arg249Ser | 15021 | 0.03322 | T |
| RH425NM1 | TP53 | 17 | 7577534 | 7577534 | Missense_mutant | SNP | C | A | p.Arg249Ser | 11484 | 0.00192 | T |
| RH437NM1 | TP53 | 17 | 7577534 | 7577534 | Missense_mutant | SNP | C | A | p.Arg249Ser | 13230 | 0.00121 | T |
| RH458NM1 | TP53 | 17 | 7577534 | 7577534 | Missense_mutant | SNP | C | A | p.Arg249Ser | 13197 | 0.00174 | T |
| RH462NM1 | TP53 | 17 | 7577534 | 7577534 | Missense_mutant | SNP | C | A | p.Arg249Ser | 20608 | 0.00558 | T |
| RH477NM1 | TP53 | 17 | 7577534 | 7577534 | Missense_mutant | SNP | C | A | p.Arg249Ser | 17912 | 0.00167 | T |
| RH524NM1 | TP53 | 17 | 7577534 | 7577534 | Missense_mutant | SNP | C | A | p.Arg249Ser | 6466 | 0.00325 | T |
| RH536NM1 | TP53 | 17 | 7577534 | 7577534 | Missense_mutant | SNP | C | A | p.Arg249Ser | 10568 | 0.00076 | S |
| RH538NM1 | TP53 | 17 | 7577534 | 7577534 | Missense_mutant | SNP | C | A | p.Arg249Ser | 13225 | 0.00227 | T |
| RH555NM1 | TP53 | 17 | 7577534 | 7577534 | Missense_mutant | SNP | C | A | p.Arg249Ser | 18797 | 0.0009 | T |
| RH555NM1 | TP53 | 17 | 7577534 | 7577534 | Missense_mutant | SNP | C | A | p.Arg249Ser | 14168 | 0.00113 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH563NM1 | TP53 | 17 | 7577534 | 7577534 | Missense_mutant | SNP | C | A | p.Arg249Ser | 7361 | 0.00163 | T |
| RH585NM1 | TP53 | 17 | 7577534 | 7577534 | Missense_mutant | SNP | C | A | p.Arg249Ser | 8974 | 0.001 | S |
| RH588NM1 | TP53 | 17 | 7577534 | 7577534 | Missense_mutant | SNP | C | A | p.Arg249Ser | 9004 | 0.00056 | S |
| RH590NM1 | TP53 | 17 | 7577534 | 7577534 | Missense_mutant | SNP | C | A | p.Arg249Ser | 10106 | 0.00119 | T |
| RH885NM1 | TP53 | 17 | 7577534 | 7577534 | Missense_mutant | SNP | C | A | p.Arg249Ser | 14022 | 0.00107 | T |
| RH910NM1 | TP53 | 17 | 7577534 | 7577534 | Missense_mutant | SNP | C | A | p.Arg249Ser | 19048 | 0.00121 | T |
| RH776NM1 | TP53 | 17 | 7577534 | 7577534 | Missense_mutant | SNP | C | A | p.Arg249Ser | 3236 | 0.00216 | S |
| RH126NM1 | TP53 | 17 | 7577534 | 7577534 | Missense_mutant | SNP | C | A | p.Arg249Ser | 10958 | 0.00064 | S |
| RH134NM1 | TP53 | 17 | 7577534 | 7577534 | Missense_mutant | SNP | C | A | p.Arg249Ser | 7769 | 0.00051 | S |
| RH135NM1 | TP53 | 17 | 7577534 | 7577534 | Missense_mutant | SNP | C | A | p.Arg249Ser | 15182 | 0.00059 | S |
| RH139NM1 | TP53 | 17 | 7577534 | 7577534 | Missense_mutant | SNP | C | A | p.Arg249Ser | 10639 | 0.00132 | T |
| RH164NM1 | TP53 | 17 | 7577534 | 7577534 | Missense_mutant | SNP | C | A | p.Arg249Ser | 12422 | 0.00089 | S |
| RH179NM1 | TP53 | 17 | 7577534 | 7577534 | Missense_mutant | SNP | C | A | p.Arg249Ser | 10474 | 0.00057 | S |
| RH210NM1 | TP53 | 17 | 7577534 | 7577534 | Missense_mutant | SNP | C | A | p.Arg249Ser | 10764 | 0.00056 | S |
| RH217NM1 | TP53 | 17 | 7577534 | 7577534 | Missense_mutant | SNP | C | A | p.Arg249Ser | 14319 | 0.00112 | T |
| RH213NM1 | TP53 | 17 | 7577534 | 7577534 | Missense_mutant | SNP | C | A | p.Arg249Ser | 9069 | 0.00066 | S |
| RH214NM1 | TP53 | 17 | 7577534 | 7577534 | Missense_mutant | SNP | C | A | p.Arg249Ser | 7381 | 0.00054 | S |
| RH222NM1 | TP53 | 17 | 7577534 | 7577534 | Missense_mutant | SNP | C | A | p.Arg249Ser | 7241 | 0.00055 | S |
| RH232NM1 | TP53 | 17 | 7577534 | 7577534 | Missense_mutant | SNP | C | A | p.Arg249Ser | 4309 | 0.00162 | S |
| RH258NM1 | TP53 | 17 | 7577534 | 7577534 | Missense_mutant | SNP | C | A | p.Arg249Ser | 5106 | 0.00118 | S |
| RH266NM1 | TP53 | 17 | 7577534 | 7577534 | Missense_mutant | SNP | C | A | p.Arg249Ser | 7249 | 0.00083 | S |
| RH270NM1 | TP53 | 17 | 7577534 | 7577534 | Missense_mutant | SNP | C | A | p.Arg249Ser | 8245 | 0.00073 | S |
| RH282NM1 | TP53 | 17 | 7577534 | 7577534 | Missense_mutant | SNP | C | A | p.Arg249Ser | 4035 | 0.00099 | S |
| RH285NM1 | TP53 | 17 | 7577534 | 7577534 | Missense_mutant | SNP | C | A | p.Arg249Ser | 5717 | 0.00052 | S |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH291NM1 | TP53 | 17 | 7577534 | 7577534 | Missense_mutant | SNP | C | A | p.Arg249Ser | 8306 | 0.00072 | S |
| RH293NM1 | TP53 | 17 | 7577534 | 7577534 | Missense_mutant | SNP | C | A | p.Arg249Ser | 7117 | 0.00056 | S |
| RH306NM1 | TP53 | 17 | 7577534 | 7577534 | Missense_mutant | SNP | C | A | p.Arg249Ser | 8901 | 0.00067 | S |
| RH377NM1 | TP53 | 17 | 7577534 | 7577534 | Missense_mutant | SNP | C | A | p.Arg249Ser | 9732 | 0.00062 | S |
| RH378NM1 | TP53 | 17 | 7577534 | 7577534 | Missense_mutant | SNP | C | A | p.Arg249Ser | 25942 | 0.00054 | S |
| RH383NM1 | TP53 | 17 | 7577534 | 7577534 | Missense_mutant | SNP | C | A | p.Arg249Ser | 11353 | 0.0007 | S |
| RH391NM1 | TP53 | 17 | 7577534 | 7577534 | Missense_mutant | SNP | C | A | p.Arg249Ser | 7490 | 0.00053 | S |
| RH403NM1 | TP53 | 17 | 7577534 | 7577534 | Missense_mutant | SNP | C | A | p.Arg249Ser | 16461 | 0.00067 | S |
| RH418NM1 | TP53 | 17 | 7577534 | 7577534 | Missense_mutant | SNP | C | A | p.Arg249Ser | 10085 | 0.00099 | S |
| RH432NM1 | TP53 | 17 | 7577534 | 7577534 | Missense_mutant | SNP | C | A | p.Arg249Ser | 22124 | 0.0005 | S |
| RH438NM1 | TP53 | 17 | 7577534 | 7577534 | Missense_mutant | SNP | C | A | p.Arg249Ser | 12114 | 0.00157 | T |
| RH476NM1 | TP53 | 17 | 7577534 | 7577534 | Missense_mutant | SNP | C | A | p.Arg249Ser | 13744 | 0.00073 | S |
| RH484NM1 | TP53 | 17 | 7577534 | 7577534 | Missense_mutant | SNP | C | A | p.Arg249Ser | 16634 | 0.00078 | S |
| RH494NM1 | TP53 | 17 | 7577534 | 7577534 | Missense_mutant | SNP | C | A | p.Arg249Ser | 12254 | 0.00065 | S |
| RH498NM1 | TP53 | 17 | 7577534 | 7577534 | Missense_mutant | SNP | C | A | p.Arg249Ser | 13967 | 0.001 | T |
| RH516NM1 | TP53 | 17 | 7577534 | 7577534 | Missense_mutant | SNP | C | A | p.Arg249Ser | 16660 | 0.00072 | S |
| RH520NM1 | TP53 | 17 | 7577534 | 7577534 | Missense_mutant | SNP | C | A | p.Arg249Ser | 11725 | 0.00051 | S |
| RH525NM1 | TP53 | 17 | 7577534 | 7577534 | Missense_mutant | SNP | C | A | p.Arg249Ser | 5044 | 0.00119 | S |
| RH544NM1 | TP53 | 17 | 7577534 | 7577534 | Missense_mutant | SNP | C | A | p.Arg249Ser | 4331 | 0.00092 | S |
| RH547NM1 | TP53 | 17 | 7577534 | 7577534 | Missense_mutant | SNP | C | G | p.Arg249Ser | 7950 | 0.0005 | S |
| RH556NM1 | TP53 | 17 | 7577534 | 7577534 | Missense_mutant | SNP | C | A | p.Arg249Ser | 7393 | 0.00054 | S |
| RH567NM1 | TP53 | 17 | 7577534 | 7577534 | Missense_mutant | SNP | C | A | p.Arg249Ser | 9371 | 0.00107 | T |
| RH577NM1 | TP53 | 17 | 7577534 | 7577534 | Missense_mutant | SNP | C | A | p.Arg249Ser | 8006 | 0.0005 | S |
| RH584NM1 | TP53 | 17 | 7577534 | 7577534 | Missense_mutant | SNP | C | A | p.Arg249Ser | 8223 | 0.00073 | S |
| RH587NM1 | TP53 | 17 | 7577534 | 7577534 | Missense_mutant | SNP | C | A | p.Arg249Ser | 15256 | 0.00079 | S |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH591NM1 | TP53 | 17 | 7577534 | 7577534 | Missense_mutant | SNP | C | A | p.Arg249Ser | 6472 | 0.00062 | S |
| RH592NM1 | TP53 | 17 | 7577534 | 7577534 | Missense_mutant | SNP | C | A | p.Arg249Ser | 9781 | 0.00153 | T |
| RH594NM1 | TP53 | 17 | 7577534 | 7577534 | Missense_mutant | SNP | C | A | p.Arg249Ser | 4762 | 0.00168 | S |
| RH601NM1 | TP53 | 17 | 7577534 | 7577534 | Missense_mutant | SNP | C | A | p.Arg249Ser | 11149 | 0.0009 | S |
| RH889NM1 | TP53 | 17 | 7577534 | 7577534 | Missense_mutant | SNP | C | A | p.Arg249Ser | 12370 | 0.00129 | T |
| RH915NM1 | TP53 | 17 | 7577534 | 7577534 | Missense_mutant | SNP | C | A | p.Arg249Ser | 10781 | 0.00074 | S |
| RH535NM1 | TP53 | 17 | 7577539 | 7577539 | Missense_mutant | SNP | G | A | p.Arg248Trp | 14917 | 0.00469 | T |
| RH547NM1 | TP53 | 17 | 7577539 | 7577539 | Missense_mutant | SNP | G | A | p.Arg248Trp | 7941 | 0.00201 | T |
| RH397NM1 | TP53 | 17 | 7577545 | 7577545 | Missense_mutant | SNP | T | A | p.Met246Leu | 11578 | 0.241 | T |
| RH165NM1 | TP53 | 17 | 7577548 | 7577548 | Missense_mutant | SNP | C | T | p.Gly245Ser | 23427 | 0.00107 | T |
| RH395NM1 | TP53 | 17 | 7577556 | 7577556 | Missense_mutant | SNP | C | T | p.Cys242Tyr | 19634 | 0.00148 | T |
| RH253NM1 | TP53 | 17 | 7577559 | 7577559 | Missense_mutant | SNP | G | A | p.Ser241Phe | 6521 | 0.00184 | T |
| RH430NM1 | TP53 | 17 | 7577559 | 7577559 | Missense_mutant | SNP | G | A | p.Ser241Phe | 33409 | 0.00054 | T |
| RH513NM1 | TP53 | 17 | 7577562 | 7577562 | Missense_mutant | SNP | C | A | p.Ser240Ile | 8502 | 0.00141 | T |
| RH154NM1 | TP53 | 17 | 7577574 | 7577574 | Missense_mutant | SNP | T | A | p.Tyr236Phe | 12368 | 0.00113 | T |
| RH251NM1 | TP53 | 17 | 7577576 | 7577578 | inframe_deletion | DEL | GTT | — | p.Asn235del | 1930 | 0.00363 | S |
| RH871NM1 | TP53 | 17 | 7577580 | 7577580 | Missense_mutant | SNP | T | C | p.Tyr234Cys | 17951 | 0.01382 | T |
| RH292NM1 | TP53 | 17 | 7577591 | 7577591 | Frame shift_mutant | DEL | G | — | p.Thr231rofsTer16 | 9011 | 0.00133 | T |
| RH125NM1 | TP53 | 17 | 7577605 | 7577605 | Missense_mutant | SNP | C | A | p.Gly226Cys | 10295 | 0.00107 | T |
| RH203NM1 | TP53 | 17 | 7578190 | 7578190 | Missense_mutant | SNP | T | C | p.Tyr220Cys | 14947 | 0.00167 | T |
| RH601NM1 | TP53 | 17 | 7578190 | 7578190 | Missense_mutant | SNP | T | C | p.Tyr220Cys | 8908 | 0.00135 | T |
| RH876NM1 | TP53 | 17 | 7578203 | 7578203 | Missense_mutant | SNP | C | A | p.Val216Leu | 9888 | 0.02164 | T |
| RH132NM1 | TP53 | 17 | 7578203 | 7578203 | Missense_mutant | SNP | C | T | p.Val216Met | 11507 | 0.00235 | T |
| RH157NM1 | TP53 | 17 | 7578203 | 7578203 | Missense_mutant | SNP | C | T | p.Val216Met | 8730 | 0.0047 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RH897NM1 | TP53 | 17 | 7578211 | 7578211 | Missense_mutant | SNP | C | A | p.Arg213 Leu | 12348 | 0.13233 | T |
| RH887NM1 | TP53 | 17 | 7578212 | 7578212 | stop_gained | SNP | G | A | p.Arg213 Ter | 8479 | 0.0013 | T |
| RH385NM1 | TP53 | 17 | 7578249 | 7578250 | Frame shift_mutant | SNP | — | T | p.Asn200 LysfsTer9 | 19036 | 0.13259 | T |
| RH279NM1 | TP53 | 17 | 7578275 | 7578275 | inframe_deletion | DEL | GAG | — | p.Pro191 del | 4678 | 0.00128 | S |
| RH419NM1 | TP53 | 17 | 7578275 | 7578277 | inframe_deletion | DEL | GAG | — | p.Pro191 del | 9472 | 0.00063 | S |
| RH505NM1 | TP53 | 17 | 7578389 | 7578389 | Missense_mutant | SNP | G | A | p.Arg181 Cys | 11519 | 0.00234 | T |
| RH398NM1 | TP53 | 17 | 7578392 | 7578392 | stop_gained | SNP | C | A | p.Glu180 Ter | 8482 | 0.00236 | T |
| RG888NM1 | TP53 | 17 | 7578395 | 7578395 | Missense_mutant | SNP | G | A | p.His179 Tyr | 9505 | 0.0041 | T |
| RH584NM1 | TP53 | 17 | 7578401 | 7578401 | Missense_mutant | SNP | G | A | p.Pro177 Ser | 8925 | 0.00157 | T |
| RH501NM1 | TP53 | 17 | 7578404 | 7578404 | Missense_mutant | SNP | A | T | p.Cys176 Ser | 8920 | 0.00112 | T |
| RH510NM1 | TP53 | 17 | 7578406 | 7578406 | Missense_mutant | SNP | C | T | p.Arg175 His | 8880 | 0.00439 | T |
| RH531NM1 | TP53 | 17 | 7578406 | 7578406 | Missense_mutant | SNP | C | T | p.Arg175 His | 13146 | 0.00198 | T |
| RH291NM1 | TP53 | 17 | 7578406 | 7578406 | Missense_mutant | SNP | C | T | p.Arg175 His | 9654 | 0.00104 | T |
| RH585NM1 | TP53 | 17 | 7578415 | 7578415 | Missense_mutant | SNP | A | C | p.VaL172 Gly | 9844 | 0.01199 | T |
| RH380NM1 | TP53 | 17 | 7578457 | 7578457 | Missense_mutant | SNP | C | T | p.Arg158 His | 14377 | 0.02379 | T |
| RG785NM1 | TP53 | 17 | 7578461 | 7578461 | Missense_mutant | SNP | C | A | p.Val157 Phe | 195 | 0.18974 | T |
| RG868NM1 | TP53 | 17 | 7578461 | 7578461 | Missense_mutant | SNP | C | A | p.Val157 Phe | 13247 | 0.03616 | T |
| RH443NM1 | TP53 | 17 | 7578461 | 7578461 | Missense_mutant | SNP | C | A | p.Val157 Phe | 8078 | 0.24016 | T |
| RH257NM1 | TP53 | 17 | 7578461 | 7578461 | Missense_mutant | SNP | C | T | p.Val157 Ile | 20862 | 0.00096 | T |
| RH884NM1 | TP53 | 17 | 7578461 | 7578461 | Missense_mutant | SNP | C | T | p.Val157 Ile | 8403 | 0.00119 | T |
| RH609NM1 | TP53 | 17 | 7578473 | 7578474 | Frame shift_mutant | DEL | GC | — | p.Pro153 ArgfsTer27 | 6235 | 0.00096 | S |
| RG871NM1 | TP53 | 17 | 7578475 | 7578475 | Missense_mutant | SNP | G | A | p.Pro152 Leu | 16849 | 0.00142 | T |
| RH256NM1 | TP53 | 17 | 7578475 | 7578475 | Missense_mutant | SNP | G | A | p.Pro152 Leu | 9341 | 0.00214 | T |
| RH900NM1 | TP53 | 17 | 7578479 | 7578479 | Missense_mutant | SNP | G | T | p.Pro51 Thr | 9799 | 0.09327 | T |

TABLE 5-continued

Mutation information

| Sample_ID | Gene_name | Chromosome | Start position | End position | Mutant_classification | Mutant_type | Ref | Alt | Protein_change | Tumor_depth | Tumor_frequency | Grade* |
|---|---|---|---|---|---|---|---|---|---|---|---|---|
| RG888NM1 | TP53 | 17 | 7578491 | 7578491 | Missense_mutant | SNP | C | T | p.Val147Ile | 7539 | 0.00172 | T |
| RH261NM1 | TP53 | 17 | 7578491 | 7578492 | Frame shift_mutant | DEL | CC | — | p.Trp146CysfsTer2 | 5257 | 0.00114 | S |
| RH561NM1 | TP53 | 17 | 7578503 | 7578503 | Missense_mutant | SNP | C | T | p.Val143Met | 7723 | 0.00142 | T |
| RH379NM1 | TP53 | 17 | 7578518 | 7578518 | Missense_mutant | SNP | C | T | p.Ala138Thr | 7529 | 0.00133 | T |
| RG878NM1 | TP53 | 17 | 7578538 | 7578538 | Missense_mutant | SNP | T | A | p.Asn131Ile | 10345 | 0.00203 | T |
| RG892NM1 | TP53 | 17 | 7579329 | 7579329 | Missense_mutant | SNP | T | C | p.Lys120Glu | 9102 | 0.00132 | T |
| RG452NM1 | TP53 | 17 | 7579340 | 7579340 | Missense_mutant | SNP | G | A | p.Ser116Phe | 12029 | 0.00116 | T |
| RG886NM1 | TP53 | 17 | 7579358 | 7579358 | Missense_mutant | SNP | C | T | p.Arg110His | 10193 | 0.00108 | T |
| RH123NM1 | TP53 | 17 | 7579363 | 7579371 | inframe_deletion | DEL | ACCGTAGCT | — | p.Ser106_Gly108del | 4671 | 0.00128 | S |
| RH291NM1 | TP53 | 17 | 7879395 | 7879395 | Missense_mutant | SNP | G | A | p.Pro98Ser | 3686 | 0.00461 | T |
| RG899NM1 | TP53 | 17 | 7579401 | 7579401 | Missense_mutant | DEL | A | C | p.Ser96Ala | 4181 | 0.00239 | T |
| RH504NM1 | TP53 | 17 | 7579414 | 7579414 | Frame shift_mutant | SNP | C | — | p.Trp91CysfsTer32 | 10839 | 0.0012 | T |
| RG898NM1 | TP53 | 17 | 7579473 | 7579473 | Missense_mutant | SNP | G | C | p.Pro72Ala | 8312 | 0.5409 | T |
| RH585NM1 | TP53 | 17 | 7579479 | 7579482 | Frame shift_mutant | DEL | CAGC | — | p.Ala69LeufsTer53 | 7638 | 0.00079 | S |
| RH589NM1 | TP53 | 17 | 7579482 | 7579482 | Missense_mutant | SNP | C | T | p.Ala69Thr | 2773 | 0.49189 | T |
| RH256NM1 | TP53 | 17 | 9579482 | 9579483 | Frame shift_mutant | DEL | CC | — | p.Glu68AspfsTer80 | 6245 | 0.00096 | S |
| RG871NM1 | TP53 | 17 | 7579536 | 7579536 | stop_gained | SNP | C | A | p.Glu51Ter | 10547 | 0.00114 | T |
| RG870NM1 | TP53 | 17 | 7579722 | 7579722 | Splice_receptor_mutant | SNP | C | G | • | 14884 | 0.0043 | T |
| RK137NX1 | TP53 | 17 | 7577534 | 7577534 | Missense_mutant | SNP | C | A | p.Arg249Ser | 6726 | 0.00059 | S |
| RK139NX1 | TP53 | 17 | 7577534 | 7577534 | Missense_mutant | SNP | C | A | p.Arg249Ser | 10385 | 0.00077 | S |
| RG145NX1 | TP53 | 17 | 7577534 | 7577534 | Missense_mutant | SNP | C | A | p.Arg249Ser | 6670 | 0.0009 | S |
| RK149NX1 | TP53 | 17 | 7577534 | 7577534 | Missense_mutant | SNP | C | A | p.Arg249Ser | 7490 | 0.0008 | S |
| RK155NX1 | TP53 | 17 | 7577534 | 7577534 | Missense_mutant | SNP | C | A | p.Arg249Ser | 6279 | 0.00064 | S |

TABLE 5-continued

| | | | | | Mutation information | | | | | | | |
|---|---|---|---|---|---|---|---|---|---|---|---|---|
| Sample_ ID | Gene_ name | Chromosome | Start position | End position | Mutant_ classification | Mutant_ type | Ref | Alt | Protein_ change | Tumor_ depth | Tumor_ frequency | Grade* |
| RK170NX1 | TP53 | 17 | 7577534 | 7577534 | Missense_ mutant | SNP | C | A | p.Arg249 Ser | 5786 | 0.00138 | S |

*t represents a true mutation; S represents a suspected mutation.

Example 4. Predictive Value of Early HCC of AFP/US Negative Individuals by HCC Screening Assay The invention further tests whether HCC screening can detect HCC from AFP/US negative and HBsAg positive individuals without clinical symptoms. 331 AFP/US negative individuals were tested with HCC screening and 24 positive cases (referred to as HCC screening positive) were identified based on the algorithm from the training set (FIG. 4D).

24 HCC screening positive individuals were followed up for 6-8 months to obtain clinical results of HCC. Of these individuals, 17 were examined by dynamic CT, 4 by AFP/US and 3 by telephone interview. 4 of the 24 screened HCC positive individuals were eventually diagnosed as HCC, with a positive predictive value of HCC detection being 17% (FIG. 4E). In addition, a group of HCC screening negative participants (n=70) agreed to have a dynamic CT test at 6-8 months, and no one was diagnosed with HCC. The present invention also tracked 172 HCC screening negative participants by AFP/US 6-8 months after baseline AFP/US screening and no HCC cases were diagnosed. Of the 65 participants followed up by telephone interviews, no HCC patients were found (FIG. 2). Overall, no HCC cases were found in these HCC screening negative cases. Taken together, the HCC screening assay produced a positive predictive value of 17%, a sensitivity of 100% (4/4), and a specificity of 94% (307/327) in AFP/US negative individuals (FIG. 4F). All 4 HCC patients identified had tumor sizes <3 cm when diagnosed by dynamic CT (FIG. 4G), and these 4 patients had no cirrhosis based on US results at baseline.

The present invention provides AFP/US examinations within 6-8 months after baseline testing to 944 participants who were AFP/US-negative at baseline and who did not have an HCC screening test. Four HCC cases were detected and further confirmed (0.4%, 4/944). Cancer registration records showed that no liver cancer results were identified in these 337 participants before Jun. 30, 2018 (ICD-10 Code C22), who were AFP/US negative in baseline screening and did not undergo HCC screening or any further AFP/US screening (FIG. 2).

6-8 months after the first blood sampling at baseline, 13 of the 24 HCC screening positive cases underwent a second blood drawing to repeat the HCC screening assay. One of the HCC cases continued to be positive and the score was higher than 6 months ago. Another case of HCC that had been surgically resected prior to the second blood drawing showed negative HCC screening consistent with this condition. Of the 11 HCC screening positive non-HCC cases, 7 (64%) were negative in the second HCC screening test, although two of the screening results were close to the threshold (0.40). The remaining 4 non-HCC cases were still positive in the second HCC screening (FIG. 4E). These results indicate that the positive predictive value can be further improved by repeating the test at the second time point. These cases are currently followed up to further validate the assay.

Example 5. Training a Liquid Biopsy Assay with Healthy Individuals

The HCC screening assay shows strong HCC recognition ability in high-risk populations. Previous studies have predicted that sensitivity and specificity may be lower in such high-risk populations than in cancer patients compared to healthy individuals without HBV infection or other risk factors. In order to test this hypothesis, in the invention HCC screening was performed on 70 healthy individuals without HBV infection (HBsAg negative), and these data was used to replace 70 HBsAg positive non-HCC cases in the training set. Through analysis of cfDNA and protein markers, the HCC screening assay effectively recognized HCC cases from healthy individuals with a sensitivity of 98% and specificity of 100% (FIG. 5A). However, the algorithm derived from this training set (HCC and healthy individuals) does not perform well in HBsAg positive non-HCC cases. According to this algorithm, most non-HCC cases are classified as positive, while HCC and non-HCC cases are highly overlapping (FIG. 5B). In addition, validation sets do not perform well. Although all four HCC cases were positive in the test, many of the HBsAg (+) individuals were classified as positive, resulting in specificity and positive predictive values of only 58% and 2.8%, respectively (FIG. 5B). On the other hand, the algorithm derived from the case of HCC and non-HCC correctly classified all healthy individuals (100%) as negative, except for their performance in the HBsAg positive validation set (FIG. 5B).

Example 6. Liquid Biopsy Assay Further Including CNV

I. Obtaining a Blood Sample

Blood samples from patients with liver cancer were provided from 65 patients with liver cancer who had been clinically identified as liver cancer.

The blood samples of patients with high risk of liver cancer were provided by 70 patients with high risk of liver cancer who were identified as high risk of liver cancer by the methods provided in the literature (Omata, M., et al., Asia-Pacific clinical practice guidelines on the management of hepatocellular carcinoma: a 2017 update. Hepatol Int, 2017.11(4):p. 317-370.).

Healthy human blood samples were provided by 100 healthy volunteers.

II. Detection of Liver Cancer Mutation Genes in cfDNA of Blood Samples to be Detected and CNV Detection The blood samples to be detected are 65 liver cancer patient blood samples, 70 liver cancer high-risk patient blood samples and 100 healthy person blood samples.

1. The cfDNA of blood samples to be detected was extracted by MagMAX™ Cell-Free DNA Isolation Kit respectively.

2. After completing step 1, liquid phase hybridization capture technique was used to detect the mutation information of liver cancer gene in cfDNA of blood sample to be detected, such as the mutation information of TP53 gene, AXIN1 gene, CTNNB1 gene, promoter of TERT gene, B-type HBV and C-type HBV. The specific steps are as follows:

(1) Taking the cfDNA of the blood sample to be detected) and constructing a library by using a KAPA Hyper Prep kit to obtain the cfDNA library of the blood sample to be detected.

(2) After completing step (1), taking a cfDNA library of the blood sample to be detected, performing hybridization capture of target region by using a sureselect XT target capture kit, and sequencing on an Illumina platform with a sequencing depth of 20000×. The versions, chromosomes, start positions, stop positions and coverage areas of the genes or viruses detected are detailed in Table 6.

TABLE 6

| Gene or virus | Version | Chromosome | Start position | Stop-position | Coverage area |
|---|---|---|---|---|---|
| TP53 gene | HG19 | 17 | 7572927 | 7579884 | TP53 gene exon full length |
| AXIN1 gene | HG19 | 16 | 338122 | 397000 | AXIN1 gene exon full length |
| CTNNB1 gene | HG19 | 3 | 41265560 | 41281237 | CTNNB1 gene exon full length |
| TERT gene | HG19 | 5 | 1295228 | 1295250 | Positions 228 and 250 of the TERT gene promoter |
| Hepatitis B virus type C | AF533983 | 1 | 1 | 3215 | Full length of type C HBV genome |
| Type B HBV | AB602818 | 1 | 1 | 3215 | Full length of type B HBV genome |

The detection results of liver cancer mutant genes in cfDNA of some blood samples to be detected are shown in columns 2 and 4 of Table 7.

TABLE 7

| Number | Mutant gene mutation frequency | HBV integration score | HBV integration gene |
|---|---|---|---|
| HCCscreen01 | — | B | KLF4; BUB1; HMHB1; F13B; LRFN2 |
| HCCscreen02 | TERT\|1.2%; TP53\|3.7% | A | PKDCC; SNTG1; AFF4 |
| HCCscreen03 | TP53\|0.2% | — | — |
| HCCscreen04 | TERT\|1.1%; TP53\|8.4% | A | GLP2R; ZNF438; HMGXB3; FGB; COL23A1 |
| HCCscreen05 | TERT\|19%; TP53\|21%; AXIN1\|1.5%; CTNNB1\|1% | — | — |
| HCCscreen06 | — | B | TERT; RAPGEF2; FSTL5 |
| HCCscreen07 | — | A | COL22A1; LRRC31; SAMD7 |
| HCCscreen08 | CTNNB1\|0.3% | B | SEPT7P2 |
| HCCscreen09 | TP53\|1.2%; AXIN1\|0.2% | A | KMT2B; TERT; MTRNR2L1; SLC26A7; RUNX1T1 |
| HCCscreen10 | TP53\|0.1% | B | LOC100288788; IQSEC3 |
| HCCscreen11 | — | C | PBX1; LMX1A |
| HCCscreen12 | — | — | — |
| HCCscreen13 | TERT\|1.6%; CTNNB1\|6.7% | A | SAMD11; TERT; LINC01511; LOC10192; LOC102467213 |
| HCCscreen14 | TP53\|0.3% | — | — |
| HCCscreen15 | TP53\|0.1%; CTNNB1\|0.1% | C | CWH43 |
| HCCscreen16 | TERT\|3%; CTNNB1\|0.9% | A | TERT; LINC01242; NFATC2; CPA6 |
| HCCscreen17 | TP53\|2.8 | A | TERT; ELAC2; DHX15 |
| HCCscreen18 | TERT\|15%; CTNNB1\|15.4% | C | APOBEC4; FBX010; FUT8; WDR7; SLC7A10; GUSBP4 |
| HCCscreen19 | TERT\|0.5%; TP53\|0.3; CTNNB1\|0.2% | — | — |
| HCCscreen20 | TP53\|0.1%; CTNNB1\|0.7% | A | RAB9BP1; NLGN1; HTR2A |
| HCCscreen21 | TP53\|1%; AXIN1\|0.2% | A | TERT; FRG2B; LOC100506; AADAT |
| HCCscreen22 | TP53\|32%; CTNNB1\|0.7% | B | LINC00871 |
| HCCscreen23 | CTNNB1\|0.1% | A | LINC00273; LOC100294362 |
| HCCscreen24 | — | B | MARCH1; GLP2R |
| HCCscreen25 | — | B | CCDC60; PLXDC2; CCDC173 |
| HCCscreen26 | — | B | SUGCT; EGLLN3; PCBP3 |
| HCCscreen27 | — | B | ADAMTSL1; LOC101929; NMNAT2; FGF12 |
| HCCscreen28 | — | B | PTGER1; SLC39A11; ABHD4; LOC100507 |
| HCCscreen29 | — | — | — |
| HCCscreen30 | — | — | — |
| HCCscreen31 | — | — | — |
| HCCscreen32 | TP53\|0.5% | B | KIF26B |
| HCCscreen33 | — | C | TUNAR |
| HCCscreen34 | — | A | CC2D2A; DCAF8L1; MGAT4C; RAD23B; RASA2 |
| HCCscreen35 | — | — | — |
| HCCscreen36 | — | — | — |
| HCCscreen37 | — | — | — |
| HCCscreen38 | — | — | — |
| HCCscreen39 | — | — | — |
| HCCscreen40 | — | C | C11ORF63 |
| HCCscreen41 | — | C | SYT10; UTR3 |
| HCCscreen42 | — | A | SYNDIC1; AK4; TPM3; LINC01021 |
| HCCscreen43 | — | C | LOC728637 |
| HCCscreen44 | — | C | PRKAA1; RND219 |
| HCCscreen45 | — | B | NEDD4; TET2 |

TABLE 7-continued

| Number | Mutant gene mutation frequency | HBV integration score | HBV integration gene |
|---|---|---|---|
| HCCscreen46 | — | B | YWHAZ; SNX16; FRG2B |
| HCCscreen47 | — | B | ZNF716; TMTC2; PDE4DIP; KIF16B |
| HCCscreen48 | — | — | — |
| HCCscreen49 | — | — | — |
| HCCscreen50 | — | — | — |
| HCCscreen51 | — | — | — |
| HCCscreen52 | TP53|0.13%; AXIN1|0.27% | — | — |
| HCCscreen53 | — | — | — |
| HCCscreen54 | — | — | — |
| HCCscreen55 | — | — | — |
| HCCscreen56 | — | — | — |
| HCCscreen57 | — | — | — |
| HCCscreen58 | — | — | — |
| HCCscreen59 | — | — | — |
| HCCscreen60 | — | — | — |
| HCCscreen61 | — | — | — |
| HCCscreen62 | — | — | — |
| HCCscreen63 | — | — | — |
| HCCscreen64 | — | — | — |
| HCCscreen65 | — | — | — |
| HCCscreen66 | — | — | — |
| HCCscreen67 | — | — | — |
| HCCscreen68 | TERT|0.06% | — | — |
| HCCscreen69 | AXIN|0.13% | — | — |
| HCCscreen70 | — | — | — |
| HCCscreen71 | — | — | — |
| HCCscreen72 | — | — | — |
| HCCscreen73 | — | — | — |
| HCCscreen74 | — | — | — |
| HCCscreen75 | — | — | — |
| HCCscreen76 | — | — | — |
| HCCscreen77 | — | — | — |
| HCCscreen78 | — | — | — |
| HCCscreen79 | — | — | — |
| HCCscreen80 | — | — | — |
| HCCscreen81 | — | — | — |
| HCCscreen82 | — | — | — |
| HCCscreen83 | — | — | — |
| HCCscreen84 | — | — | — |
| HCCscreen85 | — | — | — |
| HCCscreen86 | — | — | — |
| HCCscreen87 | — | — | — |
| HCCscreen88 | — | — | — |
| HCCscreen89 | — | — | — |
| HCCscreen90 | — | — | — |

Note:
"—" indicates that no mutation was detected and "—" indicates that no integration was detected.

3. Taking the cfDNA library of the blood sample to be detected prepared in the step 2 (1), performing low-depth whole genome sequencing, and then performing CNV detection on sequencing data (about 3G).

III. Detecting the AFP Content in the Plasma

The blood samples to be detected are 65 liver cancer patient blood samples, 70 liver cancer high-risk patient blood samples and 100 healthy person blood samples.

1 Taking a blood sample to be detected, uniformly mixing in a blood collection tube upside down for 10 times, centrifuging for 10 min at 4° C. and 2000 g, then transferring the upper-layer plasma to a centrifuge tube (the specification is 1.5 mL), centrifuging for 10 min at 4° C. and 16000 g, and collecting the supernatant (i.e. plasma).

2. After completing the step 1, taking the plasma and detecting AFP by American Abbott IMx analyzer.

The results of the determination of AFP content in plasma of some of the blood samples to be detected are shown in column 2, Table 8.

TABLE 8

| Number | AFP(ng/mL) | DCP(mAU/mL) | Number | AFP(ng/mL) | DCP(mAU/mL) |
|---|---|---|---|---|---|
| HCCscreen01 | 6.5 | 178 | HCCscreen46 | 107.99 | 27.52 |
| HCCscreen02 | 97.09 | 98 | HCCscreen47 | 28.96 | 19.74 |
| HCCscreen03 | 12 | 265 | HCCscreen48 | 22.6 | 28.38 |
| HCCscreen04 | 238.7 | 38.59 | HCCscreen49 | 95.88 | 17.92 |
| HCCscreen05 | 1210 | 22.71 | HCCscreen50 | 25.2 | 33.21 |
| HCCscreen06 | 5.37 | 19.14 | HCCscreen51 | 2.55 | 25.95 |
| HCCscreen07 | 2136.1 | 18.58 | HCCscreen52 | 1.24 | 22.73 |
| HCCscreen08 | 1380.46 | 50.14 | HCCscreen53 | 2.7 | 31.31 |
| HCCscreen09 | 1843.39 | 23.06 | HCCscreen54 | 4.51 | 20.76 |
| HCCscreen10 | 2.3 | 180.03 | HCCscreen55 | 3.27 | 34.29 |
| HCCscreen11 | 2.06 | 12.87 | HCCscreen56 | 1.67 | 16.64 |

TABLE 8-continued

| Number | AFP(ng/mL) | DCP(mAU/mL) | Number | AFP(ng/mL) | DCP(mAU/mL) |
|---|---|---|---|---|---|
| HCCscreen12 | 1.79 | 11.39 | HCCscreen57 | 2.42 | 25.03 |
| HCCscreen13 | 3338.52 | >30000 | HCCscreen58 | 3.09 | 28.6 |
| HCCscreen14 | 1.92 | 72.66 | HCCscreen59 | 4.87 | 19.58 |
| HCCscreen15 | 1.71 | 81.47 | HCCscreen60 | 3.12 | 17.63 |
| HCCscreen16 | 1811.25 | 304.45 | HCCscreen61 | 1.04 | 25.33 |
| HCCscreen17 | 6.55 | 20.84 | HCCscreen62 | 0.973 | 21.49 |
| HCCscreen18 | 26.22 | 188.95 | HCCscreen63 | 1.29 | 22.82 |
| HCCscreen19 | 7.66 | 423.93 | HCCscreen64 | 2 | 15.77 |
| HCCscreen20 | 130.95 | 148.62 | HCCscreen65 | 2.05 | 18.97 |
| HCCscreen21 | 14.48 | 2464.26 | HCCscreen66 | 2.5 | 22.13 |
| HCCscreen22 | 199.35 | 342.12 | HCCscreen67 | 1.04 | 37.64 |
| HCCscreen23 | 117.1 | 26.67 | HCCscreen68 | — | — |
| HCCscreen24 | 21.27 | 27.75 | HCCscreen69 | — | — |
| HCCscreen25 | 49.62 | 13.24 | HCCscreen70 | — | 20.63 |
| HCCscreen26 | 28.34 | 39.51 | HCCscreen71 | 1.49 | 26.29 |
| HCCscreen27 | 31.64 | 15.49 | HCCscreen72 | 1.54 | 15.4 |
| HCCscreen28 | 37.33 | 21.09 | HCCscreen73 | 2.29 | 19.8 |
| HCCscreen29 | 33.02 | 27.5 | HCCscreen74 | 4.02 | 14.7 |
| HCCscreen30 | 108.3 | 39.45 | HCCscreen75 | 1.45 | 29.64 |
| HCCscreen31 | 32.24 | 33.92 | HCCscreen76 | 2.11 | 26.1 |
| HCCscreen32 | 119.9 | 21.06 | HCCscreen77 | 4.52 | 15.12 |
| HCCscreen33 | 1.86 | 10.37 | HCCscreen78 | 3.69 | 18.49 |
| HCCscreen34 | 4.81 | 9.19 | HCCscreen79 | 2.65 | 32.78 |
| HCCscreen35 | 1 | 18.34 | HCCscreen80 | 5.47 | 25.68 |
| HCCscreen36 | 2.7 | 11.44 | HCCscreen81 | 2.21 | 17.95 |
| HCCscreen37 | 309.58 | 11.02 | HCCscreen82 | 2.33 | 21.52 |
| HCCscreen38 | 7.78 | 17.99 | HCCscreen83 | 2.41 | 27.08 |
| HCCscreen39 | 4.33 | 14.69 | HCCscreen84 | 2.77 | 23.78 |
| HCCscreen40 | 24.7 | 25.07 | HCCscreen85 | 3.6 | 17.76 |
| HCCscreen41 | 35.87 | 21.34 | HCCscreen86 | 6.55 | 30.78 |
| HCCscreen42 | 770.97 | 23.32 | HCCscreen87 | 2.76 | 24.36 |
| HCCscreen43 | 21.85 | 19.83 | HCCscreen88 | 3.12 | 35.14 |
| HCCscreen44 | 43.84 | 17.12 | HCCscreen89 | 2.86 | 38.26 |
| HCCscreen45 | 32.66 | 24.85 | HCCscreen90 | 3.46 | 22.29 |

IV. Detecting the DCP Content in the Plasma

The blood samples to be detected are 65 liver cancer patient blood samples, 70 liver cancer high-risk patient blood samples and 100 healthy person blood samples.

1 Taking a blood sample to be detected, uniformly mixing in a blood collection tube upside down for 10 times, centrifuging for 10 min at 4° C. and 2000 g, then transferring the upper-layer plasma to a centrifuge tube (the specification is 1.5 mL), centrifuging for 10 min at 4° C. and 16000 g, and collecting the supernatant (i.e. plasma).

2. After completing the step 1, taking the plasma and detecting the content of DCP by American Abbott ARCHITECT i2000SR chemiluminescence immuno-analyzer.

The results of the determination of DCP content in plasma of some of the blood samples to be detected are shown in column 3, Table 8.

V. Data Processing and Obtaining 22 Characteristic Scores

1. Annotating and Scoring of Gene Mutation Results

Annotating the detection result of the liver cancer mutant gene in the cfDNA in step II: annotation score for mutation reads support frequency. Mutation reads support reflects to a large extent the percentage of differentiated cells in the tissue and is therefore an important phenotypically relevant factor.

2. Mutation Site Integration and Scoring

For each gene mutation, giving an annotation score according to the mutation reads support frequency; the mutation site scores are then accumulated into different ROI (Region Of Interest) intervals (i.e., obtaining characteristic scores). The interval includes four genes (TP53, CTNNB1, TERT and AXIN1) and a TP53 R249S hotspot mutation site region. The calculation formula is as follows:

$$ROI = \log 2 \sum_{i=1}^{n} \text{adj\_score}_i$$

Where n is the number of mutations overlapping the ROI and adj_score is the reads support frequency of the mutation.

3. The Structural Variation Result Characteristic Extraction (1) Detecting the score of the HBV and TERT integration variation characteristic of each sample: TERT integration occurs, and the characteristic score of TERT integration variation is 1; TERT integration did not occur, and the characteristic score of TERT integration variation was 0.

(2) Detecting the characteristic score of HBV integration variation in each sample: for each integration mutation detected, it was divided into three grades A, B and C according to the reads support credibility (the number of integrated reads ≥10, grade A; 10>the number of integrated reads >6, grade B; 10>Integrated reads >6, Grade B; the rest was grade C, as shown in column 3 of Table 7), and the corresponding scores were 1, 0.8 and 0.3 respectively, and then summed up to obtain the characteristic score of HBV integration variation.

4. Feature Extraction of Gene Copy Number Variation Detection Results

The CNV detection results in step II are processed as follows: dimensionality reduction is performed on the 44 CNV signals (the sex chromosomes were deleted to rule out the effect of gender on CNV signal) score at each chromosome arm level, the first six principal components (CNV dimensionality reduction characteristic 1, CNV dimensionality reduction characteristic 2, CNV dimensionality reduction characteristic 3, CNV dimensionality reduction characteristic 4, CNV dimensionality reduction characteristic 5, CNV dimensionality reduction characteristic 6) were selected as CNV-related characteristics by $R^2$ value, the $R^2$ values of CNV dimensionality reduction characteristics 1, CNV dimensionality reduction characteristics 2, CNV dimensionality reduction characteristics 3, CNV dimensionality reduction characteristics 4, CNV dimensionality reduction characteristics 5 and CNV dimensionality reduction characteristics 6 are characteristic scores.

5. Extraction of Cell Free DNA Length Related Characteristic

The inventors of the present invention calculated the percentage of the length of the cfDNA fragment in four intervals (<90 bp, 90-140 bp, 141-200 bp and >200 bp), taking the characteristics as prediction variables, the percentage of the length of the cfDNA fragment in the four intervals is a characteristic score.

6. The Related Characteristic Extraction of the Protein Marker

Dividing actual measured values of AFP into five numerical levels from low to high according to threshold values (13, 20, 200, 400): 0, 5, 8, 20 and 30, dividing actual measured values of the DCP into three numerical levels from low to high according to threshold values (40 and 60): 0, 2, 5 as characteristic scores of two protein markers.

7. Extraction of Clinic and Experiment Related Characteristic

Clinical characteristics including patient age, sex, and cfDNA concentration (cfDNA content/plasma volume) were also correlated with case phenotype and were included in the model. Wherein, the cfDNA concentration values were taken as characteristic scores after log 2; the characteristic value of the age is the actual age value of the sample; The characteristic score of male is 1, and that of female is 0.

In summary, 22 characteristics are composed of 13 gene mutation characteristics, 2 protein markers, 5 cfDNA physical characteristics and the basic information composition of 2 blood sample. The 13 gene mutations characteristics are a TP53 gene mutation, a TERT gene mutation, an AXIN1 gene mutation, a CTNNB1 gene mutation, a TP53 R249S hot spot region, a CNV dimensionality reduction characteristic 1, a CNV dimensionality reduction characteristic 2, a CNV dimensionality reduction characteristic 3, a CNV dimensionality reduction characteristic 4, a CNV dimensionality reduction characteristic 5 and a CNV dimensionality reduction characteristics 6, HBV and TERT integrated variation, HBV and non-TERT integrated variation, respectively. The two protein markers were AFP and DCP, respectively. The five physical characteristics of cfDNA were as follows interval percentage of cell free DNA fragment length less than 90 bp, interval percentage of cell free DNA fragment 90-140 bp, interval percentage of cell free DNA fragment 141-200 bp, interval percentage of cell free DNA fragment greater than 200 bp and the concentration of cfDNA respectively concentration. The basic information of 2 blood sample is sex and age, respectively.

VI. Predicting Liver Cancer

1. Obtaining characteristic scores of 22 characteristics of persons to be detected according to the method in the steps I to V;

2. Taking the characteristic score obtained in the step 1 as a parameter, the training set data of 135 samples including 65 HCC cases and 70 liver cancer high-risk patients were modeled by using the penalty logistic regression algorithm, and the HCCscreen score was calculated. In order to perform cluster analysis of gene, protein and CNV levels respectively, the cross-validation coefficient of each characteristic using penalty logic regression is also given. The model is started in the R package 'glmnet' (R version 3.5.1), and the penalty parameter a is optimized in the training data set by 10-fold cross validation, and the optimized value is 0. The ROC curve (receiver operating characteristic curve) is then plotted by the HCC Screen score and sample grouping (cancerous or non-cancerous) information. The HCCScreen score corresponding to the maximum Youden's index was taken as the threshold. In this model, 0.4 was chosen as the best cut-off value for the model.

When HCC Screen >0.4, it was interpreted as liver cancer, otherwise it was interpreted as non-liver cancer.

VII. Verifying the Validity of the Liver Cancer Prediction Model

Taking the liver cancer group (composed of 65 patients with liver cancer), the liver cancer high-risk group (composed of 70 patients with high risk of liver cancer) and the healthy group (composed of 100 healthy volunteers) as samples, the validity of the prognosis method of the prediction model of the liver cancer in step VII was verified.

Figure 7:
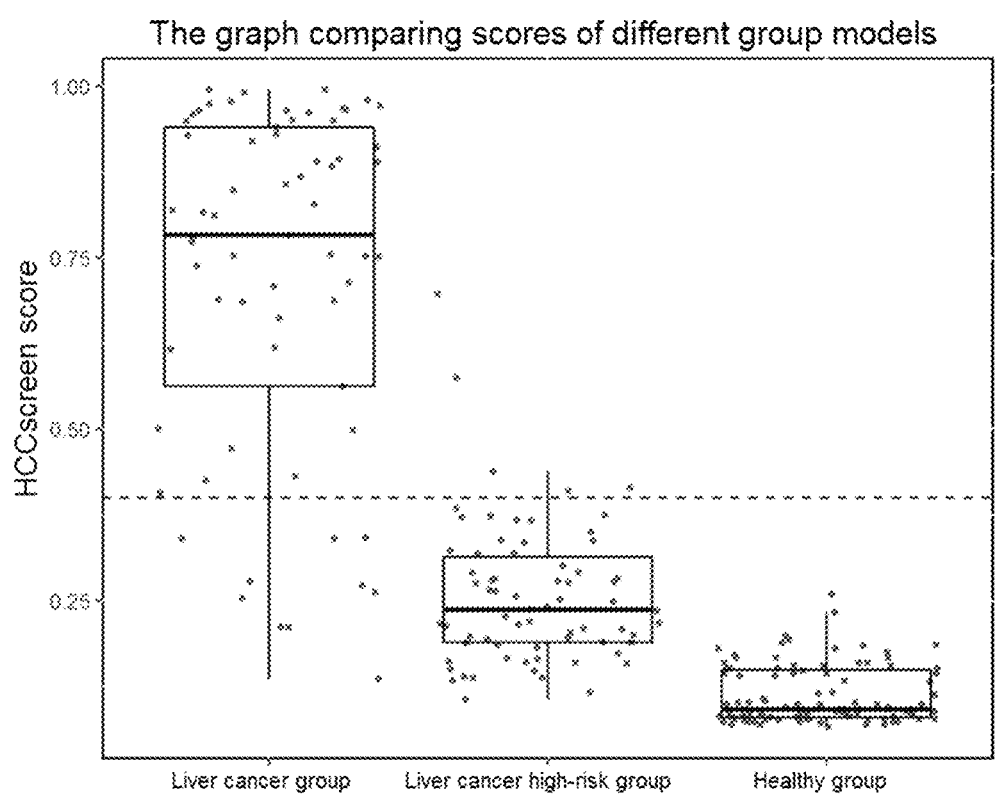
FIG. 7 is a graph comparing scores of different group models.

The results are shown in FIG. 7. The results show that the liver cancer prediction model can predict whether the persons to be detected are liver cancer patients or not.

INDUSTRIAL APPLICATIONS

The inventors of the present invention firstly confirmed that gene mutation information of cfDNA in plasma can be used for early HCC prediction through a large number of experiments. According to the invention, a liver cancer prediction model is adopted to score a person to be detected, and whether the person to be detected is a liver cancer patient or not is predicted through a score value, so that the effective HCC early screening effect of the combination of the gene marker and the protein marker disclosed by the invention can be verified. Therefore, the detection of cfDNA for early screening, disease tracking, efficacy evaluation, prognosis prediction of liver cancer has important clinical significance.

The invention claimed is:

1. A method for early screening for hepatocellular carcinoma in alpha-feto protein (AFP) negative subjects, comprising
obtaining characteristic scores of gene mutation characteristics, content of protein markers, cell-free (cfDNA) physical characteristics and clinical characteristics of the subjects;
wherein, the gene mutation characteristics comprise the following 13 gene mutation characteristics: a tumor protein p53 (TP53) gene non-R249S mutation, a telomerase reverse transcriptase (TERT) gene mutation, an axis inhibition protein 1 (AXIN1) gene mutation, a catenin beta 1 (CTNNB1) gene mutation, a TP53 R249S hot spot region mutation, a copy number variation (CNV) dimensionality reduction characteristic 1, a CNV dimensionality reduction characteristic 2, a CNV dimensionality reduction characteristic 3, a CNV dimensionality reduction characteristic 4, a CNV dimensionality reduction characteristic 5 and a CNV dimensionality reduction characteristics 6, hepatitis B virus (HBV) and TERT integrated variation, HBV and non-TERT integrated variation;
the protein markers comprise AFP and des-gamma-carboxy prothrombin (DCP);
the cfDNA physical characteristics comprise the following 5 cfDNA physical characteristics: interval percentage of cfDNA fragment length less than 90 bp, interval percentage of cfDNA fragment 90-140 bp, interval percentage of cfDNA fragment 141-200 bp, interval percentage of cfDNA fragment greater than 200 bp and the concentration of cfDNA;

the clinical characteristics comprise at least blood sample information including sex and age;

inputting the characteristic scores of the gene mutation characteristics, the content of the protein markers, the cfDNA physical characteristics and the clinical characteristics into a liver cancer prediction model, calculating a hepatocellular carcinoma screening score; and comparing the screening score with a threshold value to determine whether the subject is a liver cancer patient;

wherein the hepatocellular carcinoma screening score and the threshold value are obtained through the liver cancer prediction model;

and wherein the method for constructing the prediction model of liver cancer includes:

constructing a training set, wherein the training set consists of a plurality of liver cancer patients and a plurality of patients at high risk of liver cancer;

taking gene mutation characteristics, the content of the protein markers, cfDNA physical characteristics and clinical characteristics of a training set as characteristics, converting detection results into characteristic scores, constructing a liver cancer prediction model by using a penalty logistic regression algorithm, and calculating a hepatocellular carcinoma screening score; and obtaining a receiver operating characteristic (ROC) curve of sensitivity and specificity of the penalty logistic regression model according to the hepatocellular carcinoma screening score and the sample grouping information, and determining a cut-off value according to the ROC curve, wherein the cut-off value serves as a threshold value for distinguishing liver cancer patients from patients at high risk of liver cancer.

2. The method according to claim 1, wherein the characteristic scores of gene mutation characteristics of the TP53 non-R249S mutation, the CTNNB1 gene mutation, the TERT gene mutation, the AXIN1 gene mutation, and the TP53 R249S hotspot mutation are obtained as follows:

(1) annotating the detection result of the liver cancer mutant gene as annotation score for mutation reads support frequency;

(2) giving an annotation score according to the mutation reads support frequency; the mutation site scores are then accumulated into different ROI (Region Of Interest) intervals to obtain characteristic scores;

wherein, the interval includes four genes TP53, CTNNB1, TERT and AXIN1, as well as a TP53 R249S hotspot mutation site region, and are calculated as follows:

$$ROI = \log 2 \sum_{i=1}^{n} adj\_score_i$$

n is the number of mutations overlapping the ROI and adj_score is the reads support frequency of the mutation.

3. The method according to claim 1, wherein the characteristic scores of gene mutation characteristics of HBV and TERT/non-TERT integrated variation are obtained as follows:

(1) when detecting whether HBV is integrated with a TERT gene, detecting the score of the HBV and TERT integration variation characteristic of each sample: if TERT integration occurs, and the characteristic score of TERT integration variation is 1; if TERT integration did not occur, and the characteristic score of TERT integration variation is 0;

(2) when detecting whether HBV is integrated with a non-TERT gene, detecting the characteristic score of HBV integration variation in each sample: for each integration mutation detected, it is divided into three grades A, B and C according to the reads support credibility (the number of integrated reads ≥10, grade A; 10>the number of integrated reads>6, grade B; 10>Integrated reads>6, Grade B; the rest is grade C), and the corresponding scores are 1, 0.8 and 0.3 respectively, and then summed up to obtain the characteristic score of HBV integration variation.

4. The method according to claim 1, wherein the characteristic scores of gene mutation characteristics of CNV dimensionality reduction characteristics are obtained as follows:

calculating $R^2$ values of the CNV dimensionality reduction characteristics 1, CNV dimensionality reduction characteristics 2, CNV dimensionality reduction characteristics 3, CNV dimensionality reduction characteristics 4, CNV dimensionality reduction characteristics 5 and CNV dimensionality reduction characteristics 6 to obtain the characteristic scores.

5. The method according to claim 1, wherein, the characteristic scores of the content of the protein markers are obtained as follows:

dividing actual measured values of AFP into five numerical levels from low to high according to threshold values (13, 20, 200, 400): 0, 5, 8, 20 and 30, dividing actual measured values of the DCP into three numerical levels from low to high according to threshold values (40 and 60): 0, 2, 5 as characteristic scores of two protein markers.

6. The method according to claim 1, wherein, the characteristic score of the cfDNA physical characteristics are obtained as follows:

calculating the percentage of the length of the cfDNA fragment in four intervals (<90 bp, 90-140 bp, 141-200 bp and >200 bp), taking the characteristics as prediction variables, the percentage of the length of the cfDNA fragment in the four intervals is a characteristic score;

the cfDNA concentration values are taken as characteristic scores after log 2.

7. The method according to claim 1, wherein, the characteristic scores of the clinical characteristics are obtained as follows:

the characteristic value of the age is the actual age value of the sample, the characteristic score of male is 1, and that of female is 0.

* * * * *